US010793590B2

(12) United States Patent
Van Arnam et al.

(10) Patent No.: US 10,793,590 B2
(45) Date of Patent: Oct. 6, 2020

(54) ANTIFUNGAL COMPOUNDS

(71) Applicants: President and Fellow of Harvard College, Cambridge, MA (US); Wisconsin Alumni Research Foundation, Madison, WI (US); Universidad de Costa Rica, San José (CR)

(72) Inventors: Ethan Van Arnam, Somerville, MA (US); Clarissa Sit, Brookline, MA (US); Antonio Ruzzini, Brookline, MA (US); Jon Clardy, Jamaica Plain, MA (US); Cameron Currie, Madison, WI (US); Adrian Alberto Pinto-Tomas, San José (CR)

(73) Assignees: President and Fellows of Harvard College, Cambridge, MA (US); Wisconsin Alumni Research Foundation, Madison, WI (US); Universidad de Costa Rica, San José (CR)

( * ) Notice: Subject to any disclaimer, the term of this patent is extended or adjusted under 35 U.S.C. 154(b) by 0 days.

(21) Appl. No.: 16/305,965

(22) PCT Filed: Jun. 2, 2017

(86) PCT No.: PCT/US2017/035697
§ 371 (c)(1),
(2) Date: Nov. 30, 2018

(87) PCT Pub. No.: WO2017/210565
PCT Pub. Date: Dec. 7, 2017

(65) Prior Publication Data
US 2019/0211047 A1   Jul. 11, 2019

Related U.S. Application Data

(60) Provisional application No. 62/397,079, filed on Sep. 20, 2016, provisional application No. 62/345,516, filed on Jun. 3, 2016.

(51) Int. Cl.
*C07H 17/08* (2006.01)
*C12P 19/62* (2006.01)
*C12N 15/52* (2006.01)
*A61P 31/10* (2006.01)

(52) U.S. Cl.
CPC .............. *C07H 17/08* (2013.01); *A61P 31/10* (2018.01); *C12N 15/52* (2013.01); *C12P 19/62* (2013.01)

(58) Field of Classification Search
CPC ...................................... C07H 17/08
USPC ....................................... 549/415
See application file for complete search history.

(56) References Cited

U.S. PATENT DOCUMENTS

2014/0371436 A1   12/2014   Kim et al.

FOREIGN PATENT DOCUMENTS

WO   WO-2001/27284 A2   4/2001
WO   WO-2012/012782 A1   1/2012

OTHER PUBLICATIONS

Van Arnam et al., "Selvamicin, an atypical antifungal polyene from two alternative genomic contexts," Proc Natl Acad Sci U S A, 113(46): 12940-12945 (2016).
International Search Report and Written Opinion for International Application No. PCT/US2017/035697 dated Oct. 19, 2017.

*Primary Examiner* — Taofiq A Solola
(74) *Attorney, Agent, or Firm* — Foley Hoag LLP

(57) ABSTRACT

Compounds of formula (I) or formula (II), compositions and methods useful for treating and/or preventing a fungal infections are provided. wherein the substituents are as defined in the appended claims.

9 Claims, 54 Drawing Sheets

A

B

C

D

E

F

G

H

A

B

C

D

E

F

Figure 11
A
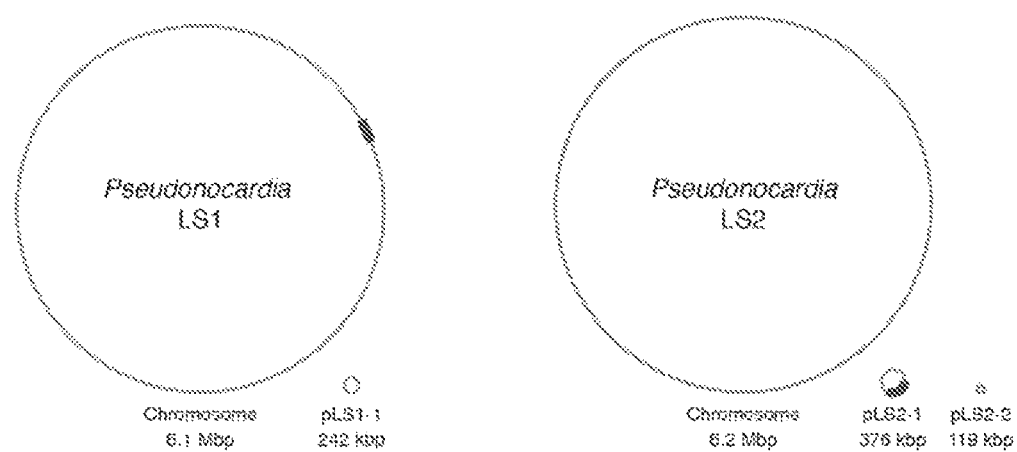
B
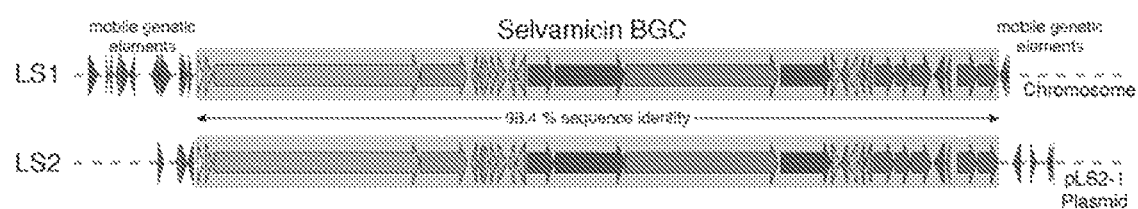

Figure 12
A
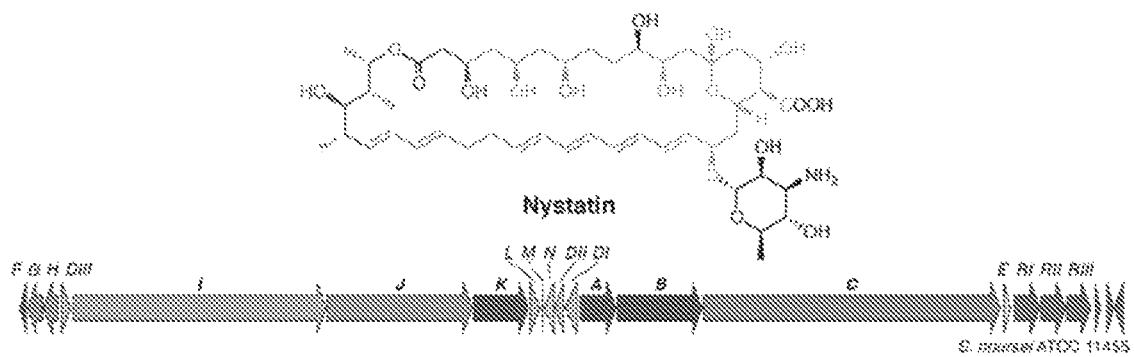
B
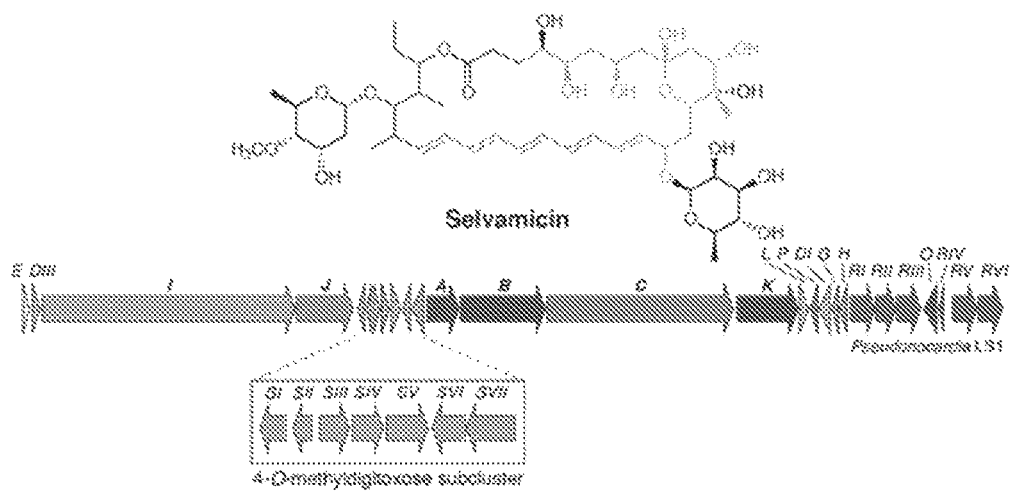

Figure 14

Figure 16
A
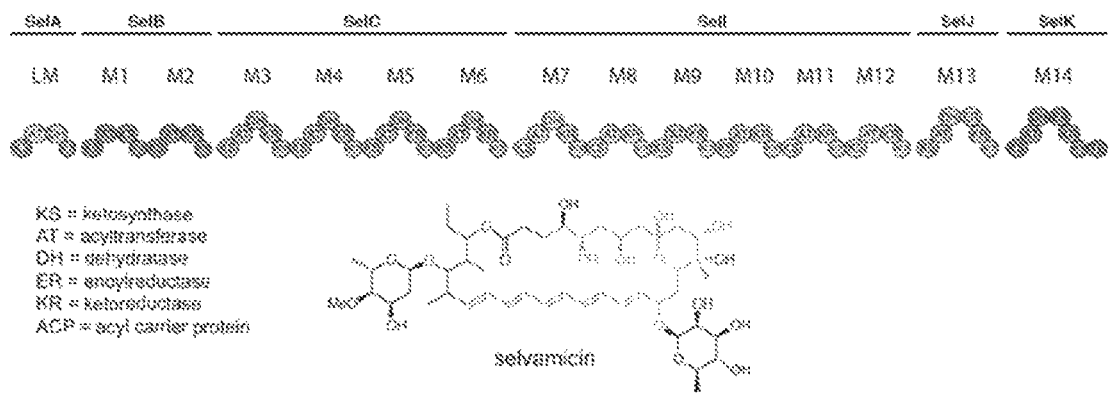
B
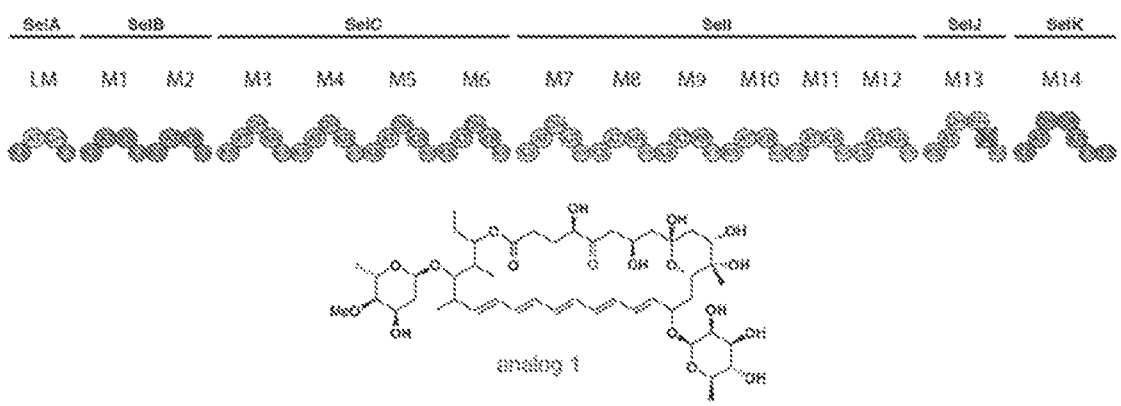
C
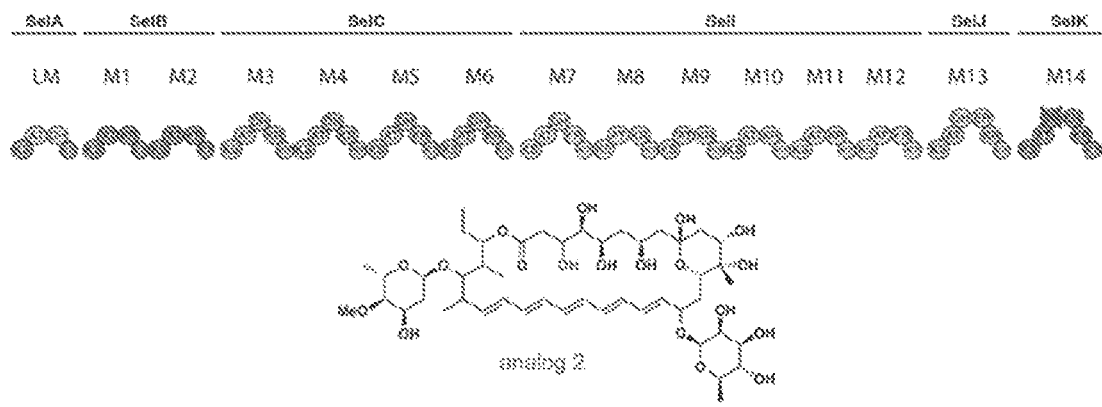

Figure 17

| Putative Protein | Putative Function | LSI top blastp hit v. nr proteins (% identity) | Nys BGC homolog (% identity) |
|---|---|---|---|
| SelE | Thioesterase | Proofreading thioesterase | oleoyl-ACP hydrolase [Streptomyces sp. NRRL S-1868] (60%) | NysE (45%) |
| SelDIII | CDP-mannose 4,6-dehydratase | 6-deoxymannose biosynthesis | CDP-mannose 4,6-dehydratase [Streptomyces natalensis] (79%) | NysDIII (78%) |
| SelI | Type I PKS | PKS modules 7-12 | beta-ketoacyl synthase [Streptomyces sp. NRRL B-24881] (61%) | NysI (60%) |
| SelJ | Type I PKS | PKS module 13 | hypothetical protein VR61_12010 [Streptomyces sp. NRRL B-1568] (61%) | NysJ (58%) |
| SelSI | O-methyltransferase | 4-O-methyldigitoxose biosynthesis | amemin O-methyltransferase [Streptomyces sp. 769] (58%) | --- |
| SelSII | dTDP-4-dehydrorhamnose 3,5-epimerase | 4-O-methyldigitoxose biosynthesis | dTDP-4-dehydrorhamnose 3,5-epimerase [Actinobacteria bacterium OK006] (70%) | --- |
| SelSIII | glucose-1-phosphate thymidylyltransferase | 4-O-methyldigitoxose biosynthesis | glucose-1-phosphate thymidylyltransferase [Streptomyces sioyaensis] (73%) | --- |
| SelSIV | dTDP-glucose 4,6-dehydratase | 4-O-methyldigitoxose biosynthesis | dTDP-glucose 4,6-dehydratase [Actinokineospora auranticola] (78%) | --- |
| SelSV | Glycosyltransferase | 4-O-methyldigitoxose glycosyltransfer | protein IroB [Streptomyces sp. NRRL F-5126] (49%) | --- |
| SelSVI | dTDP hexose 3-ketoreductase | 4-O-methyldigitoxose biosynthesis | oxidoreductase [Streptomyces mellesdiae] (55%) | --- |
| SelSVII | dTDP-hexose 2,3-dehydratase | 4-O-methyldigitoxose biosynthesis | NDP hexose 2,3-dehydratase [Scissionella sp. SE31] (58%) | --- |
| SelA | Type I PKS | PKS loading module | amalate polyketide synthase [Streptomyces hiroshimensis] (47%) | NysA (46%) |
| SelB | Type I PKS | PKS modules 1-2 | polyketide synthase [Streptomyces scopuliridis] (62%) | NysB (61%) |
| SelC | Type I PKS | PKS modules 3-6 | type I polyketide synthase [Streptomyces sp. NRRL B-24881] (58%) | NysC (56%) |
| SelK | Type I PKS | PKS module 14+ thioesterase | type I polyketide synthase [Streptomyces sp. TAA204] (57%) | NysK (51%) |
| SelL | P450 monooxygenase | hydroxylation | cytochrome P450 [Streptomyces reseoverticillatus] (54%) | NysL (53%) |
| SelF | 2-oxoglutarate and Fe(II)-dependent oxygenase | hydroxylation | phytanoyl-CoA dioxygenase [Streptomyces hiroshimensis] (68%) | --- |
| SelDI | Glycosyltransferase | 6-deoxymannose glycosyltransfer | MGT family glycosyltransferase [Streptomyces sp. AcH 505] (66%) | NysDI (63%) |
| SelG | ABC transporter | Efflux | ABC transporter permease [Saccharothrix syringae] (51%) | --- |
| SelH | ABC transporter | Efflux | ABC transporter [Saccharothrix sp. NRRL B-16348] (67%) | NysH (58%) |
| SelRI | Transcriptional regulator | Regulation | CppRI [Pseudonocardia autotrophica] (73%) | NysRI (45%) |
| SelRII | Transcriptional regulator | Regulation | CppRII [Pseudonocardia autotrophica] (57%) | NysRII (32%) |
| SelRIII | Transcriptional regulator | Regulation | hypothetical protein WY82_09420 [Pseudonocardia sp. AL041005-10] (60%) | NysRIII (33%) |
| SelO | Decarboxylase | Unknown | CppO [Pseudonocardia autotrophica] (90%) | --- |
| SelRIV | Transcriptional regulator | Regulation | CppRIV [Pseudonocardia autotrophica] (74%) | ORF4 (42%) |
| SelRV | Transcriptional regulator | Regulation | CppRV [Pseudonocardia autotrophica] (54%) | --- |
| SelRVI | Transcriptional regulator | Regulation | hypothetical protein [Pseudonocardia sp. EC080625-04] | --- |

*Predicted genes/pseudogenes and the gene products derived from sequences <250 bp are omitted from the table
†Nystatin BGC from S. noursei ATCC 11455 (accession no. AF263912)

Figure 18

| SEQ ID NO. | Accession ID | Protein name | Sequence |
|---|---|---|---|
| 2 | AIE82578.1 | SelE | 1 mrrfhspgrd earlvcfpha ggsatifhpv sarfapaaev lavqypgrqd rhrepcltsv<br>61 aeladrlaie laalparptv ffghsmgalv gfeaarrler dapgsaprsl vvsgrrapst<br>121 rrpervheld dagllaevra idgpdmsald ddflalvlpa lrndyravet yradgavvg<br>181 cpvlaitgrd dprttgeead awrrhtdggf elevmpghhf flvdqaravc drldeqlala<br>241 hggsarpprg |
| 3 | AIE82579.1 | SelDIII | 1 makrailtgi tgqdgsylae hlislgygvw gltrgqanph kmrvqklase lsfvdgdlmd<br>61 qgslvsavdr vqpdevynlg aisfvamswg qaelvtevna vgvlrmleai rmvsglttsr<br>121 qaadgqirfy qasssemfgk vtespqneqt vlhprspygv skayghimtr nyresygmfg<br>181 vsgilfnhes prrgpefvtr kislavaqik lglqkelrig nldavrdwgf agdvvramrl<br>241 mlaqdepvdh vvgtgrvhsv rdavriafec vginwedhvv vdpalvrpae velicadstr<br>301 arenlgweps idfpelmgmm vesdirragr erdyaevlsa gsw |
| 4 | AIE82580.1 | SelI | 1 mdneqklrdy lkrasadlqr trqrvqelee asrepiaivg mscrypggva gpddlwqmva<br>61 tgsdgisglp tdrgwdldge laaaatsggf lhdaaefdad ffgispreal amdpqqrill<br>121 evaweafera gvdpasvrgs rtgmfigama qdyrvgpddg vegfvltgss ssvvsgriav<br>181 sfgtvgpavt vdtacssslv slhlaahalr agecsmalag gitvmstpat fiefarqggl<br>241 atdgrcrsfa dsaagtgwae gvglvlierl sdaqrnghev lavvrgsavn qdgasnglta<br>301 pngpsqqrvi sealtrsgls adqvdvveah gtgttlgdpv eaqallatyg qrrerplwlg<br>361 svksnishtq aaagvagvik mveairngvl patlhvdtps tkvdwdsgqv riltesmpwp<br>421 atgaprraav ssfgisgtna htileqapdt pdapvvvpah dadgapapl lisgrtaeal<br>481 saqaerlidr ldaadapdlr dvafslatgr aslehravip addaeqtrag lralaegtia<br>541 pgavrgtsrr rpstafifag qgsqrlgmgr elyrrfpvfa eafdavcehl dpsvreivwg<br>601 tdacalndtg vaqpalfale valhrlvssy gvrptqligh sigeiaaahv agvfsipdac<br>661 alvtargrlm rsipaggamv aiaaseeeva phitdgvsla avngpssvvv sgteaevhdv<br>721 vehfadrirtr rlrvshafhs plmepmlaef ravvaglidac aptlpivstl tgrpataeel |

Figure 18 (Continued)

```
 781 gsaeywaaha rgtvrfiadav atartlgvtd llelgpdatl cgaarsclda agaedaatlp
 841 vlradrdeaa tlteamaglh vrgvavdrnt lvdgtgahrv dlptyafrrr rfwpkgpaaa
 901 ggdvraaglg aahhpliaaa valadsdgvl ltgrlsiaaq pwladhavhg rvlipgtafl
 961 elairagdev gadhveelti aaplvlpesg gvgvgvwlgs pdasgrrvvt vysrpddadd
1021 epwtrhatgv lgrggpaadt apattgpewp pagaeaidvt gaydslaaag leygttfggl
1081 raawrrddev faevalpqsa gtegfgvhpa lidaalhala iagsgedtgt slpfswegar
1141 lhaggasavr vritgagtdt vslvvsdpag dpvatvasla lrplpaggva gdtagrtplf
1201 aveptpvrlg eapasfalld pagligstfa paplydslae ladagvpevv aapvpavegd
1261 vpgavravta waldllgrwi aderfagsrl vlitrgadld pvhasvvgla rtaqaecpgr
1321 vavldigpdg saadtpspat vvaalgtade pelairgeda vaprltrlip pgaagtpapf
1381 dadstvlitg gtgglgavia rhlvaghgvr slvlagrrgp eapgaaelaa eiteagaeva
1441 vvacdaadrd qlaallaehp vtavvhsagv lddatitslt paafetvlap kvdaagnihe
1501 lagdltafvl fssvagtaga agggnyaaan aaldslaarr raaglpatsl awgpwsatgg
1561 mtgeltdadi arlaragtpa lepegrelf daalaadrat vvpvrldlav lrargevpaf
1621 lrglvrgpar rtaaadtagp gsgvaglwrg ldaadrdaav lalvrdevaa vlghgsgael
1681 dpdraftdlg fdsltavelr nriasttglr lpttlvfdyp ttsalaghli satvggdgpa
1741 rpvtpvlatg ddpvvivgma crypggvssp ediwrlvtdg gdaisgfptd rgwdletihd
1801 pdpdrrgtty asggflhsa pefdpgffgm sprealatda cgrlliessw eaferagidp
1861 rtlrgsatgv faglmynqyg silargdfeg lggsgtapsv asgrvayalg legpavtidt
1921 acssslvamh waagalrsge cslaiaggvt vmstpaaiie fsrqrglspd grcrafsdda
1981 dgvgwsegvg mlvlerrsda lrnghgilav lrgsavnsdg asngltapng psgqrviraa
2041 lagagigtad vdvveahgtg ttlgdpieaq aliaaygqdr etplylgsvk snightgaaa
2101 gvagvikmve amrhgvlpat lhastpsshv dwdagevell teplpwdidg rarragvssf
2161 gisgtnahli leapepaqlp apgtalpgta lpdtalpaap lpivvsgrtp aalrdqaarl
2221 srhldakpdt dlgdvaasli gtrtafehra avaaedhdgl rraldalatg aaatglvegt
2281 ptggrtaflf agggsqrpgm grelyarfga yaaafdavaa hlpaevidaa lgddadaltr
2341 tghagpgifa levalyrlve swgivpdrla ghsigelaaa hvagllslpd acalvsarar
2401 lmgalpagga mvavaasede vvphlidgva iaavngpssv vvsgaeaeve avvarfadrr
2461 tkrlrtshaf hsplmapmld efrtvveglis faapripvvs tvargadltd pgywvehvra
2521 tvrfadaaaa laddgvttal elgpdgvlca lvesaapdri aaapvlrpdg petrtvvaal
2581 ghlwvhgvdi patpggaagp arrvdlptya fghehfwpdv paagaatdgd gsadqalwga
2641 vergddteva aligltddrh aalsallpal sswrggrhek arldrwryrt gwtsrrvtag
2701 arldgtwllv raddpaggar atevadalra agaevadlvl daactdsaet aarlsarpae
```

Figure 18 (Continued)

```
2761  ltgivslipl  aerpaahrpg  vplglaltga  lvqalaaies  atplwtltag  avrtgpadpa
2821  dpaphtdqaa  vwglgrvaal  ehpriwgglv  dlpaephpna  ldrlaavltg  pagedqvalr
2881  agtawgrrly  rhpvdalppe  taftvsgsvl  vtggtgalgg  evarllarsg  arhlvltgrr
2941  gpdapgaadl  aaeleglgas  vhvaacdvtd  adavadllaa  vpaehpltgv  vhvagigqas
3001  tledtgpaef  drvyaakvtg  arvldnllgd  reidlfvlfs  slagvwgsrg  qaayaagnaa
3061  ldalaeerra  rglvatsvaw  gpwadagmat  ddavaadlar  aglralppap  avtelrralv
3121  qddtcvtvad  vdwqryapvf  taarasalfd  plddvaaldr  apddaaggel  arrlrdldga
3181  aqqrllldlv  raeaaavlgh  gtadavaatr  sfrdaglds1  tavelrkrlv  gltglalpat
3241  lafdhsspsa  laehlreqll  gltdaggpva  attavddepi  aligmglrfp  ggvatpeqfw
3301  dllsggvdat  gefptdrgwd  adglhdpqpd  rpgrtyttrg  gflhdaaefd  paffglspre
3361  alsmdpqgrl  llqtgweafe  raglpatlr  gsrtgtfvgs  sfqdygagaa  agngaseghm
3421  vtgtipsvls  grlsylfqle  gpavtvdtac  sssmvaihla  cqslrsgest  lalvggatvm
3481  atpapfivafs  rqralaadgr  ckafgsgadg  mslgeqvavl  lveklsdara  nghevlavvr
3541  gsavnqdgas  ngltapngps  qqrvlrgala  nagvepgevt  aleahgtgtp  lgdpleaqal
3601  matygldrdp  qrplligsvk  snightqsaa  gvagvlkmvl  amrygllppt  lhagepsaql
3661  dwspggvalv  deptewpegs  rragvssfgl  sgtnahvlle  egdrvparae  qvtvdaqdas
3721  adalepdapa  patpaalpfl  lsargaeplr  draaalaslI  gaadapapad  vafslattra
3781  qmvdravvvg  tgtdepaera  ralaagepaa  glvtgtadvd  grtvfvfpgg  gaqwagmgae
3841  laaaspvfaa  rldecaaals  phvdwvirdv  ltgaegtptl  ervdvvqpas  favmvslaav
3901  waahgvtpda  vlghscgela  aavvsgalsl  ddgarvvalr  sralaehlsg  agammsvalp
3961  adevrallae  hpgelsvaav  ngprsvvvcg  epdavtalge  qlqarevrar  rlavqyashs
4021  ayveaveepv  raalapltpv  assvpflstv  tgdwldtttm  dagywyenlr  revrfapavr
4081  alleqghrrf  lelsphpvlt  lglsetveel  gadlggpalv  sgtlrrdegg  pdrvltalag
4141  awvrgvdvdw  apaveggrrv  alptypfrre  hlwalaepva  tlresdaaev  afwdavdaqd
4201  ldtlssdldl  dagtdgvsla  aviptladwr  rrhrerdtid  awryrtvwkp  lpntapgtle
4261  gtwllvgtgd  tgstgadgav  vrtlrehgae  vryveldptg  tdraelaarl  gsgpvagvls
4321  llaaderpla  egtadegpsl  trgvaltval  lgalgdagvt  aplwcvttga  astgradpvt
4381  aplqalvqgv  vwtaalehpe  rvggtvdlpa  elderaaarl  agvlagytge  dqlalrcsgv
4441  farrvvraap  gdaaggpgwt  prgttlltgg  tgtlaphiar  wlarrgaehl  vltsrrgpda
4501  pgaaqllael  aelgteaemv  acdlgcrdsv  aglleglrae  grtvrtvlht  avsltlatid
4561  etgpegvadv  lrakvdgarh  ldelldddql  dafvlfssta  gmwgsgahaa  yvagnaylaa
4621  laegrrargv  patalswglw  addrdlgrvd  adqllrsglv  fmdpatalag  laralderdt
4681  vlavadldwe  ryhpvftavr  estlfselpe  mrrpaaapep  aaaaggala  trlaglspad
```

Figure 18 (Continued)

```
4741  tdrvlvdivr  aeaatalgls  gpselgerta  frdvgfdslt  avelrnrlaa  atgltlpttt
4801  vfdhpnpval  aaflrsmvtg  dtatpptgpv  paaavddepv  aivamscryp  ggvgspeqlw
4861  dlvtggvdav  sgfpadrgwd  aeaifdpdpd  hpgttystqg  gflhdvadfd  adffgispre
4921  alsmdpggrl  iletaweafe  ragvdpatlr  gsttgtfvga  syqdysagag  eggseghmvt
4981  gaissilsgr  vayllglegp  aitldtacss  slvalhiacr  svisgessla  laggvsvmst
5041  pdafigfsrq  ramavdgrck  aysdsadgmt  laegvlvlv   erlsearrlq  hpvlavirgs
5101  ainsdgasng  ltapngpagq  rvigaalada  gltpaeidvv  eghgtgtalg  dpieaqalla
5161  tyggdrehpl  llgsvksnig  htqmasgiag  viktvlamrh  gvvprtlhvd  rpsthvdwsa
5221  geitlardef  swprtgrprr  aavssfglsg  tnahtvlega  pdeaedvtep  aqvcvpvivs
5281  grsrealkag  aaalrerlae  gvhptdlays  latsrglfsh  raavvtggpd  sdpdaldral
5341  saladdrpdp  alirndtaga  gpargglavv  ftgggsqrpg  agrelyrafp  afadaldeil
5401  arfdteldrp  lrevmfiaedg  spdaalidrt  gytqpalfai  evalfrives  wgvhpdqvag
5461  hsigelaaah  vagvlsldda  ctlvaargrl  mealppsgtm  iaveasedev  tplltdgvai
5521  aavngpravv  vsgdadgtra  vaaqlaaggr  rtreltvsha  fhsplmdpml  aeftalasrl
5581  rfhapriplv  sdltgepvda  eavttaqywa  dhvrgavrfa  dvvrglvaag  agavlelgpd
5641  avltamardt  ldadglgadv  alvpslrrdr  peaaaltaal  aglvvhgaqt  elgaffagtg
5701  arrvdlptya  frrrfwpep   taagatptgt  tdpvdaefwa  aiehadldtl  ateleldgtt
5761  lgtvvpaiss  wrrrterna   vdqwrhrvtw  aplqssrdav  vdgtwllvgt  pdtapladal
5821  agvlggrtvr  fettaersd   laagltarla  eaaapvtgvv  sllattpgev  ttaagpvpag
5881  lvattlliga  lgdagltapl  waltrgavst  grsdplrspe  qaavwglgrv  aalehpdrwg
5941  gladlpgdas  asdpsvlrrl  agalaatpgs  gedqlavrts  gvlgrrlsta  pdttraadgv
6001  dladlagstv  lvtggtggig  arlarqlaga  gvahlllvsr  rgpdapgadp  lraeltalga
6061  gvtlvaadva  drdamaqvla  gapadaplra  vfhtagvvdd  gvldgltper  lgtvlrakag
6121  avavldelta  dhdlaafvlf  ssvagtigaa  ggnyaaana   vldaaavrr   aagrpatsva
6181  wgpwdetgmv  acdgvarrv   arggihpmap  eralgalwta  lahgdttvvv  advdwsrfap
6241  vlsasrpapl  vadlpqvrai  aptaveagpa  apdlvrtlaa  rpdaeragvv  aelvtatvag
6301  vlghgdpsai  tadraftdlg  mdslttvelr  nalgaatgit  lpttvvfdhp  tpgalaahll
6361  selrlgepaa  avpahraasa  gtghdpdcpv  vivglgcryp  ggvtspeelw  dlvdagrdai
6421  tgfpadrgwd  leslaaggsd  tghggflhdv  adfdagffgi  sprealamdp  qgrllletaw
6481  eaceragldp  rslrgadagv  fvgtngqdyp  qmlrraradv  aghvatgnta  svlsgrlsyv
6541  lglegpavtv  dtacsaslva  lqwgaaalrs  gecslvfagg  vsvmagpdsf  refstqsgla
6601  pdgrckafigd  gadgtawseg  agvlvlerls  darrhghpvw  avvrggalng  dgasngltap
6661  sgpaqgrvlr  taladaglgp  advdaveahg  tgttlgdple  agalmatyga  drteplrlga
```

Figure 18 (Continued)

```
6721 lksnighsqa aagvggvikm vmamrhatlp rtihaetpss hvdwaagavs liveatpwpe
6781 rdrprragvs afgvsgtnah viveqapaea eaeapaaepv ghvpwvvsga graaldqla
6841 rldghpgspv dvgwslatgr tafrhravll tdgdttteva rgtattggrl aalftgggsq
6901 rpgmgrelya rfpvfadafd avcahldtel drplrdvvwg eepgeithtg yaqpalfaie
6961 valhrilesw gvvpdvlagh svgelaaahv agvfsladac tlvaargrim qalptggamv
7021 algasedevt phltggvaia avngptsvvv sgteaeveav varfadrtt rlrvshafhs
7081 plmcpmlddf rrvvqglela eptrpvital agttgadmag pdywvrhvre pvrfadavag
7141 lvaagatgyl elgpdgplsa maapmidcpd vvcvpalirrd rdevatitta varlhvtgvp
7201 vdwarwfdgt garrvdlpty afqrsrfwpe papadaagtd pvdaafwdav ergdleslag
7261 tlhvgddtls amvpalsawr rdrrertaad gliyattwrg itdreitdra tpeqaprvll
7321 lvpsgtgshd hlehldairv evgpdgdltg aetdvdvvis lldtapeill aaldragvda
7381 plwcatrgav avdhteaptd ldaaarwgaa rttartaper wggmididlt pdldatdaaa
7441 laealtghhg delavrggrv larrivradg ttrpwtptgt vlvtgpadgl ggriarrvaa
7501 rgaervllld pagpdtpaav tlheeigvtv vatraadysa drapafdgdt ptavvhaepa
7561 grsavdgala ldaalpdvda fvlcttiaat wgvrgqdada etgaaytaia erraargasg
7621 talafaawsg ivensmaahl rlngiptldp dralsalgaa vaagtsvtva dvdwatfaps
7681 fapgriaali delpearrai tdtstapagd aelsarlagl taeggaevvl divraeaahv
7741 lghdgpaave pdlpftdlgf dsltavdlrn ritaatgltl patlvfdhpt pdalaeqlrs
7801 eltgqrsava dtsvtvacad dpvvivgmsc rypgvrspe dlwrliteet davgglpvdr
7861 gwdldrlaag rgvsraggfl hdvadfdpgf fgispreamv mdpggrivle aaqeaferag
7921 idpstlrgsd tgvfvgggtg dyrppsqgeg hsataqsasl isgrlsytfg lgqpavtvdt
7981 acsssivalh laagavrage csialaggvt vmstpvglve fgemgalspd grckafsdsa
8041 dgtgwsegvg llvverlsqa rlrghevlav lrgsatngdg asngltapng gagqrvirrg
8101 lavagispae vdaveahgtg ttlgdpieag allatygqdr tepllgsvk snightgsas
8161 gvagvikmvl amqhgtlpat ihvdrpsshv dwsagsvsil trarpwpetg rprraavssf
8221 gasgtnahai legapaveap aaprtsrtvv pvpvsgrsaa alraqaqrlr ehvartgdgv
8281 adiafsaatt raafehrgav vaathdellq glaalaegrr gpgvvddrav rrgrtaflfa
8341 gggsqrlgmg rqiherlpaf aaafdevcdr laghtdvdvr avvhgtdada ldrtgnaqpa
8401 lfalevalyr lleswgvtpa fvaghsvgel aaahvagvis lddacalvaa rgrimqalpt
8461 ggamvavsat eeevtplita gvalaavngp tsivvsgdad qveavvaplir eggrrtrrls
8521 vshafhsplm dpitedfrav casltfhaps ipvvstltgr iaedgelgdp eywvrharha
8581 vrfadavttl agrgvtvfge lgpdstlaal aresipdgdt atvaglirrd rdeettltg
8641 latlaaggag vdwpaiffagt garrvalpty afqharifwpe pvapataapa gaagddsafw
```

Figure 18 (Continued)

```
8701 dvvergdlag lagtlgvehg elsavlpalg ewrrrhrers vtdgwrqrit wtpltdlpra
8761 rpsgtwlavl paglagdawv ratldalgtg vvplevgagt praelaaqis phvgavsgvl
8821 sllaladpep davvpagtta tatlvqalgd agipapiwav trgavsvaat eaparpeqag
8881 vwglgrvaal ehpdrwgglv dlpeaagdid davaarlaai laghehedqv airasaafgr
8941 rlvaagdsdd dtaweptgtv litggtgalg aqvarhiatt rsddgraphl llagrrgpda
9001 pgaddlvael tglgaqvtva acdvadrtql talldgvgde rpltavvhta gvlddgvldg
9061 ltperfaavf rskvtsalli deltgdldaf vlfasasaav gnagqanyaa anavldalae
9121 rrratgraat siswgawgga gmaagadaee vsrrtgvtpm cpdravatlr rlagghqata
9181 vvsdvdlarf vrtftaarps plirelpgya dlaattpepa gtdsgpslre klaglsparr
9241 rrtlelvcg rtadilgygg adeigpdraf rdigfdslas velrnqigaa tglslsatlv
9301 fdhatpgela dhigtelgsg sgsgpdsgsd pgpdaqeaee agirallasv plellresgl
9361 ldpvlalags pthghaggng haaadghtag ngnghaagng ngnghaggng haaahgpdgd
9421 dgaiddmaid gmaiddlvra aldnehdedr sar
```

```
1 mttsqdkliad alrasmkege rlrrenrrla gaasepiavl gmgcrypggv nspediadlv
61 esgrdavtgf ptdrgwdlsa lqdggvderg tsvsqqggfl dgvadfdpgf fgispreart
121 mdpgqrllle vsweaierag idptslrgtp tgvytgtngq dvaylvvrsl adadgdvgtg
181 laasatsgrl sytfglegpa vtvdtacsss lvalhlaaha lragecslal aggvnvmstp
241 gsllefsrgg glaadgrcka fsddadgtgw aegvgivivle rlsearrqh pvlavvrgsa
301 vnsdgasngf tapsgragqr viraalaaag lraadvdvve ahgtgtplgd plearallat
361 ygdrdpaqpi rlgsvksnig htqaaagvag vikmvqamrr gtvpatihad tpsshvcwns
421 gavrlltdae pwpetgrarr aavssfgvsg tnshvvlega paldpagdpa vdpadgpart
481 vpwllsapta sglraqagri hraldgaaaa asdvgyslat srtrifphria vvgddtsala
541 galsgwldga paaaggtarr daqlgvlfag cgsgrlgmgr elharfpvfa rafdevcahl
601 dpavgevmwg dcagalndtg vaglalfale valfrlvesw gvvpdhivgh sigelaaahv
661 agvfsladaa tlvsaararlm gaipaggvmv avaateeevt plltggvsia avrgpssvvv
721 sgaesevdai vgrfadrrtk rlatshafhs plmapmmeef ravvaglefa apqipiistv
781 agrtgddvtd paywvehvra tvrfadaltt lteegvhtil eigpdttlsa laagagadia
841 vpalhpdgge etsvvtalar idtagatvdw arfftgatpv dlptyafehe rfwarggsaa
901 tdaagigltp aghpllgatv pvagtgdvvl taalstathp wladhvvgga valpgtgfle
961 lairaadevg cerveeltla apivihgaaaa thiqlrvgap addgrrdigi hsraggtdew
1021 vrhatgtlag gapaggaahp dlsgtwppeg atavdidhly atdtgvqygp vfrglraawr
1081 rgedvfadva lpdevddaga fgihpalfda alhairsahd dedtalipss wsgvtlaasg
```

5    ANG09098.    SelJ
     1

Figure 18 (Continued)

|  |  |  |
|---|---|---|
|  |  | 1141 asalrvrigr rdgcevtlda adpdggpvis veslalrhad patatarrnd lsglfrldwv<br>1201 tgaavpgrap trvtvlgpdp idlvpaltga ghhvahrdds adagpadaae tadtgpvlvp<br>1261 laggpagsgd tralvaaalr rlqdivsgdg agrvvlvtrg avatdpgddv tdpaaaavwg<br>1321 larsaqaehp drvlivdlds apesaaripe ivaaidpeep qvavragvpr pariaplits<br>1381 talvppagtp wrldatgggn adglalvpcs evtepltgrd vrvrvhaagl gprdvrtalg<br>1441 ahrgdarrlg seaagvvtdv gllivtdlrpg drvagmlsgg fgpvgvvder llaripdrws<br>1501 feeaaavpsa fltayyalvd lagvqagqkv lvhngagavg maaielahhl gaevyatagp<br>1561 gtqdilrglg vaddhiaspr dttfaeslag agidvvihap tdgfadasrg lpvpggqvld<br>1621 lgptddpvgg pgttdaasal dtvdpdriht mletvlglia dgtldplprv awdvrrapea<br>1681 frfvtragha gavvlrvpre qdpqgtvlit gglgglgael arhlsvrgas rlllagrgp<br>1741 dtpgaleiaa elaahgtdar vvacdlaepg aaadivagvd pdhpltavvh aagvlddgvl<br>1801 eamtpkridt vlapkvdaaw elhratehld laafvlysst agvigspqgs nyaaanagld<br>1861 alaahrratg ipavslawgp weqgagmtat lgergtrrig aagmpplpve rglalfdaal<br>1921 gsdealilpl gtppsgggap sgpvppvlrn lvrggrrsaa agsaasapdl aarladlpet<br>1981 drraaltdlv rtaaaavlgh aspdavdadr efrligvdsl tavelrnrvg aatglrlptt<br>2041 lvfdqptpva vaehlaellp tgpgspdggg svldrlanfe aamgaaapda deradvtarl<br>2101 rrmlarweta padgvgdrls gasttdlfsf idnelgrsag a |
| 6 | ALE82581.<br>1 | SelSI | 1 mtispqvdvv dvadgrvtgt dryldlmkkv ltnviypdga yahirqiddp dstempipve<br>61 glgerilefd adardggrdw ptvahtmvgr rridnvhecl eriladdvpg dvietgvwrg<br>121 gvcifmrafl vahgctdrtv wvadsfaglp pagdrdpdpv aamghdvatv nermlavdla<br>181 qvqenfdryg llddqvrflp gwfsdtlpta pierlsilrl dgdwydstmd alvnlyprls<br>241 sggfviiddy cvpgcadavt dyraqhgida elididrmgv ywrkp |
| 7 | ALE82582.<br>1 | SelSII | 1 meitetavpg afritptqip drrglfyeaw risdveaalg rpfrvagtnf svshrntlrg<br>61 ihgttlppgg aklvtcvrga aldvvvdlrv gsptfgavdt tlqeagsgvg vylgdglgha<br>121 flaltddtcm nylcdteyvp gtmidiqald pdiaipwnlt edpirsdkda aaptlseave<br>181 lglltayrep agt |
| 8 | ALE82583.<br>1 | SelSIII | 1 mkgivlaggs gsrlhpitla vskqlmpvyn kpmiyyplsv lmlagirdil littprdvpa<br>61 fgallgdgsh lglsltygeq peprglaeaf ligadhigdd pvalilgdnl fhgpgfapll<br>121 qrtvdevkga vlfgypvadp hrygigeida dgvlvsieek pasprsnqav tglylydndv<br>181 veiagsvrps argeleitdv nrvylergra rminigrgfa wldtgtvpsl ldaggfvrtl |

Figure 18 (Continued)

| | | |
|---|---|---|
| 9 | ALE82584.1 SelSIV | 241 eergqthiac leeialrmgf idveqcrvlg erlersgygr yvletveavr s<br>1 maltgalpgi epdelvvldk ltyagnranl apvsdddrlr lvigdvcdpe lvaretagtd<br>61 lvvhfaaesh vdrsiagsad fvttnvvgtq vliqaavaar vervvhvstd evygsvgega<br>121 aaedhplipn spyaaskass dllarafhrt hglsvsttrc snnygpyqfp ekviplfvtn<br>181 liegrtvply gdglhvrdwl hvddhcrgia lvanggrdge vynigggtel snrdltdrll<br>241 aatgrdssav rrvtdrlghd rrycvditri sdelgyrpqv gfddglaatv dwyrtrrdww<br>301 epirtsvsga a |
| 10 | ALE82585.1 SelSV | 1 mrvlfaissw tghyfpmvpl awamraaghd vrvlcrpsdg advtaaglip vpaldglgldll<br>61 rgarlinvms llggtwpyrq ppphpdtgea mdpagfdiaa whaenmpamv assragtdaa<br>121 vafgrswapd lvvhdqisle gplvsavtga psvlhlwgpa gtadafapvg gegaglpqdl<br>181 sdaftrygag tishdlachv ldpcppplrt avagrdagir yvpyngpgaa pldipepdgr<br>241 rprvcviwgr svtrtfgpvv nrlpqavraa adlgaevlil arpedardag pipdgvrpfh<br>301 evplslvlpg cdavvhyaga gsvmtaltag vpqlsvpcgf dqpmvaeris atgaglhvhn<br>361 ldadaatigg alekligpps yadaardlaq rcaampspae vvadlealaa r |
| 11 | ALE82586.1 SelSVI | 1 madrkalpaa tslgeielva vasrtrqraa efaerhggrp tgyqelidap dvdavvvstp<br>61 aalhhrwtaa alragkhvlc ekpltdnlpd teelaelaea rdlvlrenfa flhhpqhtvv<br>121 adilraqglg slrtfaatfg ipelpaddir hspelgggal ldvgvypvra aqgilegplt<br>181 vvaatsqvdd rfgvdvsghv ilhsadgvva dfdfgfrhry rnryrlwtst asleidrfft<br>241 pppdhrslir leeqhttdtv vvepcdqfre slrsfahaat agpdhrdeqa wtaaaretar<br>301 llgeirrvav rlpdptrstv g |
| 12 | ALE82587.1 SelSVII | 1 mspappalrt adrtlprrla rsalwdaaga ararewiaer naahrhdvrr ipfdelrswa<br>61 fdpatqnirh dtgrffsveg iqvhtdhgpv rswsqpllnq peigilqlim aeidgvlhcl<br>121 lqaktepgnv ngvqlsptvg atrsnytgvh agnavpyley frnpgagrvl sdvigseggs<br>181 wfyrkrnrnm vveveepfea hedfrwiplg qvhelcavdn ivnmdtrtvl agmptgfegm<br>241 agtgsgglad alarscvass gglhtdaevl switdrqsgh eirteliplh dvahwrtpd<br>301 rlrhdpesff sviavavtat srevgswtqp llephgvgrv allvarfggv lbalmharve<br>361 pgyleavela ptvqfapety rglglaapaf ldvveeaqpg ervlfdaels eeggrfhhar<br>421 nryqliievdp vlddrttpdh rwitvaqlng llihnnyvnv qarsliaclr gla |

Figure 18 (Continued)

| | | SelA |
|---|---|---|
| 13 | ALE82588.1 | 1 mtqtpatpvd dqvaivgmac rapggvrspg dlreitlsrg eafsafptdr gwdlsalsgd<br>61 qpvangrggf lddaagfdag ffgispreav amdpqqrgll evswealera aidprtlrgt<br>121 dagvfvgihg qdyavaahgs rddlvghamt gmsgavasgr layvlgcggp avtldtasss<br>181 slvalhyavr slrsgecsla laggasvmst esgflgygrg gglspsgrpv pfsddadgtv<br>241 wgegvglivl erladarrhg hpvlavvrgt avnqdgasdg ltvpsgaage rvvaraldda<br>301 glrpadvdvv eahgtgtrvg dpvevtalra aygagrerpl llgsvkshvg hlqaaagvis<br>361 viatvlairt gvipglrrlg tpttradwsg elieplartt dwpdtgrprr agvssfgvsg<br>421 tnahvvlega agpgpvdgag apdddrlvpw avsartatal qtaveqirga aagrsrrdvg<br>481 htlavgratf dhramllagp qgtvevargr vdgetallf ggraapagag relaerfpvv<br>541 ataldgvhah rhsdggdeta tfalqvalyr lweswgvtpr rvagsavgev aaahvagvls<br>601 ladataliea rallgerpad raagpdpeld rfratfaglr fappripvvc gaagraatad<br>661 eladpdrwvp rpgpvadpva aarvihadgv etfleigpda tasaavrtal gervttvptl<br>721 rgggdevtsv italgrihva gtpvdltaav gdgrrvelpg ypfehrtywp apgdggrtga<br>781 tghpllgard dlagagglif sgrvparahp wladhrpggg gatlpvpalv elvlraadev<br>841 gcdriddlra gcplpvdehg tvelqtwlga anagrrvvtv hsrtagtgqp gaegsgwelr<br>901 aratvsrgap aaggdgsdlp dgavpltpaa lgerldgagf gpdlaglvga gwelddtwv<br>961 evtlppdvdr agfglhpall taalgavgrr gdgsevparw rdvalhaega savrvritrt<br>1021 dgstlrleav dvagapvltv gaielgrgrt vpvpsavpda pdrparpvrr aaalpgasga<br>1081 gatgvdvval tgphrrrglr mlvraeaadv lglsgpdevl grarfkeggf esltgaelvn<br>1141 rmaartglal qpglvfdhpt pdilaghlad eldarddgpa pdavpdpapg pgpepgspdd<br>1201 pldseladas ldrlmdilda elgva |

| | | SelB |
|---|---|---|
| 14 | ALE82589.1 | 1 mtdaeqnagt qchdgaatap qdkvvcylrk vttdlirrtr rldeletren epmavvgmac<br>61 rypggvrspe qlwdlvasga daitgfptdr gwdrqalagg gagssatadg gfldgvgdfd<br>121 aeffgispre alamdpqqrl llevsweale ragiaptslr dsatgvfvgs yhwghsqgpa<br>181 dpevdlgght ltgtaasvas grisytiglr gpaltvdtac ssslvaihla arslragess<br>241 lalvggvtvm sdpslfvefs rqggispdgr crafgegadg tgwaegagvl vierlsdarr<br>301 hgheviavvr gsavnqdgas ngitapngps qraligaals aaglrpgdvd vveahgtgts<br>361 lgdpieagal latygrdreq plwlgslksn ightqaaagv ggviknvmal qrgmlpatlh<br>421 aetpssrvdw sagavrllte pvawepgerp rragvssfgv sgtnahaile eppaadgedt<br>481 sdrpdalttc awsfsargpe slgaqaagla aritdsdpyd vayslartra sledravvlg |

Figure 18 (Continued)

```
 541  sdreellaga  ravaagepsa  avvtgradld  gqtvfvfpgq  gaqwagmgae  lldtspvfae
 601  afdaaaaalr  phvgfsphdv  vrqvpgapgl  davdvvqpls  favmvalaav  wrhhgvhpda
 661  vlghsqgeia  aavvagalsl  ddgarvvalr  araigehlag  aggmlsvpls  rdevvtrigs
 721  rstlsvaaen  gpravvvsgs  aetvgglhae  lvadgvrarm  lavdyashsa  hvealeqrll
 781  ddlagltpgp  aavpmlstvt  gewldggeld  agywyrnlrr  tvgfgpavet  llegghrafi
 841  evgphpvlsg  avadsarerg  tdvlvtgtlr  rgrggpaqll  tsfaeahvrg  ldvdwaslfp
 901  ggrrvalpty  pfrrrifwag  patpesaaad  pagvdpgeqa  fwaavedgdv  aaltsslhad
 961  adslaavlpa  lsdwrrtnre  ratldswsyr  vewrpvpaag  tptlsgdwlv  vttddcltdtg
1021  ddvvaaltaa  gaavhpvvld  gacdgraaaa  ellaaatgva  saagvvslla  aderadpdhp
1081  gstvglsrtl  alvqalgdlg  vhaplwfltr  daartgpsdr  lthplqalvh  glawtaaleh
1141  pdriggtvdl  ppgaldahtg  prlavalsga  pgedqlavrp  aglytrrlvr  tvpgaastgg
1201  perewaphgt  tlvtgaggal  apdlarwlsr  cgaedlvlvg  rrgpdapgta  elveelarlg
1261  tavrveaccv  gcrdavaall  aglaeaghvv  rhvvhavavm  elesvdatda  aevanvlrgk
1321  vcgarhldel  ldggsldtfv  lytstagmwg  sgrhaayaag  naylsalaeh  rrarglpata
1381  vhwgkwpdav  gsteeatdqph rvrrtgleli  dpdtamaglr  rvldhdehvi  glmavnwpry
1441  hdvftsgrpt  tlfdelpevr  lrntaadaga  pavsehgdgr  llgrlrplpa  aegerlllem
1501  vraevaavlg  hgsgaevpel  rafrdigfds  vtavdlrnrv  aaatganppa  tmvfdhptpl
1561  alarhirtel  lggestapaa  papgaaasdd  plavvamscr  lpggvasped  lwclvadgld
1621  visdfpddrg  wdadalrdpd  pdapgrtyst  vggflhdate  fdagflgisp  realsmcpqq
1681  rlllettwev  feragidpaa  lrgsatgafv  gagagpypha  vgdagethmm  tgtaasvlsg
1741  risylfglег  psvtvdtacs  ssivalhlac  rslrsgessl  alaagatvmp  tpepfvgfsr
1801  gralatdgrc  kafadgadgm  slaegvgvvl  lerlsdarrh  ghrvlalvrg  sainsdgasn
1861  gltapngpsq  qrviraalad  agitpdgvda  veahgtgtal  gdpleaqail  gtygrdrdpd
1921  rpllgslks   nightgaaag  lagviktvla  fghdelprtl  hagtpssrvd  wsagavrlld
1981  epspwpqaer  prraavsafg  lsgtnahavl  eqappepvaa  gpeatvvapg  gdapvhdtpt
2041  lwplsarsae  alcaqaarlr  asfldghrpdg pgraeptgdp  arrpddvgws  larlragfeh
2101  ravvlgqdld  tllaglesva  agetapgvqr  gtaaegdrrp  vfvfpgqgsq  wggmgrella
2161  sspvfiratia dceralsphv  dwsltevlag  dadpalsarv  dvvqpalfat  mvalaalwra
2221  ygvepaavvg  hsqgelaaah  vagalltdda  amlvalrsra  lltlsgaggm  tsvaagpdrv
2281  aellapwsda  ltvaavngps  stvvsgdaaa  ldelaahcaa  egvrsrrvdv  dyashgthve
2341  avrdelaavl  agvrpvsspi  pfystvdgav  vdtagldagy  wytnlrepvr  meaatralld
2401  dgrrvlleis  phpvlgtale  etveahgadt  avalgtlrrd  dggpdrvlta  vaeahthgva
2461  vdfaavfagr  darpvdipty  afrrrywpe   elapaapapt  dgvggrfwel  vasgdgesla
```

Figure 18 (Continued)

```
2521  aelgvgsngt  rssldavlpa  lsawwdraar  rdtadgwryr  igwtrirpqs  agrpagrvll
2581  vrppgmpdle  pvreafgpgt  ttveldpiva  adraraaaal  adaavgadiv  vfllaagtps
2641  ddgevptala  atiglvqalg  digaaaplwc  vtrgavrtgp  gdttvvdpga  gsvwglgrvv
2701  alenparwgg  lidlpaepdr  rsaealaafl  aapagedqva  vrsagisarr  lihatpaadr
2761  pwttsgaalv  tgtggvgai  varwlvdrga  rhivltsrrg  pdapgaaelv  adlrergatv
2821  tvvacdaadr  aalaqvldgi  dtpgglrsvf  haagvsdgda  pvadltgeql  rallhpkapa
2881  aqhldelvgd  relqafvlfs  sgasawgsgg  qpgyaaanaw  ldalaerrqa  qgrvatsvaw
2941  gawaqagmat  dpvaharler  ggvtamdpdl  algaldttla  hapavaaita  mdwtrfadgf
3001  tsvrpspila  elaeaqevvd  tvpdaaadgv  apllgrlagl  ppaerdraml  eavrteasat
3061  lghddpaavp  agrafrdvgf  dsvtavelrn  rlrgatglrl  paslvfdfpn  prdlarhlgt
3121  lafggdaapd  gppdpdaptr  eliasipldr  lrraglidel  lrlagapedd  pheqsdehgt
3181  sldcmdgesi  lrlvseasn 1  mttdsnqyve  alrsslkene  rlrrqnealt  aaaaepiavl  gigcrfpgggv  aspedlwell
 61  drggdavsgf  ptdrgwdlet  laagsaggdg  gegrslateg  gfldvsgfd  agffgispre
121  avamdpqqri  llevtweale  ragidpsrlr  gsdagvfigt  tggdygevla  gsaddaevya
181  ttghaasvis  grisytlgie  gpavtvdtgc  ssslvamhga  mqalrarecs  laltggaaim
241  atplaftaft  aqnglaangr  ckpfadaadg  tgwgegagvl  vlarvsdarr  lghpvlavlr
301  gsaingdgas  ngltapngps  qqrviraalr  nadleptdvd  vveghgtgtt  lgdpieaqal
361  iatygrnrrq  plwlgsiksn  ightqaaagv  agvikmvlam  rhgtvpatih  veapsnvdw
421  dggvelpvt   aqpwpetgrv  rraavssfgi  sgtnahvile  qapaeapsga  qtpardaepa
481  wpvpwpvgar  dddalsdrvr  alcdpagsag  savdvgwsia  tgraafehra  vilpgptgha
541  evargvtdeg  llatvfiaggg sqrlgmgrtl herfpvfaqa fdevcahldp svrevmwgtd
601  agalndtgta  qpalfavqva  sfrlliesrgv  apdyivghsl  gelaaahvag  visvadaaql
661  vsararlmsa  lpaggvmvav  eatedevtph  ltpgvsiaav  ngpssvvvsg  aesevdavvg
721  rfadrrtkri  atshafhspl  mapmieefra  vvagitfaap  riplilstvag  rtgddvtdpg
781  ywvehvsatv  rfadavaelg  rdvgttlel  gadgtlsaiv  gqvlptatvv  pilhrdhded
841  rsaitalarv  wttgadvcwt  alipggrrvd  lptypfqrrr  ywpaparaad  agaagldave
901  hpllrsavtl  adaagvvlag  rlslatqpwl  adhevagral  lpgtafvela  vragdevgce
961  rveeltlaap  lmvpptgavg  lqvhvgaaeg  tsagpvrrpf  tvssraagav  elpwtrhaag
1021 tltggdpdag  etapfdaeaw  pppgaepvdl  dgcyerltdl  gfrygptfrg  lraawlrdge
1081 vyaevtlpgd  dpdtarfglh  pavldaacha  avyadlgpls  egglpftyeg  vtlhaagatt
1141 vrvrltrqsd  dsvsiaiadt  aggavatvgs  lvsrrtgags  pagaagagrd  pifaidwhpq
```

15  ALE82590.1  SelC

Figure 18 (Continued)

```
1201  aptaatpept avavagplpa gfdgahvavh pdidtlihdp agpsgtvlfp vvpsgadips
1261  avreatatvl talqrwlade rgdgarlivv tcggaavadg ddvdpagaav rglvrsaqae
1321  npgrfglidi erdadapata aaaalaglhg gepdlavrgg svlvprivra lpgtadpgap
1381  gwrpdgtvli tggtgglgal tarhiaaerg vtrlilisrr gpdapgaael vaelgtlgae
1441  atavavdvgd rdalarvlda vprehpvrav vhtagvvddg vigsltpdrl dtvirpkida
1501  awhlheltgd ldafvlfssv aavvgspggg nyaagnaald alaahrraag lpalslawgp
1561  wtrtvgmtaa lscdadaarva rsgmpeicvd agialldaal cqprpavapv ridlvalrag
1621  gdvphvlral vriprraaa rgevadglar rlgtlgaper dealfdlvre evarvghte
1681  agevpatrpf telgidslsa velrnrlsgv tglrlsativ fdhptprala ghlrdelfgg
1741  gteapvpvpm lpataedpvv ivgmacrypg gvsspedlwr lvtdggdais gfptdrgwdl
1801  eglydpdpdr pehthavggg flhgaggfda effgmsprea lgtdaqgril lecsweafer
1861  agidpvslrg satgvfagvm yndystilpg geheafrgng sapsvasgrv aynlqlegpa
1921  vtidtacsss lvamhwaaqa lrsgecslal aggvtvmstp stfvdfsrgr gispdgrcra
1981  fsddadgvgw segvgmvvle rlsdarrngh evlavlrgsa vnqdgasngl tapngpsqgr
2041  vimaalasag lrssdvdvve ahgtgttlgd pleaqallaa yqqdretply lgsvksnigh
2101  tqaaagvagv ikmveamrhg vlpatilhast psshvdwdag evelltepip wdidgrarra
2161  gvssfgisgt nahlileapd papvaeaadg esgvvpwpls ghtpdalcag aarladaalr
2221  erpvdigfsl attratfahr avvlahdhsd aeqalralad gtadervvtg ragtgtgvtf
2281  lfaggqaqri gmgrelyqrf rvfadafdaa cahlapavre vmwaddaeal rdtaiagpal
2341  falevalsrl leswgltper vvghsigela aahvagvlsl pdagtlvsar arlmgalpag
2401  gamvavaate devtplitag vslaavngps svvvsgvese vdavvarfad rrtkrlatsh
2461  afhspsmapm ldefrtvveg lsfaapripv vstvagrtga emaepgywvd hvaatvrfad
2521  altglgdtvt veigpdatlt alaagvapag atavpalhpe rdetgtvraa varcwsagad
2581  vdwaavltgg rrvdlptyaf qheyfwpepv praadagtvg lrpaghglid gviettdgvl
2641  ltgrisrtth pwlvdhavsg tvllpgsall dlaarageet gydrveelml taplalpegg
2701  glalrvtvga atpdgprtvv vhsrpdaaht wtsptwteha sgligkhtpp lspfaqqwpp
2761  agavpvdvdg cyqrfaddgf dygpvfrglr aawrgdelf veaalpdgtd pepfglhpal
2821  lcavlhpiae lcpddergav pfawrgvtry adgatsarar lrrvgppgavs idladaagap
2881  laavhqlelr altasrtaap drdalfrpgw ervpatvpsg ltvhaetvdg gpvgpdlaal
2941  lersgvrgad taevllldar sggtaatpdg aaharttavl arlgteasgt rrtvvltrga
3001  tdgadpaaaa vaglvrsaat ehpgrftald taidtgadal daaafaaalg rtdepqlavh
3061  dtelrvlrlt rleppadpas aerpavpwrp dmtvlvtggt gglgaqvarh lvtahgvgsl
3121  llagrrgpsa pgaaeltaei taagagvevv acdaadrdal aallarrpvd avvhaagvvd
```

Figure 18 (Continued)

```
3181  dgvleglrpd rlaavlrpkv daagnlhela gdveafvlfs slagtlgsag garyaaanaf
3241  ldglavhrha agipatsltw gpwsgaggmv gdiddaarer maragmppve pgralalfds
3301  avatgepvva pvpldpaalr arggdvpaal rgivgavrra aatavipsgl reqiaarpva
3361  errarigglv rdeiahvlgh aegsridpdr afldigfdsl tavelrnria astglglpat
3421  lvfdhptaaa lavhvhdelf gadtapepvt atatgpadgd dpvvvgmac rypggvsspe
3481  dlwrlvtdgg daisefptdr gwdlanlydp dpdhpgtstt rhggflhgag rfdaeffgms
3541  prealtttdag qrlllecswe aferagidpv slrgsatgvf agvmyhdygd llhapehegy
3601  qghgsagsia sgrvsyfigl egpavtvcta cssslvgmhl aaqalrsgec slalaggvtv
3661  matpatfvef srqrglspdg rcrafsddad gvgwsegvgm vvlerlsdar rnghevlavl
3721  rgsavnqdga sngltapngp sqqrvimaal asagirssdv dvveahgtgt tlgdpieaqa
3781  llaayggdre tplylgsvks nightqaaag vagvikmvea mrhgvlpatl hastpsshvd
3841  wsagavellt anrvwnadrp rragvssfgi sgtnahvvle apepaeavar pdtagplpwv
3901  lsartgpala aqaarlagsl ehrtdvdald vgwslatgra rfghravvla edtaaarral
3961  aafaageqhp avvegtvaag gtafllfaggg sqrlgmgrel harfpvfara fdevcahldp
4021  avgevmwgdd agalndtgva qlalfaleva lfrlveswgv vpdhlvghsi geiaaahvag
4081  vfsladaati vsararlmga ipaggvmvav aateeevtpl ltggvsiaav ngpssvvvsg
4141  aesevdalvg rfadrrtkri atshafhspl mapmmeefra vvaglefaap gipiistvag
4201  rtgddvtdpa ywvehvratv rfadavaald edgtiveigp datisgmagg ltdartvptl
4261  rtsgpdgdrd evtalfaala rlgtagadir wetaldggrt vdlptypfgh dtywpapapa
4321  nrgdagsigl sgpghpllga vvaradtdgv lltgrlstvt gpwladhvvg grvlpgtal
4381  lemavragde agccvvrelt laaplelpgg gvtvgvwlda pddagdravs ihsragetap
4441  wtvhatgllg tggtaapeti twppqgaep fdvtdrydrl aetglaygpa frgiraawrr
4501  ggdvfaeivl gegagpadgf glhpalldaa lhaagtvggt asvpfgwgdv tlhatgatal
4561  rvrlrtdapd tlsvlvadga gdpvatvgal tlrplpegap graerdlyrp vwipatdtpd
4621  tgettigvla edtavldvpg gtrhadlaea ldaapdvliv pvatgdgdla arthdatsrv
4681  ldlltrwtad ersagsrlvv ltrgavaagd gdgvvdpaaa avsglvraag aeypgrigll
4741  dldldfdadp asaaaipval agdepgrair agrvldprig rhdvtatdgt dgtdgtdgta
4801  tcgtdatggt aggtgwrrdg tvlitggtgg lgaltarhla arhdvrhlll lsrrgpdapg
4861  aadltaelee lgarvtvvaa daadraaltr vldaipaehp ltavvhtagv lddgvlaslt
4921  pgrlrtvlrp kvdaawnlhe laadiegfvl fssvagtlga agganyaaan afldalatvr
4981  raagrpalsl awgpwepvgg mtgtltdadr armsrsglpp mpvargiell daalgeaapv
5041  etapvllpvp fdldalrgrp eipamlrglv rapsarrsaa agssgasgtl gdrlaalgea
5101  drhdhvlglv rdevaavlgh asaasvdpar aftdlglfdsl tavelrnrlt tvtglrlpst
```

Figure 18 (Continued)

```
5161 lvfdhpsaga lathllgelv ghvaatpvgs ptavdrddpv vivgmacryp ggvsspedlw
5221 rlvtdggdai sgfptdrgwd leglydpdpd rpekthavgg gflhgagfd aeffgmspre
5281 algtdacqri llecsweafe ragidpvslr gsatgvfagv myndystllp ggeheafrgn
5341 gsapsvasgr vayniglegp avtidtacss slvamhwaaq alrsgecsla laggvtvmst
5401 pstfvdfsrq rglspdgrcr afsddadgvg wsegvgmvvl erisdarrng hevlavirgs
5461 avngdgasng itapngpsqq rvimaalasa glrssdvdvv eahgtgttlq dpieaqalla
5521 ayggdretpl ylgsvksnig htqaaagvag vikmveamrh gvlpatihas tpsshvdwda
5581 geveltepi pwdidgrarr agvssfgisg tnahlvieap epsaapvapa gaaqddpgdl
5641 vpwvlsgrtr ealqaqaaal rtaapdgpra dvgfslattr safehravvl atsrdealaa
5701 lealargdrd ervvdgrtaa ggtaflfagg gsqrlgmgre lharfpvfae afdaacaqld
5761 pavrevmwad daealrdtai aqpaifalev alfriveswg vvpdhlvghs igeiaaahva
5821 gvfsladaat lvsararlmg alpaggvmva vaateeevtp lltggvsiaa vngpssvvvs
5881 gaesevdavv arfadrrtkr lrtshafhsp lmapmmeefr avvglefaa peipvvstva
5941 grtgaemtdp sywvehvsat vrfadavtal dedgvttlve lgpdttital tagaltgeqi
6001 svptlragea epatllrava tvhvrgrtvd waaqipgarr velptyafrh trfwptasaa
6061 rsgdatslgl arpghpllga vmdracadgv vltgrlspat qpwladhtvg grvllpgtal
6121 lemvvragde vgcdlvhdlt laapveiphd ravglqvvvg epdgdgrrtv dvhsrgegdr
6181 twtrhatgvl aggasagwsp dvwppagavp lgldgcydrf aeagfgygpa frglraawsd
6241 gtttfaeval pegtgadrfg lhpalldaal haamldtgdd daaglpfswq gaalyasgas
6301 alrvclgrda gggltidatd pagapvvsvg slqvravpaq ahtgavprda lfrptwaplp
6361 dapahtgsvt vleaglidelg agidagsaap etvllpvhgt gdvptsahel satvlaavqt
6421 wladerlars rlvlltrgav atgigdtcgd vtdpaaaaar glvrsaraeh pvrfglldld
6481 patdtgvpdg lpfdtepdla vrsgtvyalr larvpdtard daatgwdpdg tvlvtggtgg
6541 lgravarhlv tdrgarhlll asrrgpaadg vdalveelta hgarvgvvac dladpaaata
6601 lvdgvdpehp lvavvhtagv lddgvvdalt pqrvervlrp kvdaawalhe atrgtdlqgf
6661 vlfssvagta gsaqqanyaa gnafldalag yrrasglagg ggmaaaldda
6721 nrarmaragm pplstaegla lfdaalldadd alltpvrldl avlreraevp silrglvrap
6781 argaaasapd vadlagrlag ldedgrrqvl ldvvathvag tlghtdlsgi gpddefgelg
6841 fqsltavefr nrlgaatgla lpatlvfdhp tpgalaghlq tlvtpagadg adalldelae
6901 lerrfgavev deaahervga rleairsrwa girpttdeaa padsgtaefd fdtasddcmf
6961 alldsqlgtt
```

Figure 18 (Continued)

| | | |
|---|---|---|
| 16 | CP011868.1 | SelK |

```
mtdeeklvdy lkwvtadihe arrrlaevea grqepvaivg macrfpggig spediwelvs
tggdaisgfp adrgwdmdal rdgrsatdgg gflegagdfd pgffdispre avamdpqqrl
llevsweale ragvdprglr gsrtgvfvgt sgqdyihial aadvdmegha stglaasvms
grisfalglq gpaltvdtac ssslvalhla arslrdgecs laiaggvtvm stsanfssfs
rgglapdgr cktfadaadg tawsegvgvi iverladaer ighpvlavvr gsavnqdgas
ngltapngps qqrvirdala agglgpadvd vveahgtgtr lgdpleaqav latygaerer
paligsvksn lghtqaaagv aglikmvgai rhgtvpatlh vdrpsshvdw tqgavelate
sqpwpetgre rraavssfgi sgtnahvive qapqtgpdpe adtgtpvgl vpwvvsartp
deldaqivri galaapgqps atdvgfalat grtlfdhrav laptaddvre largsaahat
gsvgvlfsgq gsqlqmqre laarfpvfae afdavcaeld pligrplrev vwqddesvlq
qtgwaqpalf avevalyrlv eswgvrpgmi aghsvgeisa ahvagvislp daarlvaarg
rlmqalpagg vmvsvrated evtplleqvv svaaintpga vvisgaedav davlagiggr
rstrlsvsha fhsplmdpml edifraalspi vfgeptipvi sdvtgepatd lgadywvrhv
retvrfadgv ramsaagvtt fvevgpggvl aaaaaaqsipa satvvpllrr drseeesava
alagmhsvgv avdwpalfag tgarwdipt ypfrherywp rpattghpll gppvpvagtg
etvltghlsv rshpwladhv vgghvimpga atvelvnrag davgrhried ltiivapvlp
drdavtvqvr vgepdghdrc eitvharpdg gewmvhavgs lagdpvdlgf dggvwppaga
tevslegfye ryaetglqyg pafrgirsvy trgdevfaev vapesaatan gyglhpalid
avlhanvfig rdggalpfa wngvslhrsg asvlrarirp gtgdgvelav tdaegdpvis
vaslvvraas gagagtaggl sgirwvpqta aepatgtrwa vvggdeldlg yailhrageav
tayadtigga vgedgslpdv flvplgtaga geddadvpat ahtlthrvla llqewqstpa
laatrlvfvt cgavsvdaep lrdpaaaavw glvraaqvel lgakilladi ddafasasvl
paligadeqg vavrdaavrv arlaplsagp dlvppgpvwr lhparpgsis glelvecpev
tepltgrqvr igvraagmnf rdalttlgmy pgeagllgge aagevtgtgp evtgirtgdr
vtglvfggfg pigvtderll vrvpepwswa qaasvplvfi tawyalvdla glragekvlv
hagaggvgma aiqlahhlga evyatasdak qdvlrdlgva ddhiassrtt dfasawagag
idvvlnalsg efvdaslgll gdggrfvemg ktdvrdpdai pgvayrafdl meagpdriaa
mwqtllelfe sgvlaplpvr twdvrsaraa fthmsaarhv gklivtvppa rdpdgtvlit
ggtgglgael arhlvsehgv rhliltgrrg pdapgalelr aeitahgadv tvlaadvaer
devaallsti pdehpltavv haagvlddgm ldslnpdrmd avlrpkvdga whiheltaea
dlsafvlfss isgliggigg gnysaantfi dalaehrrgl grvgtslvwg pwdseagmvg
gltdadrarm sgsgmpplpv erglaifdaa lttaepvvvp vrpdvrgpav agavpsvlrg
sgaatrrtte ttldrlrgld adareellre lvisraasvl ghtdttaidp rqefislgfd
```

Figure 18 (Continued)

| | | |
|---|---|---|
| | | slvavelrnh lageldltlp asvvfdnetp drlaswlhee laghlvaada pteggpaav avdtdseetl vglflaavrr dksveamqml davaalrptf srtselerpa spvvladgpt tpkllfvsap gatggvhqya rlaahfrgrr rvlalplvgf epgetlpatg eaaiesvaes vlraadgapf vivghstggs layeaagime erwgvqpeav imidtmslry aegegadyeg vgryyladid spavaltstr ltamvhwynr aaalrpvget taptllvras iplpggkgpq eappldtdav ltidadhltm akehsgvtae ameewltslq aatr |
| 17 | ALE82591. 1 SelL | 1 mttndiptva tgpkqrlrps pemarlqeqa pvhrvrtpag deawlvtrya elkqllmckr 61 vgrshkdpas aprymdnpfm dmlliegdge tgmrehtdmr stlspmfslr rinalrpmvd 121 asaneivdam eaagppadlh rdfsmpfaln vlygligvap dkrgrmfell gamavltdpq 181 sardaglams aflndlvagk rsdpgddvis rlieaglsdq viatrcagil faglsdsvvsh 241 idvgvvliae ypeqraaaqa dptvikhave evlrtasagd sslpryanad ieiggvtire 301 gdlvlidftl tnfcprefdr peefdverhp nphmtfghgi whcvgaplar velqsafvtl 361 fgrlpglrpt tplldldads vslsggfnhl pvtw |
| 18 | ALE82592. 1 SelP | 1 mspqlsripa dasvdeaseI ldrdggliae nlidrdtlka lwadlrpala gneygtnsfa 61 gqktkrlssl farsrqmekl alnplflgva raqlqrasae qfgsqrvelt pnlqvsltqa 121 lqlwpgesqq vahrddvahl lpcpgptnrv qlmlamsefs aenggtvvyp gshrweadrs 181 ptpeeavate mspgscliwv gglyhrggpn rspgprtgit msyvrgnlrq eenqylavpr 241 eilreypeel qrllgydicp pnigwdned phrvlredat vs |
| 19 | ALE82593. 1 SelDl | 1 mqptrqpivf vshpesglfn pmlvlaeels rrgvadlyfa adsyrradve aagsrtpltf 61 vplgdsvpew taatwddety ravtqrsrfr ahraliehtf hpeasiekyr lleaaverig 121 palmviesmc aygvelaitk kiryalsnpf mpsnlltshv plmrsytprr fpvphsglpy 181 dmtlagritn etfkwrtvgm slqktmrell rrdrkvtael giapeakgfl srvdhaalil 241 sytvaeleyp msypdtmrlv gtmvpplpqa pddgglgawl dscdsvvymg fgtvtlrtre 301 hveslievcr rlgeqghhvi wklppdqgtm lppaemrpdt vrleswvpsq ldvlahekvr 361 vflthaggng fheglyfgvp lvvrplwidc ddqavrgsdf gvsltldrpe tvdvadvmck 421 ldrvlrdpaf rdraahyqrl lrqaggrrta adeligltp tatptqpa |
| 20 | ALE82594. 1 SelG | 1 mstpalrpap taerwhgapf vrqvtlltrr qlyamvhdpg lvvfgliqpc vllfftqif 61 snliqtsvlp agtsyldflm pavlvnhvvq sstgsgvglv edldngivsr lrslplrpvs 121 mllarsladi vrnvvgivll llialalmgy apgglsgil vscaltific wslswlflai 181 aastrsaetm nsisvlavlp lmflssgfvp lgalspwlaa iagvnplyv ieasrslaig |

Figure 18 (Continued)

| | | | |
|---|---|---|---|
| 21 | ALE82595.1 | SelH | 241 sdpgnlvtia lftclvlaav giagavrgfr epvlt<br><br>1 mtrarsdepi ieaigigrmf gstpalagvd ltvgrgtvmg lghngagkt tivniltamv<br>61 pptsgtarva gfdvsrepge vrkrigltgq yasvdeklsa idnlvliarl lgasktrara<br>121 radelieafg lthaasrkar tysgqmrrrl dlaaclvgnp evivldeptt gldpssrram<br>181 wdivtglvde gtsvllttqy ideadtladr itvlssgrvv asgtsaelks qvggrtvtvt<br>241 lapgsatgta rsalvsagta pavrddgtiv vpisasreta tviraldevg idvaelafge<br>301 ptlddvylal ahgtpefaa |
| 22 | ALE82596.1 | SelRI | 1 msdhspgrrr lvgrdvesaw laealvaaaa gepavrllvg ragigksall dqlcdtrppg<br>61 advrllrarg reqtadvsfa vvrdifgplg lgsgagspel leggarwsms alaedfagad<br>121 pdnvypvlhg lywltvnltt qaplivvvdd lqwcddgsla flaflirrca giplavvlat<br>181 rtdetgtipa rlagigggig vdvkqvrplg radiarlava rgpldaepih adlldalaea<br>241 sggspilver lvaelgpvtr eqatgrvhel grevidrlve rhvvapdvaa vasavavvga<br>301 eatcvlasls gvpagsvkda vdllvrtcvf apgrtdfrhd llrsavirrl pedritelrr<br>361 rgarvlsdag rpaesvaavi laipeisepw madvlleeat aaghrgaqpa varylapvlq<br>421 arphdvgvrm rlaaalgqta pdeavrqlre aldlapdlpt rarvavqlam tslavqqape<br>481 garilqdvld aldtaadtds gpeatelrth veaallvagl dekstvaeti arlrrmsvpa<br>541 grtpaergki ammtvakame gdgadaavem arrvlivdea tlggwavlas slvlrladev<br>601 eestavldrl vtqsrrqasa wtyslaigtr sanqilvgdl agaeddagaa ldvaeqeawr<br>661 gntvvptial asvrhlqgsp eealalldgi srprledfaw eyhlylmtra gasadtgdve<br>721 valalyrrcg qsldaagian pmlapwwaha avlladtgra aaargmveig eqsaarwgta<br>781 rsrglalilar gvitpgpggp elideavavl ensparmeli laylrlgrav lelgypeaar<br>841 ehlrhaatla arcgalraat aarellvrag grmrrptgsp ldpltgaerr vvalavdgar<br>901 nreiaealfi tlrtvevhlt safrklgvad raglaeivsg arvrrg |
| 23 | ALE82597.1 | SelRII | 1 mseptirvrg ggtaalgral dslaagtstv vtvtgepgtg rsrllhtaaa gararqvrvl<br>61 taravvaese yplgvvhgli rpidgsaelr rapgapadta llhrwcrlvl daahrrpvll<br>121 vvddllhwadt esqrwlqmli rhrhgapvgv lvaangthea aewagapair anvtlrtgpl<br>181 plaavraavt aaygaapdra fsvvarratg gnpavlaatl arldrsvtpt spavpelrrc<br>241 aalaraeqvr avldgipadi vtalraaavc gpdlwpvvdr iggppstga dvrtrlaatg<br>301 lvrgpgclli cdevvtdvvl agidpdrrg lfaraaalav raglpddgva rallaaptlg<br>361 epwgaellyr vacghrgrgn haaaaacaer aliepvppgl sgplmvelat arswtepvaa<br>421 rrmlalvvge adptdgphga qaadillladg dvgaarraia itvrrcagdt tahrdllsls |

Figure 18 (Continued)

| | | |
|---|---|---|
| 24 | ALE82598.1 | SelRIII |

```
431 rltdcelgydd llaapscape pagpgtdppp aastaaasgs lawseavrgr draaatrlar
541 ealaapdagw tpvmprvmaa mtlevagcph ealralepvl ldlagdrsvp pailamtalv
601 alragdldga rrdlraaraa sagrarpggg dpivaavqil lhlaegdlae atvvasarhg
661 vggdrpgial layalgrvha arggaragfe lfmrcgrlil drgrvnpalv pwrsaaaaal
721 aacdehaaal riardehrla vrwgappgia vagaavaalg relshvagp 1 mlrdrepelr vlrdavlraa dgrggaillg gglgtgrtal ldaaadiava aglrvlrata
 61 dvveqdfdkg varqlfdpli ataargdrer wlagrdvpga layvpadadd ptvahrwige
121 lqdlleavaa ggpvavcvdd lqwadgpsqr winhlavrvt glpvvlvata ldgdpcsqrp
181 pvrafarsaa vlrarlppe avdaviaerf wpaaapefvl achetcagnp lildtvlgel
241 vaagvrpdaa qagavraarp valrerlarc vrgqdpsarr ylravavlga gpdpevlrrl
301 geldradirt vpaslveggi itqggvvrvv hplveevate paeredihhr aarylhefgh
361 palevaghli avtaplatwa ievlraaaqq aaatpvpdar hsgvpdpdav dtairclrra
421 lldsgatsre rgvlivelas verfvepgta vrhvaqalpl ldsardraaa ltlldpamcr
481 dapdsvgeai rradtgdadg tvalrirara rmaeerpeg laeschilre virapdamls
541 tsagrelvgv lhaamltgh vpardiahlg erllritpar qlppppgvpp gdpprglivl
601 alvaadrpap veawlagqgd rdpavasade lalvqlaqgr vaaaalpgvl raagpptafh
661 aallaaaids rvlvpgravt drppgvglla hvthqmmraa racaheepdl alecfldggr
721 hldhlgwrnp alfpwrgwaa rlygrirgeyd aavayadeql tlaeawgapa aigralrirg
781 slaegadgta qlraavdvla gsgdlrelgr selalggrla ragdpagdel vrrgrqrtae
841 lgadaaatvd papapaaggt ppaepateaa agtgpegpd plteaaerrvv rlavggatng
901 aladdigisr ravekritsv yrklgvsgra alpgag
```

| | | |
|---|---|---|
| 25 | ALE82600.1 | SelO |

```
  1 mtatsdldaa tqdlrsrvae lhatrrearl gpsrqateqg hargkltvhe rldllldcpgs
 61 freleqfrrh ratfgledr rphtdgvvtg wgridgrtvf vyahdfrifg gslgeahatk
121 lhkvmdlaes agaplslsd gagarlqegv talagyggif rrnvrasgvv pgisvmlgpc
181 aggatyspal tdyvfmvrdi sqmyitgpdv vsavtgesit heelggahvh atetgaaafa
241 yddeetcfad vrhlvsllps nnreippvva tddprdrmtg alldivpadt sraydmhdvi
301 aevvddgdlf evhatwatni lcglarldgh tvgivanqps smagvldiha sekaarfvst
361 cdafsiplvt lvdvpgflpg gdqehggiir hgakillyayc aatvprvqvi lrkayggayi
421 vmdsrsigad islawptnei avmgaeaaan vvfrrelaaa pdpeearsqr ikqyrqelmh
481 pyyaaeaglv ddvidpaetr aalvealavl rakrtelpqr khgnppt
```

Figure 18 (Continued)

| | | |
|---|---|---|
| 26 | ALE82601.1 SelRIV | ```
  1 mrvstsegmt gerlssdsts acmvsldrsl rivaanqemf rrfhrtdtas icgssfctlv
 61 hpsirtrign qlerlldgqq prvyersval lgpdstvwgd lmatatarda grvegvmavl
121 rpvegdagpm agrgaprkil sdmdarileg vasgastvql astflsrgg veyhvtallr
181 kmkvknrpal iskaysmgff elgswppqvv pdhvk
``` |
| 27 | ALE82603.1 SelRV | ```
  1 mhadaapmsp vpgpavlher dddiaavegi vdrsfggtgg lvvvtgplga grtallaeca
 61 rraaerdvlv rrargaaaer rygfgvvrql lggdapdlfp apehpgsgpa gssdavseal
121 levlrdltsa rpglllvcdv tradpaslrw lahlgrrsag lratvvlavp dgdvpvgdta
181 vgellaradv vrplrpltpe giagvararl gtraddavvt algevsegnp lfldavveel
241 raapsdgrrv sghqvractp arirdrmaaa vrilpeptrr ylaalavigd vaddvllarl
301 aelchadada arrvageagi irpgrrprlr hrvvadalat tgsaeerrqt hiraatlihn
361 dgirpdrvas hlltvtssyp rwaigalrea aviatrrgep wtairylrha lladapeadr
421 aqvlvelasl ersvdaglal rvvaavpll apitaradal crampltleg aassvlamlr
481 gvaeeldgvt dpdpatrela lrlrarvlya drhrpagvta avarideler qpgglpldtp
541 gerelacvlt haaalsgrrt aaavaavgrt ilarepsaqh vhstiglvvg slcmadapee
601 ltawlgvald haraegatat eavvraelaa vlvcsgripe aeeqvrlsfe lfgeadedal
661 lpgliaavi pglqddrapae hilarygaaa evpegfgacl qmlrarvald agdpdaaley
721 cldagrrfer agwdigaavaw rpwaleirrg lgqlsearal aeeelvrtra wgaplqlgra
781 lrvlgelcgr draeplitea vevlrsandd relahairsl halpdrvghp ppdgscpttv
841 qtagftpsvl vdlspagrrg ghsgatwalt rseqrvalma aggrtnqeis dvlgvsvrav
901 ekhltgvyrk lrvsgrsalg rmwedgsdls a
``` |
| 28 | ALE82604.1 SelRVI | ```
  1 mdgapllerr aevdalreav ahacagrtrv vvvtgpagsg rtrlldvadg laaahdalvl
 61 ragggtrhpg rspfalardi lrrssaagptt daaailrdaa rrartegaag tdvaailglv
121 rsvagltaes pvvlladdld radpesvrwl ahlahhadgl pllvvgsvhs tpgagptara
181 ldelasapgv ghlapalsr davrswlhaa avpahpevl rdispeeial ahavaviged tapravalva
241 lahpapvtda adrihgigaa lavegvsavl drdgrrfrha aartavigtl sddrrcrlra wagrvleseg
301 elddvavdra aarlsalgil drdgrrfrha aartavigtl sddrrcrlra wagrvleseg
361 appervavqf ldagppacrg vvelmhgaac rarqrgapel aasflvhalr gnvpdrtraa
421 llldlgiter hsapgrahrh ltraislsgc arerarvitl lvafhtgpda eglvgllerg
481 lrdlaaavpe sgpeppgdrd lrlglealll yasaedsaqm aavrdwgdrt dphtlgcgag
541 asalrsahvf ystlllrtda aesavlarga ldgaldesea lqpirmgalg vlawteaddt
601 lapIherala darrgqrpel haslrgvrsm lhircgrvpe aladarasid vitgelsget
``` |

Figure 18 (Continued)

```
661 rlmilhcavl alielgevne aaalvhpanl egtsdrswrw swlldaraav laargrprea
721 lagaqeagrr lrnvgivnpa algwggrtal lhheigehaa aravalehig larrwgthgh
781 vgaalrvlgv vggvsgglrs lqdaavelgr sprvldsarc avdlgvmvre lgdeaqarvl
841 lregvdlaeg cgarvlsrra rteltaaggr grrsggvsl tpaelevarl aaagasnrdv
901 aaslgvsrrt velhltrcyr kldipgrael aralrrrvlp qpgesg
```

Figure 19

| Position | δ_H | mult (J in Hz) | δ_C | |
|---|---|---|---|---|
| 1 | | | 172.68 | C |
| 2 | H_a 2.53 | obs | 39.40 | CH_2 |
| | H_b 2.10 | ddd (17.4, 11.6, 5.7) | | |
| 3 | 1.81 | obs | 27.79 | CH_2 |
| | 1.36 | obs | | |
| 4 | 3.10 | obs | 72.80 | CH |
| 4-OH | 4.36 | d (7.0) | | |
| 5 | 3.46 | m | 74.17 | CH |
| 5-OH | 4.78 | d (3.3) | | |
| 6 | H_a 1.63 | dd (14.6, 10.4, 10.4) | 39.17* | CH_2 |
| | H_b 1.38 | d (13.8) | | |
| 7 | 4.26 | m | 68.27 | CH |
| 7-OH | 5.51 | s | | |
| 8 | H_a 1.53 | obs | 46.16 | CH_2 |
| | H_b 1.53 | obs | | |
| 9 | | | 97.32 | C |
| 9-OH | 5.89 | s | | |
| 10 | H_a 1.56 | obs | 40.39 | CH_2 |
| | H_b 1.52 | obs | | |
| 11 | 3.53 | ddd (12, 7.2, 4.8) | 68.27 | CH |
| 11-OH | 4.28 | d (7.2) | | |
| 12 | | | 71.18 | C |
| 12-OH | 3.61 | s | | |
| 13 | 3.96 | d (9.1) | 69.57 | CH |
| 14 | H_a 1.43 | dd (14.6, 9.3) | 33.38 | CH_2 |
| | H_b 2.10 | dd (15.1, 3.8) | | |
| 15 | 4.34 | d (7.6) | 76.29 | CH |
| 16 | 5.98 | dd (15.3, 9.1) | 136.38 | CH |
| 17 | 6.06 | dd (15.2, 10.4) | 128.25 | CH |
| 18 | 6.36 | dd (14.8, 10.5) | 132.88 | CH |
| 19 – 24 | 6.08 – 6.46 | | 131.5 – 133.5 | 6 CH |
| 25 | 5.35 | br s | 135.52* | CH |
| 26 | 2.50 | obs | 42.85* | CH |
| 27 | 3.10 | obs | 73.50* | CH |
| 28 | 1.83 | obs | 39.39* | CH |
| 29 | 5.23 | br s | 73.53 | CH |
| 30 | H_a 1.35 | obs | 22.68 | CH_2 |
| | H_b 2.06 | obs | | |
| 31 | 0.75 | t (7.3, 7.3) | 10.78* | CH_3 |
| 32 | 1.01 | s | 21.44 | CH_3 |
| 33 | 1.01 | obs | 17.87* | CH_3 |
| 34 | 0.93 | d (7.1) | 12.17 | CH_3 |
| 1' | 4.40 | s | 96.80 | CH |
| 2' | 3.57 | dd (9.2, 3.4) | 70.89 | CH |
| 2'-OH | 4.29 | d (3.2) | | |
| 3' | 3.18 | ddd (9.1, 6.0, 3.8) | 73.65 | CH |
| 3'-OH | 4.50 | d (6.2) | | |
| 4' | 3.08 | obs | 72.00 | CH |
| 4'-OH | 4.71 | d (4.9) | | |
| 5' | 3.06 | obs | 72.13 | CH |
| 6' | 1.14 | d (5.9) | 17.92 | CH_3 |
| 1" | 4.64 | br s | 98.66 | CH |
| 2" | H_a 1.79 | obs | 35.38 | CH_2 |
| | H_b 1.99 | dd (13.9, 4.7) | | |
| 3" | 4.05 | d (7.9, 4.1, 4.1) | 61.41 | CH |
| 3"-OH | 4.17 | br s | | |
| 4"-OMe | 3.28 | s | 55.79 | CH_3 |
| 4" | 2.81 | dd (6.6, 2.9) | 81.80 | CH |
| 5" | 4.07 | obs | 63.10 | CH |
| 6" | 1.16 | d (6.4) | 17.61 | CH_3 |

*Chemical shift extracted from HSQC spectrum

Figure 20

| Position | $\delta_H$ | mult (J in Hz) | $\delta_C$* | |
|---|---|---|---|---|
| 1 | | | 171.48‡ | C |
| 2 | H, 2.33 | ddd (17.4, 11.5, 4.6) | 29.38 | CH$_2$ |
|   | H, 2.08 | obs | | |
| 3 | H, 1.70 | obs | 25.14 | CH$_2$ |
|   | H, 1.57 | obs | | |
| 4 | 4.81 | obs | 73.34 | CH |
| 5 | 4.92 | d (0.8, 2.2, 2.2) | 70.38 | CH |
| 6 | H, 1.75 | obs | 34.33 | CH$_2$ |
|   | H, 1.67 | obs | | |
| 7 | 5.05 | obs | 67.26 | CH |
| 8 | 2.56 | dd (15.9, 9.9) | 45.93 | CH$_2$ |
|   | 2.47 | obs | | |
| 9 | | | 204.29‡ | C |
| 10 | H, 2.47 | obs | 41.98 | CH$_2$ |
|    | H, 2.77 | dd (18.3, 9.4) | | |
| 11 | 5.13 | dd (9.4, 2.5) | 70.28 | CH |
| 12-OH | 4.81 | s | | |
| 12 | | | 73.95‡ | C |
| 13 | 4.47 | d (9.7) | 71.68 | CH |
| 14 | H, 1.50 | t (12.7, 12.7) | 36.01 | CH$_2$ |
|    | H, 1.73 | obs | | |
| 15 | 2.96 | t (9.8, 9.8) | 77.10 | CH |
| 16 | 5.46 | dd (14.2, 8.9) | 133.01 | CH |
| 17–23 | 6.14–6.43 | | 131.0–134.0 | 7 CH |
| 24 | 6.01 | m | 130.17 | CH |
| 25 | 5.54 | dd (14.8, 9.8) | 132.95 | CH |
| 26 | 2.41 | m | ∘ | CH |
| 27 | 3.30 | obs | ∘ | CH |
| 28 | 1.98 | obs | 39.25 | CH |
| 29 | 5.00 | br s | 74.48 | CH |
| 30 | H, 1.43 | d (15.3, 7.9, 7.9) | 22.93 | CH$_2$ |
|    | H, 1.83 | obs | | |
| 31 | 0.78 | t (7.3, 7.3) | 9.41 | CH$_3$ |
| 32 | 0.95 | s | 12.77 | CH$_3$ |
| 33 | 0.95 | obs | 17.0 | CH$_3$ |
| 34 | 0.95 | obs | 11.45 | CH$_3$ |
| 1' | 4.89 | d (1) | 95.51 | CH |
| 2' | 5.25 | obs | 68.88 | CH |
| 3' | 5.08 | dd (10.2, 3.6) | 70.32 | CH |
| 4' | 4.75 | t (9.9, 9.9) | 70.19 | CH |
| 5' | 3.53 | dq (9.9, 6.4, 6.4, 6.4) | 68.95 | CH |
| 6' | 1.06 | d (6.1) | 17.05 | CH$_3$ |
| 1'' | 4.73 | d (4.66) | 97.64 | CH |
| 2'' | H, 1.93 | obs | 32.58 | CH$_2$ |
|     | H, 2.10 | obs | | |
| 3'' | 5.25 | obs | 64.28 | CH |
| 4'' | 2.98 | dd (9.4, 3.0) | 79.33 | CH |
| 4''-OMe | 3.24 | s | 55.96 | CH$_3$ |
| 5'' | 3.98 | dq (9.4, 6.4, 6.4, 6.4) | 62.63 | CH |
| 6'' | 1.11 | d (6.2) | 17.28 | CH$_3$ |
| Ac | 1.91–2.09 | | 20.3–20.7 | 9 CH$_3$ |
| Ac | | | 168.6–170.5‡ | 9 C |

* Chemical shifts extracted from HSQC spectrum, except where noted
‡ Chemical shift extracted from HMBC spectrum
∘ not observed

Figure 21

| | selvamicin | nystatin |
|---|---|---|
| *Candida albicans* SC5314 | 23 | 1.0 |
| *Saccharomyces cerevisiae* | 21 | 1.1 |
| *Trichoderma harzianum* T22 | 26 | 2.1 |
| *Aspergillus fumigatus* ATCC 1028 | 40 | 1.2 |

ANTIFUNGAL COMPOUNDS

RELATED APPLICATIONS

This application is a § 371 national-stage application based on PCT/US17/35697, filed Jun. 2, 2017 which claims the benefit of priority to U.S. Provisional Application No. 62/345,516, filed Jun. 3, 2016, and U.S. Provisional Application No. 62/397,079, filed Sep. 20, 2016, each of which is hereby incorporated in its entirety.

GOVERNMENT INTEREST

This invention was made with Government support under Grant No. AI109673 and Grant No. GM086258, awarded by the National Institutes of Health. The Government has certain rights in the invention.

BACKGROUND

Fungal diseases are often caused by fungi that are common in the environment. Most fungi are not dangerous, but some types can be harmful to health, particularly in immunocompromised individuals. Over the past several decades, there has been a significant rise in the number of recorded instances of fungal infection. In part this is due to increased awareness and improved diagnosis of fungal infection. However, the primary cause of this increased incidence is the rise in the number of susceptible individuals. This is attributed to a number of factors, including new and aggressive immunosuppressive therapies, increased survival in intensive care, increased numbers of transplant procedures and the greater use of antibiotics worldwide.

Clinically indispensable antifungal natural products include amphotericin B and nystatin $A_1$ both members of the World Health Organization's *List of Essential Medicines*, along with the food preservative and topical antifungal natamycin. However, the existing suite of clinically useful antifungals is limited. Although amphotericin B and nystatin $A_1$ have been used widely over the past 50 years, they suffer from major liabilities, most notably high toxicity and negligible oral bioavailability.

Hence, there is a need for effective antifungal agents and methods of producing such agents.

SUMMARY

In certain aspects, provided herein are compounds (e.g., antifungal compounds) having the structure of Formula I or Formula II:

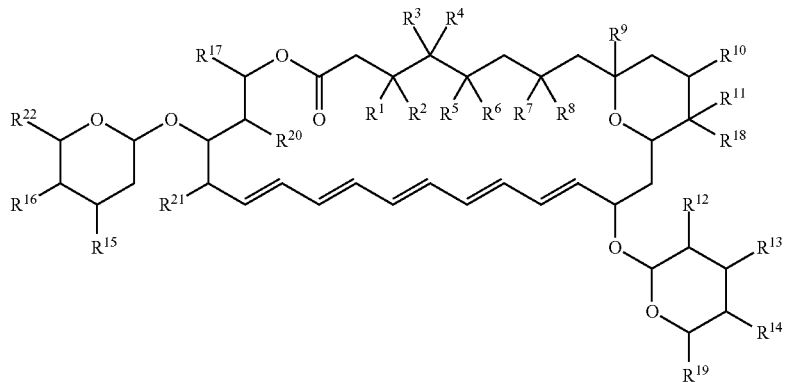

Formula I

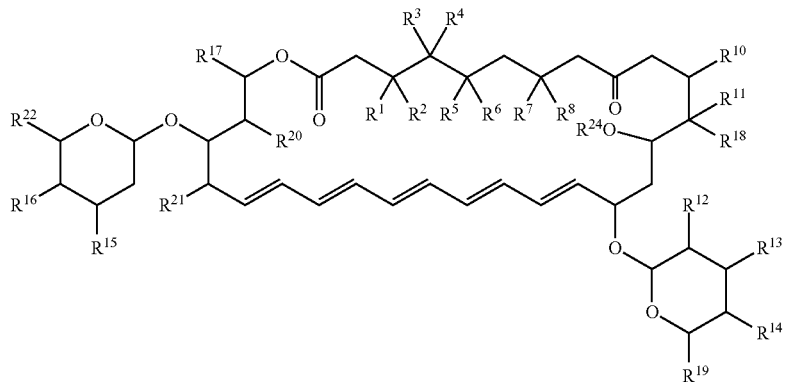

Formula II and pharmaceutically acceptable salts thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{24}$ are as defined herein.

In certain aspects, provided herein is a pharmaceutical composition comprising any one of the aforementioned compounds and a pharmaceutically acceptable carrier.

In some aspects, provided herein is a method of inhibiting the growth of a fungus, the method comprising contacting a fungus with a compound of any one of the aforementioned compounds or compositions.

In some aspects, provided herein is a method of treating or lessening the severity of a fungal infection in a subject, the method comprising administering to the subject a compound of any one of the aforementioned compounds or compositions. In some embodiments the method comprises treating candidiasis in a subject comprising administering to the subject a compound of any one of the aforementioned compounds or compositions.

In some aspects, provided herein is a selvamicin biosynthetic gene cluster (BGC). In some embodiments, the selvamicin BCG comprises one or more polynucleotides encoding SelE (SEQ ID No.: 2), SelDIII (SEQ ID No.: 3), SelI (SEQ ID No.: 4), SelJ (SEQ ID No.: 5), SelSI (SEQ ID No.: 6), SelSII (SEQ ID No.: 7), SelSIII (SEQ ID No.: 8), SelSIV (SEQ ID No.: 9), SelSV (SEQ ID No.: 10), SelSVI (SEQ ID No.: 11), and SelSVII (SEQ ID No.: 12), Sel A (SEQ ID No.: 13), SelB (SEQ ID No.: 14), SelC (SEQ ID No.: 15), SelK (SEQ ID No.: 16), SelL (SEQ ID No.: 17), SelP (SEQ ID No.: 18), SelDI (SEQ ID No.: 19), SelG (SEQ ID No.: 20), SelH (SEQ ID No.: 21), SelRI (SEQ ID No.: 22), SelRII (SEQ ID No.: 23), SelRIII (SEQ ID No.: 24), SelO (SEQ ID No.: 25), SelRIV (SEQ ID No.: 26), SelRV (SEQ ID No.: 27), and/or SelRVI (SEQ ID No.: 28). In some embodiments, the selvamicin BCG comprises a modified selvamicin BCG (e.g., comprising one or more inactivated or deleted genes selected from SelE, SelDIII, SelI, SelJ, SelSI, SelSII, SelSIII, SelSIV, SelSV, SelSVI, SelSVII, Sel A, SelB, SelC, SelK, SelL, SelP, SelDI, SelG, SelH, SelRI, SelRII, SelIII, SelO, SelRIV, SelRV, and SelRVI).

In some aspects, provided herein is a polynucleotide or expression vector (e.g., an isolated polynucleotide or expression vector) comprising a selvamicin BGC described herein (e.g., a modified selvamicin BCG).

In some aspects, provided herein is an engineered microorganism (e.g., an engineered bacterium) comprising one or more nucleic acids encoding a selyamicin BGC (e.g., a modified selvamicin BCG described herein). In some embodiments, the engineered microorganism is not Pseudonocardia.

In some aspects, provided herein is a method for producing an antifungal agent a polyene macrolide, including, for example, a compound of Formula I), the method comprising: culturing a microorganism (e.g., an engineered microorganism such as an engineered bacterium) comprising a selvamicin BCG described herein (e.g., a modified selvamicin BCG described herein) under conditions such that the bacterium produces the antifungal agent. In some embodiments, the engineered microorganism is not Pseudonocardia. In some embodiments the microorganism is cultured in the presence of sodium buterate. In certain embodiments, provided herein are the antifungal agents produced by such methods.

BRIEF DESCRIPTION OF THE FIGURES

FIG. 11 includes 2 panels (Panels A and B). Panel A shows the genomes of Pseudonocardia isolates LS1 and LS2. The selvamicin BGC in each is marked with a box. B) Selvamicin BGCs from LS1 and LS2. Mobile genetic element genes flanking the selvamicin clusters are shown.

FIG. 12 includes 2 panels (Panels A and B) showing Nystatin (Panel A) and selvamicin (Panel B) BGCs. Polyketide synthase genes are labeled with bold font.

FIG. 14 shows the extractions from PKS domain alignments. Active site residues and AT specificity motifs are in bold.

FIG. 16 includes 3 panels (Panels A-C). Panel A is a schematic of selvamicin PKS domain architecture. Panel B is a schematic of a modified selvamicin domain structure where the ketoreductase domain of module 13 is disrupted. Panel C is a schematic of a modified selvamicin domain structure where the dehydratase domain of module 14 is disrupted.

FIG. 17 is a table of predicted proteins of the selvamicin biosynthetic gene cluster (BGC)

FIG. 18 is a table of exemplary genes of the Selvamicin biosynthetic gene cluster.

FIG. 19 is a table of NMR Spectral data for selvamicin in DMSO-$d_6$.

FIG. 20 is a table of NMR Spectral data for $Ac_9$-selvamicin in DMSO-$d_6$.

FIG. 21 is a table of MIC values (μM) for selvamicin and nystatin against a pane of fungi.

DETAILED DESCRIPTION

Figure 1:
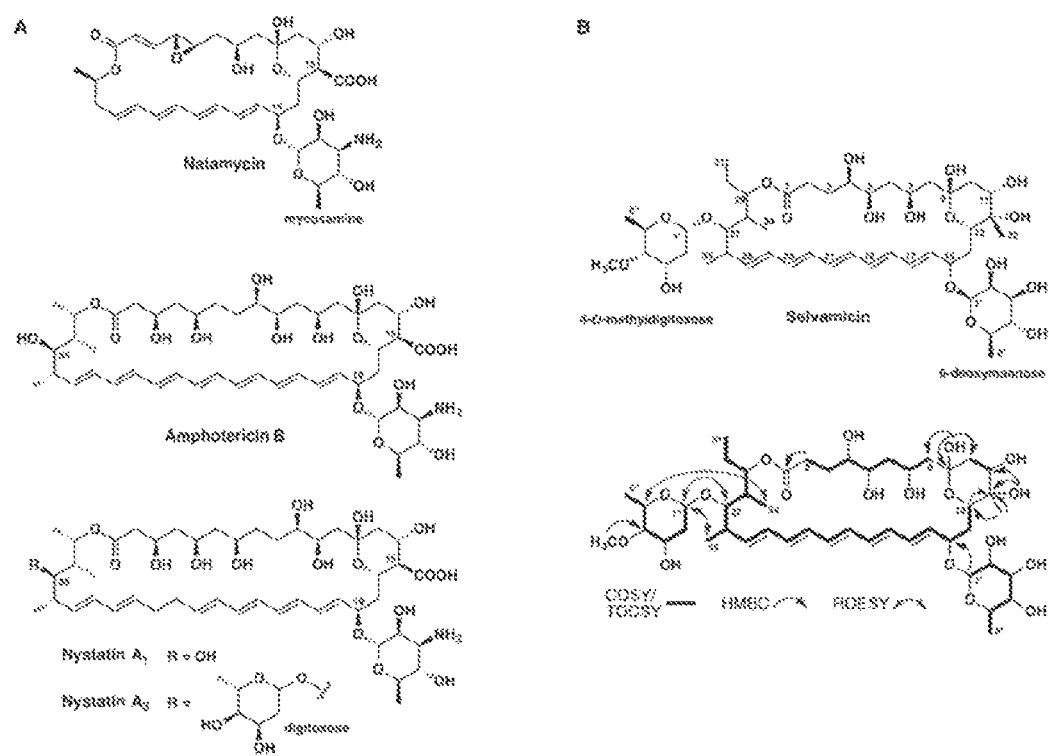
FIG. 1 includes 2 panels (Panels A and B). Panel A depicts structures of exemplary antifungal polyene natural products currently in clinical use. Panel B depicts the structure of selvamicin and NMR correlations establishing its planar structure.

In certain aspects, provided herein are methods and compositions related to novel polyene macrolide compounds. In certain embodiments, the polyene macrolide compounds are related to selvamicin, a novel polyene macrolide isolated from *Pseudonocardia*. As disclosed herein, selvamicin elicits antifungal activity.

I. Compounds

In certain aspects, provided herein are compounds having the structure of Formula I or Formula II, or a pharmaceutically acceptable salt thereof:

wherein $R^1$ and $R^2$ are, independently for each occurrence, H or $OR^{23}$, or $R^1$ and $R^2$ together with the carbon to which they are bound form a carbonyl moiety;

$R^3$ and $R^4$ are, independently for each occurrence, H or $OR^{23}$, or $R^3$ and $R^4$ together with the carbon to which they are bound form a carbonyl moiety;

$R^5$ and $R^6$ are, independently for each occurrence, H or $OR^{23}$, or $R^5$ and $R^6$ together with e carbon to which they are bound form a carbonyl moiety;

$R^7$ and $R^8$ are, independently for each occurrence, H or $OR^{23}$, or $R^7$ and $R^8$ together with the carbon to which they are bound form a carbonyl moiety;

$R^9$, $R^{10}$, $R^{11}$, $R^{12}$, $R^{13}$, $R^{14}$, $R^{15}$, and $R^{16}$ are, independently for each occurrence, H or $OR^{23}$;

$R^{17}$, $R^{18}$, $R_{19}$, $R^{20}$, $R^{21}$, and $R^{22}$ are, independently for each occurrence, H or optionally substituted alkyl;

$R^{23}$ is, independently for each occurrence, H, optionally substituted alkyl, or optionally substituted acyl; and $R^{24}$ is, independently for each occurrence, H, optionally substituted alkyl, or optionally substituted acyl.

In certain embodiments, the compound has a structure of Formula III or Formula IV or a pharmaceutically acceptable salt thereof:

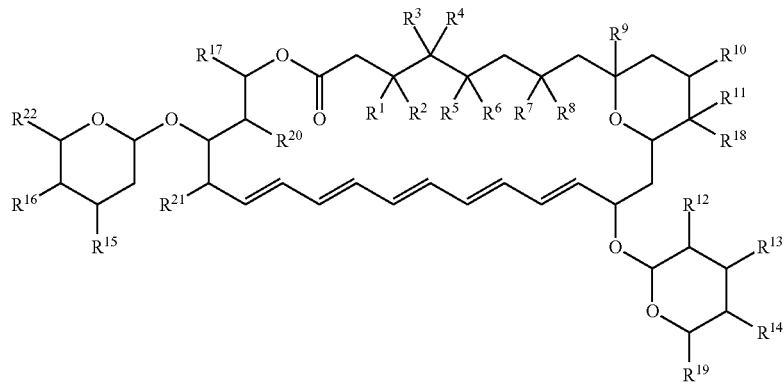

Formula I

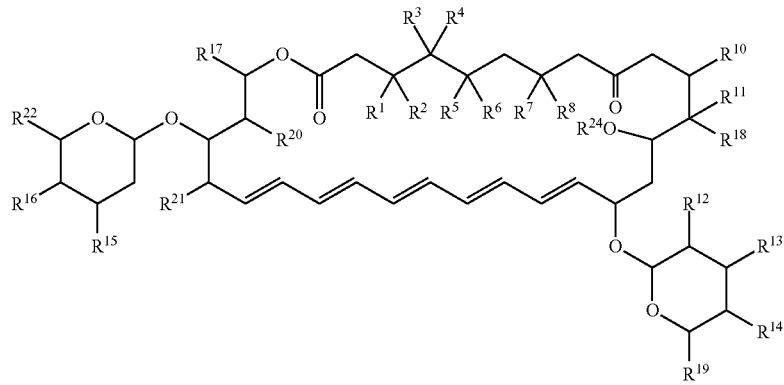

Formula II

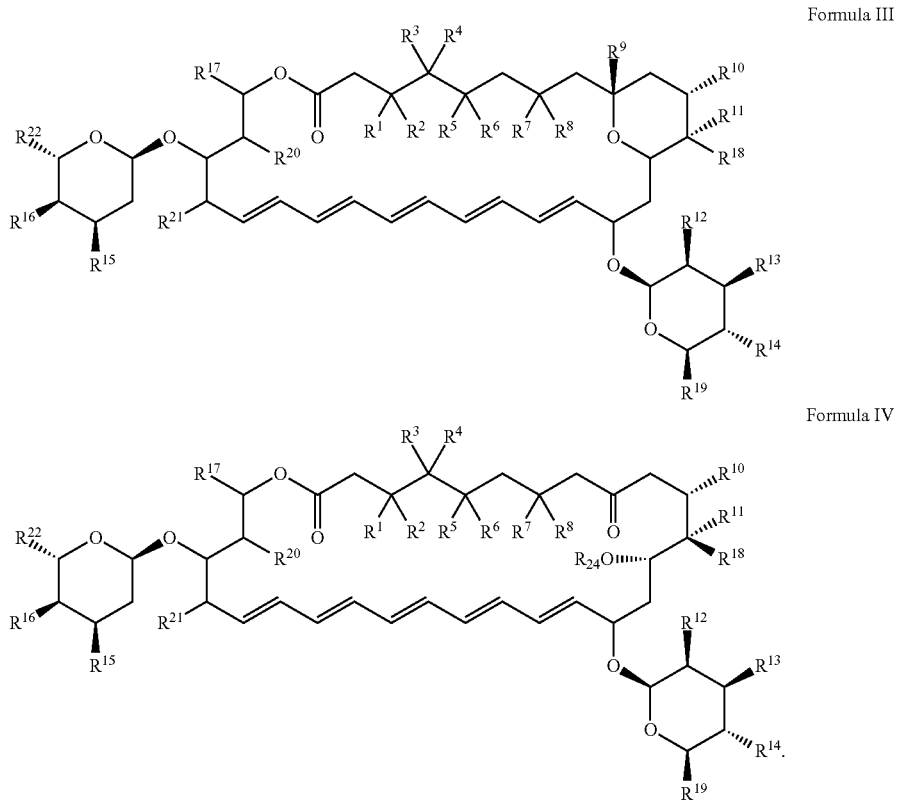

Formula III

Formula IV

In certain embodiments, $R^1$ and $R^2$ are H.

In certain embodiments, $R^3$ is $OR^{23}$ and $R^4$ is H. In certain such embodiments, $R^3$ is OH and $R^4$ is H. In certain embodiments. $R^5$ is $OR^{23}$ and $R^6$ is H. In certain such embodiments. $R^5$ is OH and $R^6$ is H. In certain embodiments. $R^7$ is $OR^{23}$ and $R^8$ is H. In certain such embodiments, $R^7$ is OH and $R^8$ is H.

In certain embodiments, $R^9$ is $OR^{23}$. In certain such embodiments, $R^9$ is OH. In certain embodiments, $R^{10}$ is $OR^{23}$. In certain such embodiments, $R^{10}$ is OH. In certain embodiments, wherein $R^{11}$ is $OR^{23}$. In certain such embodiments, $R^{11}$ is OH. In certain such embodiments, $R^{12}$ is $OR^{23}$. In certain embodiments wherein $R^{12}$ is OH. In certain embodiments, wherein $R^{13}$ is $OR^{23}$. In certain such embodiments, $R^{13}$ is OH. In certain embodiments, wherein $R^{14}$ is $OR^{23}$. In certain such embodiments, $R^{14}$ is OH. In certain embodiments, wherein $R^{15}$ is $OR^{23}$. In certain such embodiments, $R^{15}$ is OH.

In certain embodiments, $R^{16}$ is $OR^{23}$. In certain such embodiments, $R^{23}$ is lower alkyl, preferably $R^{16}$ is $OCH_3$.

In certain embodiments, $R^{17}$ is lower alkyl, preferably ethyl. In certain embodiments, $R^{18}$ is lower alkyl, preferably methyl. In certain embodiments, $R^{19}$ is lower alkyl, preferably methyl. In certain embodiments, $R^{20}$ is lower alkyl, preferably methyl. In certain embodiments, $R^{21}$ is lower alkyl, preferably methyl. In certain embodiments, $R^{22}$ is lower alkyl, preferably methyl.

In certain embodiments, the compound has the structure

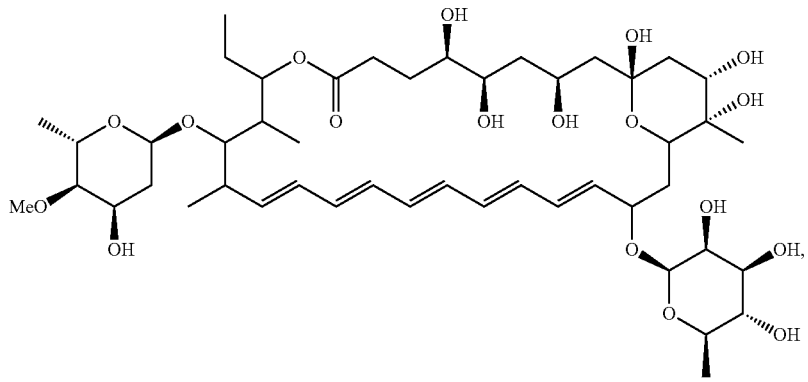

-continued

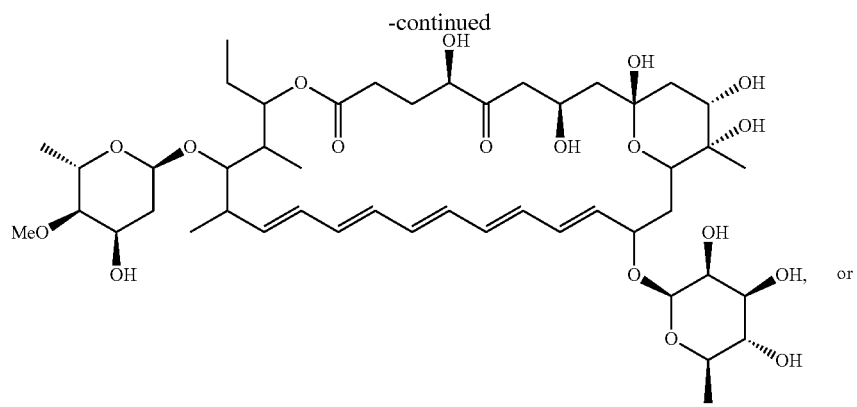

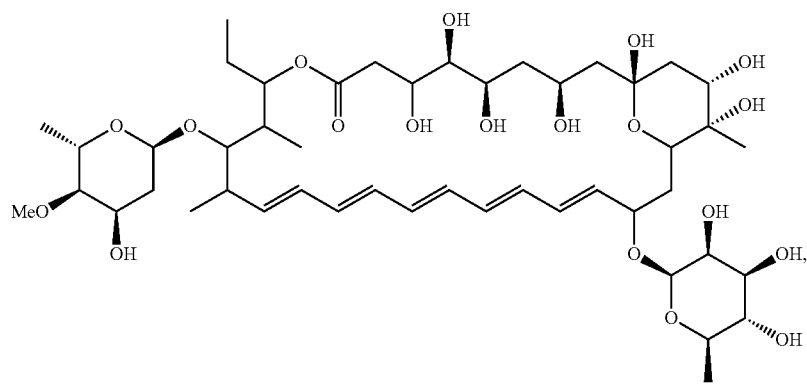

or a pharmaceutically acceptable salt thereof.

In certain embodiments, the compound does not have the following structure:

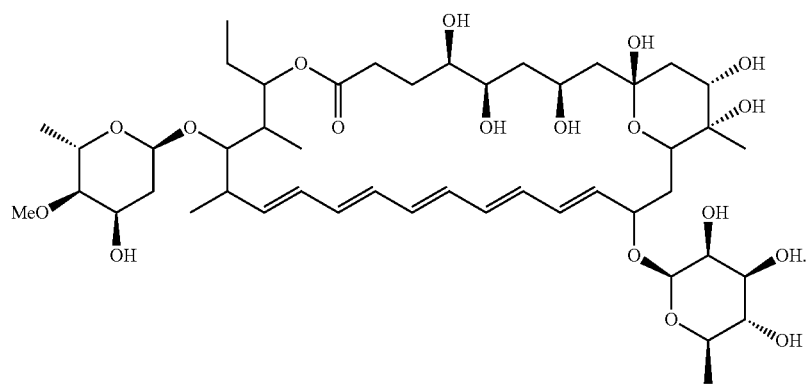 [SMILES: CCC1OC(=O)CC[C@@H](O)[C@H](O)C[C@H](O)C[C@]2(O)C[C@H](O)[C@](C)(O)C(CC(O[C@@H]3O[C@H](C)[C@@H](O)[C@H](O)[C@@H]3O)/C=C/C=C/C=C/C=C/C=C/C(C)C(O[C@H]3C[C@@H](O)[C@@H](OC)[C@H](C)O3)C1C)O2]

Exemplary compounds of Formula I and Formula II are depicted in Table 1. The compounds of Table 1 may be depicted as the free base or the conjugate acid. Compounds may be isolated in either the free base form, as a salt (e.g., a hydrochloride salt) or in both forms. In the chemical structures shown below, standard chemical abbreviations are sometimes used.

TABLE 1

Exemplary compounds of Formula I and Formula II

| Ex. | Structure | Name |
|---|---|---|
| 1 | 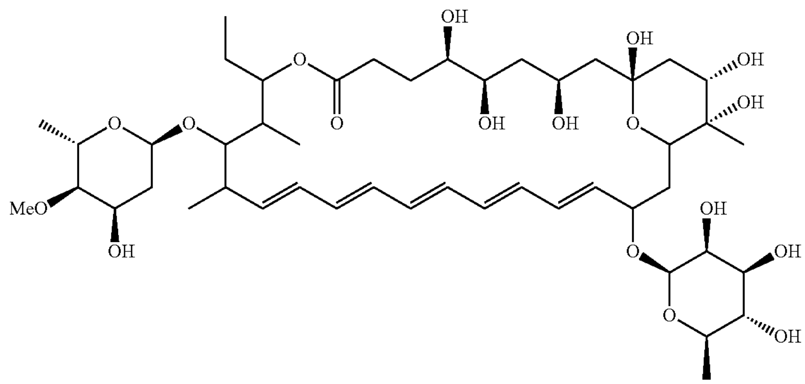 [SMILES: CCC1OC(=O)CC[C@@H](O)[C@H](O)C[C@H](O)C[C@]2(O)C[C@H](O)[C@](C)(O)C(CC(O[C@@H]3O[C@H](C)[C@@H](O)[C@H](O)[C@@H]3O)/C=C/C=C/C=C/C=C/C=C/C(C)C(O[C@H]3C[C@@H](O)[C@@H](OC)[C@H](C)O3)C1C)O2] | Selvamicin |
| 2 | 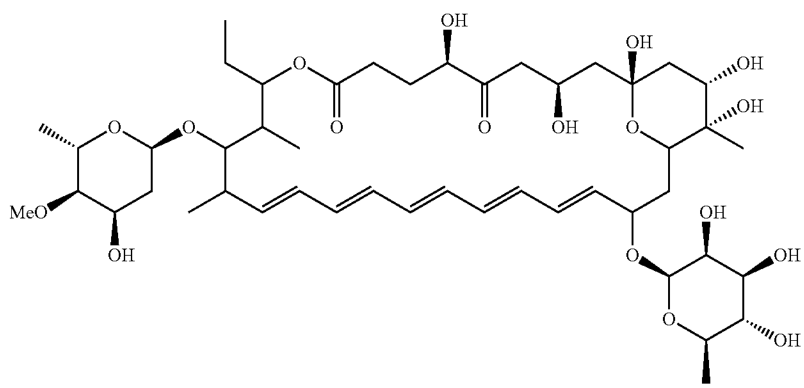 [SMILES: CCC1OC(=O)CC[C@@H](O)C(=O)C[C@H](O)C[C@]2(O)C[C@H](O)[C@](C)(O)C(CC(O[C@@H]3O[C@H](C)[C@@H](O)[C@H](O)[C@@H]3O)/C=C/C=C/C=C/C=C/C=C/C(C)C(O[C@H]3C[C@@H](O)[C@@H](OC)[C@H](C)O3)C1C)O2] | Analog 1 |
| 3 | 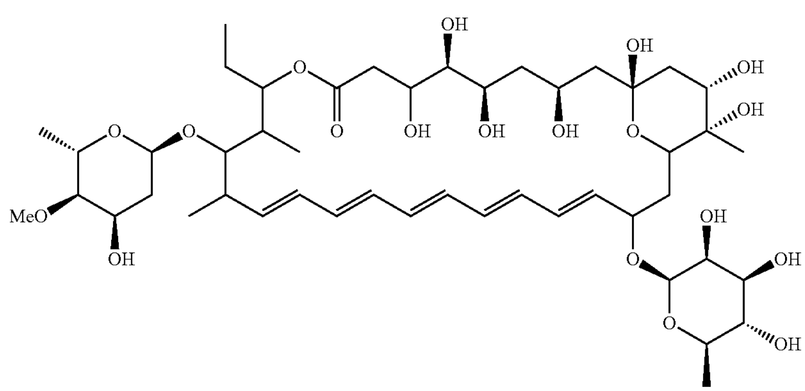 [SMILES: CCC1OC(=O)CC(O)[C@@H](O)[C@H](O)C[C@H](O)C[C@]2(O)C[C@H](O)[C@](C)(O)C(CC(O[C@@H]3O[C@H](C)[C@@H](O)[C@H](O)[C@@H]3O)/C=C/C=C/C=C/C=C/C=C/C(C)C(O[C@H]3C[C@@H](O)[C@@H](OC)[C@H](C)O3)C1C)O2] | Analog 2 |
| 4 | 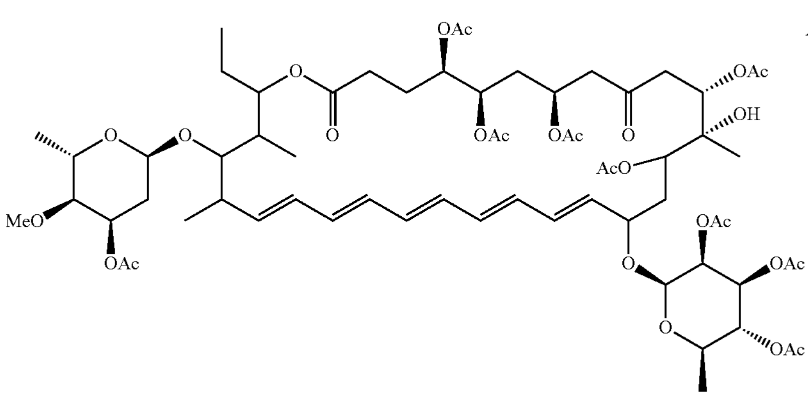 [SMILES: CCC1OC(=O)CC[C@@H](OC(C)=O)[C@H](OC(C)=O)C[C@H](OC(C)=O)CC(=O)C[C@H](OC(C)=O)[C@](C)(O)C(OC(C)=O)CC(O[C@@H]2O[C@H](C)[C@@H](OC(C)=O)[C@H](OC(C)=O)[C@@H]2OC(C)=O)/C=C/C=C/C=C/C=C/C=C/C(C)C(O[C@H]2C[C@@H](OC(C)=O)[C@@H](OC)[C@H](C)O2)C1C] | $Ac_9$-Selvamicin |

Selvamicin includes a hemiketal. Under the appropriate conditions, the molecule may adopt a ketone form (Scheme 1).

compound such as a compound described herein. Such physiologically acceptable agents include, for example, carbohydrates, such as glucose, sucrose or dextrans, antioxi- Scheme 1

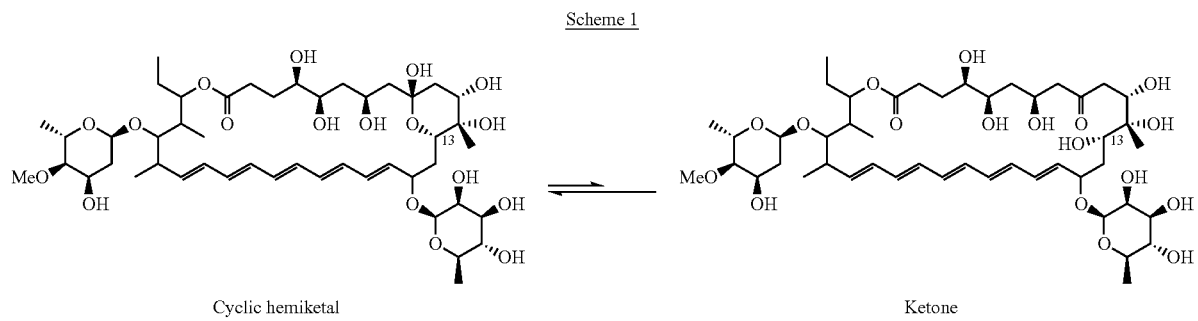 [SMILES: CCC1OC(=O)CC[C@@H](O)[C@H](O)C[C@H](O)C[C@]2(O)C[C@H](O)[C@](C)(O)[C@H](CC(O[C@@H]3O[C@H](C)[C@@H](O)[C@H](O)[C@@H]3O)/C=C/C=C/C=C/C=C/C=C/C(C)C(O[C@H]3C[C@@H](O)[C@@H](OC)[C@H](C)O3)C1C)O2 ; CCC1OC(=O)CC[C@@H](O)[C@H](O)C[C@H](O)CC(=O)C[C@H](O)[C@](C)(O)[C@@H](O)CC(O[C@@H]2O[C@H](C)[C@@H](O)[C@H](O)[C@@H]2O)/C=C/C=C/C=C/C=C/C=C/C(C)C(O[C@H]2C[C@@H](O)[C@@H](OC)[C@H](C)O2)C1C]

Cyclic hemiketal            Ketone

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% cc, or even 95% or greater ee. The compounds of the invention have more than one stereocenter. Consequently, compounds of the invention may be enriched in one or more diastereomer. For example, a compound of the invention may have greater than 30% de, 40% de, 50% de, 60% de, 70% de, 80% de, 90% de, or even 95% or greater de.

II. Pharmaceutical Compositions

In certain embodiments, the provided herein are pharmaceutical compositions comprising a compound disclosed herein and a pharmaceutically acceptable carrier.

The compositions and methods described herein may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound described herein and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly fir invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound described herein. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemuisifying drug delivery system. The pharmaceutical composition (preparation) also can be a liposome or other polymer matrix, which can have incorporated therein, for example, a compound described herein. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdemially (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound described herein, with the carrier and, optionally, one or more accessory ingredients. In general, the formulations are prepared by uniformly and intimately bringing into association a compound described herein with liquid carriers, or finely divided solid carriers, or both, and then, if necessary, shaping the product.

Formulations provided herein suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound described herein as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofiryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound described herein to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated herein. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some embodiments, the pharmaceutical composition may further comprise an adjuvant that can augment the immune response by increasing delivery of antigen, stimulating cytokine production, and/or stimulating antigen presenting cells. In some embodiments, the adjuvant can be administered concurrently with the pharmaceutical composition and/or vaccine composition disclosed herein, e.g., in the same composition or in separate compositions. For example, an adjuvant can be administered prior or subsequent to the pharmaceutical composition disclosed herein. Such adjuvants include, but are not limited to: aluminum salts, non-toxic bacterial fragments, cholera toxin (and detoxified fractions thereof), chitosan, homologous heat-labile of E. coli (and detoxified fractions thereof), lactide/glycolide homo and copolymers (PLA/GA), polyanhydride e.g. trimellitylimido-L-tyrosine, DEAF-dextran, saponins complexed to membrane protein antigens (immune stimulating complexes—ISCOMS), bacterial products such as lipopolysacchande (LPS) and mummyl dipeptide, (MDP), liposomes, cochelates, proteinoids, cytokines (interleukins, interferons), genetically engineered live microbial vectors, non-infectious pertussis mutant toxin, neurimidaselgalactose oxidase, and attenuated bacterial and viral toxins derived from mutant strains.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods provided herien, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors.

If desired, the effective daily dose of the active compound may be administered as one, two, three, four, five, six or more sub-doses administered separately at appropriate intervals throughout the day, optionally, in unit dosage forms. In certain embodiments described herein, the active compound may be administered two or three times daily. In preferred embodiments, the active compound will be administered once daily.

In some embodiments, provided herein is the use of pharmaceutically acceptable salts of compounds described herein in the compositions and methods described herein. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I or Formula II. As another example, the salt may comprise less than one inorganic or organic acid molecule per molecule of base, such as two molecules of compound of Formula I or Formula II per molecule of tartaric acid.

In further embodiments, contemplated salts described herein include, but are not limited to, alkyl, dialkyl, trialkyl or tetra-alkyl ammonium salts. In certain embodiments, contemplated salts described herein include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylalucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts described herein include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the pharmaceutical preparation may be enriched to provide predominantly one enantiomer of a compound (e.g., of Formula I or II). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grains of a second enantiomer, it would be said to contain 98 mol percent of the first enantiomer and only 2% of the second enantiomer.

In certain embodiments, the pharmaceutical preparation may be enriched to provide predominantly one diastereomer of a compound (e.g., of Formula I or II). A diastereomerically enriched mixture may comprise, for example, at least 60 mol percent of one diastereomer, or more preferably at least 75, 90, 95, or even 99 mol percent.

III. Therapeutic Uses

Provided herein are novel methods of inhibiting the growth of a fungus. In some embodiments, the method includes contacting a fungus with any compound or composition disclosed herein. In some embodiments, the method includes administering to a subject suffering from a fungal infection a compound or composition provided herein. In some embodiments, the method includes administering to a subject susceptible to fungal infection (e.g., an immunocompromised subject) a compound or composition disclosed herein. In some embodiments, the method includes treating an object (e.g., a food product or an exposed surface) with a compound or composition provided herein to prevent fungal growth on or in the object. In some embodiments, the fungus is *Aspergillus* (e.g., *Aspergillus fumigatus, Aspergillus flavus*), *Blastomyces, Candida, Coccidioides, Cryptococcus* (e.g., *Cryptococcus neoformans, Cryptococcus gattii*), *Histoplasma* (e.g., *Histoplasma capsulatum*), *Pneumocystis* (e.g., *Pneumocystis jirovecti*), *Sporothrix, Stachybontrys* (e.g., *Stachybotrys chartarum*), *Tinea, Exserohilum* and/or *Cladosporium*. In certain embodiments, the fungus is *Candida albicans, Saccharomyces cerevisiae, Trichoderma harzianum*, and/or *Aspergillus fumigatus*. In some embodiments, the fungus is *Candida glabrata*. In certain embodiments, the fungus is *Candida auris*.

In certain embodiments, disclosed herein are methods of preventing, treating or lessening the severity of a fungal infection in a subject (e.g., a subject that has a fungal infection and/or a subject that is susceptible to fungal infections, such as an immunocompromised subject), the method comprising administering to the subject any compound or composition disclosed herein. In some embodiments, the fungal infection is an infection with *Aspergillus* (e.g., *Aspergallus fumigatus, Aspergillus flavus*), *Blastomyces, Candida* (e.g. *Candida, albicans, Candida glabrata, Candida auris*), *Coccidioides, Cryptococcus* (e.g., *Cryptococcus neoformans, Cryptococcus gattii*), *Histoplasma* (e.g., *Histoplasma capsulatum*), *Pneumocystis* (e.g., *Pneumocystis jirovecii*), *Sporothrix, Stachybotrys* (e.g., *Stachybotrys chartarum*), *Tinea, Exserohilum* and/or *Cladosporium*. In some embodiments, the subject treated has aspergillosis, blastomycosis, candidiasis, coccidioidomycosis (valley fever), a *C. neuformans* infection, a *C. gattii* infection, a fungal eye infection, histoplasmosis, mucomiycosis, *Pneumocystis* pneumonia, ringworm, sporotrichosis, tinea pedis and/or tinea entris.

In certain embodiments, the compound or composition provided herien is administered to the subject, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). In some embodiments, the compound or composition is applied locally, directly to the site of the fungal infection.

IV. Selvanticin Biosynthetic Gene Cluster

Disclosed herein are is a selvamicin biosynthetic gene cluster (BGC) and the proteins encoded by the selvamicin BGC (FIG. 17).

In certain embodiments, also provided herein are modified selvamicin BGCs. In some embodiments, the modified selvamicin BGC comprises one or more inactivated or deleted genes selected from SelE, SelDIII, SelI, SelJ, SelSI, SelSII, SelSIII, SelSIV, SelSV, SelSVI, SelSVII, Sel A, SelB, SelC, SelK, SelL, SelP, SelDI, SelG, SelH, SelRI, SelRII, SelRIII, SelO, SelRIV, SelRV, and SelRVI (FIG. 18). (Each Accession Number nucleotide sequence incorporated by reference herein).

In certain embodiments, the inactivated gene is selected from SelP and SelL. In certain embodiments, the deleted gene is selected from SelP and SelL.

In some embodiments, provided herein are one or more polynucleotides encoding a selvamicin BCG. In some embodiments, the selvamicin BCG is a modified selvamicin BCG, In some embodiments, a the genes of the selvamicin BCG have an nucleic acid sequence that is at least 80 (e.g., at least 81, 82, 83, 84, 85, 86, 87, 88, 89, 90, 91, 92, 93, 94, 95, 96, 97, 98, or 99) % identical to the sequences disclosed herein. In some embodiments, the selvamicin BGC polynucleotide comprises a mutation or deletion in one of the polynucleotides that encode the proteins selected from SelE (SEQ ID No.: 2), SelDIII (SEQ ID No.: 3), SelI (SEQ ID No.: 4), SelJ (SEQ ID No.: 5), SelSI (SEQ ID No.: 6), SelSII (SEQ ID No.: 7), SelSIII (SEQ ID No.: 8), SelSIV (SEQ ID No.: 9), SelSV (SEQ ID No.: 10), SelSVI (SEQ ID No.: 11), and SelSVII (SEQ ID No.: 12), Sel A (SEQ ID No.: 13), SelB (SEQ ID No.: 14), SelC (SEQ ID No.: 15), SelK (SEQ ID No.: 16), SelL (SEQ ID No.: 17), SelP (SEQ ID No.: 18), SelDI (SEQ ID No.: 19), SelG (SEQ ID No: 20), SelH (SEQ ID No.: 21), SelRI (SEQ ID No.: 22), SelRII (SEQ ID No.: 23), SelRIII (SEQ ID No.: 24), SelO (SEQ ID No.: 25), SelRIV (SEQ ID No.: 26), SelRV (SEQ ID No.: 27), and SelRVI (SEQ ID No.: 28). In certain embodiments, SelP or SelL is mutated or deleted.

In some embodiments, the method includes a cell (e.g., a microbial cell, such as a bacterial cell) comprising a selvamicin BCG described herein. In certain embodiments, the polynucleotides can be introduced into the cell using any method known in the art. For example, in some embodiments, the polynucleotides are introduced in a vector. One type of vector is a "plasmid", which refers to a circular double stranded DNA loop into which additional DNA segments may be ligated. In some embodiments, the plasmid is linearized before introduction into the cell. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal eukaryotic vectors). Other vectors (e.g., non-episomal eukaryotic vectors) can be integrated into the genome of a host cell upon introduction into the host cell, and thereby are replicated along with the host genome.

Certain vectors are capable of directing the expression of genes to which they are operatively linked (expression vectors). The expression vectors provided herein are able to facilitate the expression of the encoded domain in a host cell, which means that the expression vectors include one or more e ulatory sequences (e.g., promoters, enhancers), selected on the basis of the host cells to be used for expression, which is operatively linked to the nucleic acid sequence to be expressed. The design of the expression vector can depend on such factors as the choice of the host cell to be transformed, the level of expression of protein desired, and the like.

The polynucleotides can be introduced into prokaryotic or eukaryotic host cells via conventional transformation or transfection techniques. Examples of transformation and transfection techniques include calcium phosphate or calcium chloride co-precipitation, DEAE-dextran-mediated transfection, lipofection, electroporation, optical transfection, protoplast fusion, impalefection, hydrodynamic delivery, using a gene gun, magnetofection, and particle bombardment. Polynucleotides can also be introduced by infecting the cells with a viral vector an adenovirus vector, an adeno-associated virus vector, a lentivirus vector or a retrovirus vector). Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

Also provided herein are proteins encoded by the selvamicin BGC polynucleotides disclosed herein. "Polypeptide," "peptide," and "protein" are used interchangeably and mean any peptide-linked chain of amino acids, regardless of length or post-translational modification. In some embodiments, the selvamicin BCG polynucleotides encode variant proteins. The variant proteins described herein comprise one or more amino acid substitutions, insertions, or deletions, relative to the wild-type protein from which they were derived. In some embodiments, a variant protein comprises at least one (e.g., at least two, three, four, five, six, seven, eight, nine, 10, 15, 20, 25, 30, 35, 40, 45, 50, 55, 60, 65, 70, 75, 80, 85, 90, 95, 100, or more than 100) amino acid substitutions, deletions, or insertions, relative to the wild-type, full-length NS3 protein from which it was derived. In some embodiments, a variant protein comprises no more than 150 (e.g., no more than 145, 140, 135, 130, 125, 120, 115, 110, 105, 100, 95, 90, 85, 80, 75, 70, 65, 60, 55, 50, 45, 40, 35, 30, 25, 24, 23, 22, 21, 20, 19, 18, 17, 16, 15, 14, 13, 12, 11, 10, 9, 8, 7, 6, 5, 4, 3, 2, or 1) amino acid substitution(s), deletion(s), or insertion(s), relative to the wild-type, full-length protein from which it was derived.

As used herein, the term "conservative substitution" refers to the replacement of an amino acid present in the native sequence in a given polypeptide with a naturally or non-naturally occurring amino acid having similar steric properties. Where the side-chain of the native amino acid to be replaced is either polar or hydrophobic, the conservative substitution should be with a naturally occurring amino acid, a non-naturally occurring amino acid that is also polar or hydrophobic, and, optionally, with the same or similar steric properties as the side-chain of the replaced amino acid. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. One letter amino acid abbreviations are as follows: alanine (A); arginine (R); asparagine (N); aspartic acid (D); cysteine (C); glycine (G); glutamine (Q); glutamic acid (E); histidine (H); isoleucine (I); leucine (L); lysine (K); methionine (M); phenylalanine (F); proline (P); serine (S); threonine (T); tryptophan (W), tyrosine (Y); and valine (V).

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted.

In some embodiments, a variant protein described herein, or a fragment thereof, has an amino acid sequence that is at least 80 (e.g., at least 81, 82, 83, 84, 85, 86, 87, 88, 89, 90, 91, 92, 93, 94, 95, 96, 97, 98, or 99) % identical to the sequences disclosed herein. Percent amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software, such as BLAST software or ClustalW2. Appropriate parameters for measuring alignment, including any algorithms needed to achieve maximal alignment over the full-length of the sequences being compared can be determined by known methods.

V. Methods of Producing Antifungal Agents

In certain embodiments, disclosed herein are methods for producing an antifungal agent (e.g., an antifungal agent described herein), the method comprising culturing a microorganism described herein (e.g. an engineered microorganism, such as an engineered bacterium comprising a selvamicin BGC described herein) under conditions such that the microorganism produces the antifungal agent. In some embodiments, the method further comprises isolating the antifungal agent. In some embodiments, the microorganism is cultured in the presence of sodium butyrate. In certain embodiments, provided herein are the antifungal agents produced by such methods.

In embodiments the microorganism is cultured on or in a microbial medium (e.g., an agar medium or a broth medium). In some embodiments, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 hemin chloride, 2 mg/L calcium chloride, 1 mg/L menadione. Another examples would be a medium composed of 10 g/L beef extract, 10 g/L peptone, 5 g/L sodium chloride, 5 g/L dextrose, 3 g/L yeast extract, 3 g/L sodium acetate, 1 g/L soluble starch, and 0.5 g/L L-cysteine HCl, at pH 6.8. A variety of microbiological media and variations are well known in the art (e.g., R. M. Atlas, *Handbook of Microbiological Media* (2010) CRC Press). Culture media can be added to the culture at the start, may be added during the culture, or may be intermittently/continuously flowed through the culture. The strains in the bacterial composition may be cultivated alone, as a subset of the microbial composition, or as an entire collection comprising the microbial composition. As an example, a first strain may be cultivated together with a second strain in a mixed continuous culture, at a dilution rate lower than the maximum growth rate of either cell to prevent the culture from washing out of the cultivation. In some embodiments, the microbial medium comprises sodium butyrate (e.g., between 50 and 500 mM sodium butyrate, such as about 50, 60, 70, 80, 90, 100, 110, 120, 130, 140, 150, 160, 170, 180, 190, 200, 210, 220, 230, 240, 250, 260, 270, 280, 290, 300, 350, 400, 450 or 500 mM sodium butyrate). In some embodiments, the microbial medium comprises between 100 and 200 mM sodium butyrate. In some embodiments, the microbial medium comprises about 150 mM sodium butyrate.

In certain embodiments, disclosed herein are methods for producing a modified polyene macrolide, the method comprising: culturing a host cell (e.g., a microorganism, such as a bacterium) comprising a polynucleotide encoding SelSI (SEQ ID No.: 6), SelSII (SEQ ID No.: 7), SelSIII (SEQ ID No.: 8), SelSIIV (SEQ ID No.: 9), SelSV (SEQ ID No.: 10), SelSVI (SEQ ID No.: 11), and SelSVII (SEQ ID No.: 12), under conditions such that the host cell produces a modified polyene macrolide. In certain embodiments, disclosed herein are the modified polyene macrolide produced by such methods. In certain embodiments the host cell is a bacterium.

In certain aspects, provided herein are engineered microorganisms (e.g., bacteria) described herein. In some embodiments, the engineered microorganisms are modified to enhance certain desirable properties. The engineered microbe(s) may be produced using any technique known in the art, including but not limited to site-directed mutagenesis, transposon mutagenesis, knock-outs, knock-ins, polymerase chain reaction mutagenesis, chemical mutagenesis, ultraviolet light mutagenesis, transformation (chemically or by electroporation), phage transduction, directed evolution, or any combination thereof.

In certain embodiments, disclosed herein are engineered microorganisms comprising a polynucleotide of selvamicin BGC (SEQ ID No.: 1). In certain embodiments, the polynucleotide of selvamicin BGC is modified. In certain embodiments, one or more of the polynucleotides selected from SelE (SEQ ID No.: 2), SelDIII (SEQ ID No.: 3), SelI (SEQ ID No.: 4), SelI (SEQ ID No.: 5), SelSI (SEQ ID No.: 6), SelSII (SEQ ID No.: 7), SelSIII (SEQ ID No.: 8), SelSIV (SEQ ID No.: 9), SelSV (SEQ ID No.: 10), SelSVI (SEQ ID No.: 11), and SelSVII (SEQ ID No.: 12), Sel A (SEQ ID No.: 13), SelB (SEQ ID No.: 14), SelC (SEQ ID No.: 15), SelK (SEQ ID No.: 16), SelL (SEQ ID No.: 17), SelP (SEQ ID No.: 18), SelDI (SEQ ID No.: 19), SelG (SEQ ID No.: 20), SetH (SEQ ID No.: 21), SelRI (SEQ ID No.: 22), SelRII (SEQ ID No.: 23), SelRIII (SEQ ID No.: 24), SelO (SEQ ID No.: 25), SelRIV (SEQ ID No.: 26), SelRV (SEQ ID No.: 27), and SelRVI (SEQ ID No.: 28) is imitated or deleted. In certain embodiments, the engineered microorganism is a bacteria other than *Pseudonocaidia*. In some embodiments, the engineered microorganism is *Escherichia coli*. In certain embodiments, disclosed herein are methods of producing a compound of Formula I, the method comprising: culturing an engineered microorganism of any disclosed herein; and allowing the compound of Formula I to accrue.

VI. Definitions

The articles "a" and "an" are used herein to refer to one or to more than one (i.e., to at least one) of the grammatical object of the article. By way of example, "an element" means one element or more than one element.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a hetereocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amino, phosphoryl (including phosphonate and phosphinate), sulfonyl (including sulfate, sulfonamido, sulfarnoyl and sulfonate), and sityl groups, as well as ethers, alkylthios, carbonyls (including ketones, aldehydes, carboxylates, and esters), $—CF_3$, —CN and the like. Exemplary substituted alkyls are described below. Cycloalkyls can be further substituted with alkyls, alkenyls, alkoxys, alkyithios, aminoalkyls, carbonyl-substituted alkyls, $—CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "carboxy", as used herein, refers to a group represented by the formula —CO$_2$H.

The term "heteroalkyl", as used herein, refers to a saturated or unsaturated chain of carbon atoms and at least one heteroatom, wherein no two heteroatoms are adjacent.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. In some embodiments, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamide, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratlyloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, "administration" broadly refers to a route of administration of a composition to a subject. Examples of routes of administration include oral administration, rectal administration, topical administration, inhalation (nasal) or injection. Administration by injection includes intravenous (IV), intramuscular (IM), intratumoral (IT) and subcutaneous (SC) administration. The pharmaceutical compositions described herein can be administered in any form by any effective route, including but not limited to intratumoral, oral, parenteral, enteral, intravenous, intraperitoneal, topical, transdermal (e.g., using any standard patch), intradermal, ophthalmic, (intra)nasally, local, non-oral, such as aerosol, inhalation, subcutaneous, intramuscular, buccal, sublingual, (trans)rectal, vaginal, intra-arterial, and intrathecal, transinucosal (e.g., sublingual, lingual, (trans)buccal, (trans)urethral, vaginal (e.g., trans- and perivaginally), intravesical, intrapulmonary, intraduodenal, intragastrical, and intrabronchial. In preferred embodiments, the pharmaceutical compositions described herein are administered orally, rectally, intratumorally, topically, intravesically, by injection into or adjacent to a draining lymph node, intravenously, by inhalation or aerosol, or subcutaneously.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The term "isolated nucleic acid" refers to a polynucleotide of natural or synthetic origin or some combination thereof, which (1) is not associated with the cell in which the "isolated nucleic acid" is found in nature, and/or (2) is operably linked to a polynucleotide to which it is not linked in nature.

The term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FAST, A and BLAST are available as a part of the GCG sequence analysis package (University of Wisconsin, Madison, Wis.), and can be used with, e.g., default settings. ENTREZ is available through the National Center for Biotechnology Information, National Library of Medicine, National institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

The term "prodrug" is intended to encompass compounds which, under physiologic conditions, are converted into the therapeutically active agents described herein (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs described herein. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

EXAMPLES

The invention now being generally described will be more readily understood by reference to the following examples which are included merely for purposes of illustration of certain aspects and embodiments of the present invention, and are not intended to limit the invention in any way.

Experimental Methods

General chemical analysis procedures: UV-visible absorbance spectra were collected on an Amersham Biosciences Ultrospec 5300 Pro spectrophotometer. High resolution mass spectrometry analysis was performed on an Agilent 6530 ESI QTOF mass spectrometer interfaced with air Agilent 1290 Infinity Binary LC. COSY, TOCSY, ROESY, HSQC, H2BC, HMBC, and 1H NMR experiments were performed on either a Varian VNMRS 600 MHz spectrometer equipped with a triple resonance HCN inverse probe or on a Varian INOVA 500 MHz spectrometer equipped with a triple resonance HCN coldprobe. 13C NMR experiments were performed on a Varian 400 MHz spectrometer equipped with a Varian OneNMR probe. Chemical shifts were referenced to the residual solvent peak in DMSO-d6. Optical rotation was measured on a Jasco P-2000 polarimeter fitted with a microcell (10 mm path length).

Selvamicin production and purification: Spores of *Pseudonocardia LS*1 were diluted into sterile double distilled water (ddH2O) and spread onto plates of ISP2 agar (BD Difco™ ISP2; 60 mL agar per 150×15 mm Petri dish) supplemented with sodium butyrate (Aldrich, 150 mM final concentration, added after autoclaving), which were incubated at 30° C. for 14 d. Agar was then cut into squares and soaked in ethyl acetate overnight to extract organic components from the solid media. This extract was decanted and the agar was soaked in an additional volume of ethyl acetate for 3 h. The combined ethyl acetate extracts were concentrated in vacuo and adsorbed onto celite for dry packing onto a 10 g C18 SepPak column (Waters) that had been conditioned with acetonitrile and pre-equilibrated with 30% acetonitrile in water. Fractions were eluted with a step gradient of 30%, 50%, 70%, and 100% acetonitrile in water and concentrated to dryness. Consecutive fractions from elution at 50% acetonitrile were most active in inhibition of *Candida albicans*. Semipure material from these fractions was purified by reversed-phase HPLC (Agilent 1200 series preparative HPLC equipped with a diode array detector; Phenomenex Luna 10 µm phenyl-hexyl preparative column, 250×21.20 mm, 10 mL/min) with a gradient of 40% to 63% acetonitrile in water over 20 min. Selvamicin eluted at 12.5 min. The overall yield of pure selvamicin (isolated as an amorphous pale yellow solid) was 100 mg/L of agar.

Selvamicin: $[\alpha]D$ 26+128° (MeOH); UV (MeOH) $\lambda$max (log $\varepsilon$) 305 (4.4), 319 (4.7), 334 (4.9), 352 (4.9) nm; NMR spectral data, see FIG. 19; HR-ESI-TOFMS m/z 951.4928 [M+Na]+ (calcd for C47H76NaO18:951.4924)

Preparation of Ac$_9$-selvamicin: Selvamicin (18 mg) was dissolved in anhydrous pyridine (0.5 mL) under nitrogen in an oven-dried vial containing a dry stir bar. This solution was cooled to 0° C. with stirring and a solution dimethylaminopyridine (1 mg) in anhydrous pyridine (100 µL) and acetic anhydride (100 ot) was added dropwise. After 5 min the reaction solution was warmed to room temperature and was stirred at room temperature under nitrogen for 5 h, at which point the reaction was complete by TLC. The reaction solution was evaporated to dryness in vacuo and Ac$_9$-selvamicin was purified by reversed-phase HPLC (Agilent 1200 series semipreparative HPLC equipped with a diode array detector; Phenomenex Luna 5 µm C18 column, 250× 10 mm, 3 mL/min) with an isocratic solvent mixture of 87% acetonitrile in water. Ac$_9$-selvamicin eluted at 8.4 min.

Ac$_9$-selvamicin: NMR spectral data see FIG. 20; FIR-ESI-TOFMS m/z 1329.5885 [M+Na]+ (calcd for C65H94NaO27: 1329.5875)

Solubility determination: Solubility for selvamicin and nystatin was measured with minor modifications from a previously reported protocol. 1 Briefly, in microcentrifuge tubes, 20 µL 5 inM HEPES (pH=7.4) was added to 2.5 mg of selvamicin and of nystatin and the resulting suspensions were vortexed vigorously for 30 min at 22° C. The tubes were centrifuged, the resulting supernatants were diluted in HEPES buffer, and concentrations were determined by UV-vis absorbance (306 nm for nystatin and 335 nm for selvamicin).

Isothermal Calorimetry Sterol Binding Assay:

Large unilamellar vesicle (LUV) preparation: In a glass vial, a 25 mg/mL solution of palmitoyl oleoyl phosphatidylcholine (POPC) in chloroform (0.96 mL, Avanti Polar Lipids) was mixed with a freshly prepared 4 mg/mL solution of the appropriate sterol (ergosterol or cholesterol. Aldrich) in chloroform (0.35 mL). The sterol solution was omitted for preparation of sterol-free POPC LUVs. The resulting solution was evaporated to dryness in vacuo to yield a lipid film, which was placed under high vacuum for at least 5 h. To this film was added 1 mL 5 mM HEPES (pH adjusted to 7.4 with KOH) and the resulting suspension was vortexed for 3 min. This lipid suspension was loaded into a syringe and passed through a 0.1 µM filter (Whatman) 21 times using an Avanti Polar Lipids Mini-Extruder to yield an LUN suspension (32 mM POPC, 11 mol % sterol; assumed no loss during extrusion).

Isothermal calorimetry (ITC) experiments: Solutions of polyene (150 µM selvamicin or nystatin) in 1% DMSO/5 mM HEPES (pH=7.4) were prepared by dilution from a 1.5 mM solution in DMSO. 8 mM POPC LUV suspensions in 1% DMSO/5 mM HEPES (pH=7.4) were prepared by dilution of the above LUV suspensions with HEPES buffer and DMSO. ITC experiments were performed on a MicroCal iTC200 instrument (Malvern Instruments) with the 150 µM polyene solution in the sample cell (200 µL) and the LUV suspension injected by pipette. Experiments were performed at 25° C. and consisted of an initial injection of 0.4 µL followed by 18 injections of 2 µL each at intervals of 150 s. Experiments were performed for both nystatin and selvamicin with sterol-free LUVs, cholesterol-containing LUVs, and ergosterol-containing LUNs, with a minimum of two replicates for each condition. Robust binding, as indicated by heats evolved, was observed only for nystatin with ergosterol-containing vesicles. A dissociation constant for the nystatin-ergosterol interaction was estimated with the MicroCal ITC-ORIGIN analysis software in which the integrated heat for the last injection was subtracted from all of the data and a single binding site was assumed.

Induction with propionate and butyrate: Spores of each Pseudonocardia isolate were diluted into sterile double distilled water (ddH2O) and spread onto ISP2 agar (BD Diko™ ISP2; 1.5 mL agar per well in 12-well plates) supplemented with the appropriate inducer (sodium butyrate or sodium propionate, Aldrich; 1-13C-sodium butyrate or 1-13C-sodium propionate. Cambridge Isotope Labs; 0, 25, or 150 mM final concentration with all conditions in duplicate; added after autoclaving), which were incubated at 30° C. for 14 d. The agar was cut out of each well and soaked in 2 mL ethyl acetate for 48 h. The ethyl acetate extract was evaporated to dryness in vacuo, redissolved in 0.1 mL methanol, and analyzed by HPLC (Agilent 1200 series, equipped with a diode array detector). The selvamicin peak in the 375 nm absorbance chromatogram was integrated for each sample. Samples were also analyzed by HPLC-high resolution Determination of minimum inhibitory concentration: Fresh DMSO solutions of selvarmicin and nystatin were prepared as serial dilutions and dispensed into clear flat-bottom 96-well plates in four replicates. A starting inoculum of the appropriate test strain in media was added to each well to yield a final concentration of 1% DMSO by volume. The plates were incubated at 30° C. with shaking at 200 rpm. Growth was assayed by OD600 readings taken on a M5 plate reader (Molecular Devices). For *E. coli*, *B. subtilis*, and *M. luteus*, the starting inoculum consisted of an overnight culture in LB diluted into LB media at 10 µL/mL and final OD readings were taken at 22 h. For *C. albicans* and *S. cerevisiae*, the starting inoculum consisted of an overnight culture in YPD media diluted to an OD600 of 0.05 in YPD media and final OD readings were taken at 14 h. For *T. harzianum* and *A. fumigatus*, the starting inoculum consisted of a stock of concentrated conidia diluted into potato dextrose broth at 2 uL/mL and final OD readings were taken at 22 h. Using Prism (GraphPad), the OD data were normalized and fit to a Gompertz function, from which MIC values were extracted.

Genome sequencing and data deposition: DNA isolation and genome sequencing was performed. The complete genome for *Pseudonocardia* LS2 (HH130630-07) has been deposited in the GenBank database (accession nos. CP013854, CP013855, and CP013856) and raw sequence data has been deposited in the Sequence Read Archive. The *Pseudonocardia*. LS1 (HH130629-09) genome can be accessed using Genbank accession nos. CP011868 and CP011869.

Sequence comparison and analysis: Conserved replicons in the two chromosomes were compared using an average nucleotide identity (ANI) calculator, which provided a two-way ANI value of 83.3% from 8071 genomic fragments. The selvamicin gene cluster annotations were performed using antiSMASH24 and blastp (nonredundant proteins db). The Geneious aligner was used for pairwise alignment with proteins from the nystatin biosynthetic gene cluster from *S. noursei* ATCC 11455 (accession no. AF263912). Polyketide synthase domains were detected by antiSMASH2,4 and the translated protein sequences were aligned using Clustal W. Extractions from these domain alignments are displayed in FIG. 14.

Example 1

Discovery and Structure Elucidation of Selvamicin

Two *Pseudonocardia* isolates from ants in the genus *Apterostigma* collected at La Selva Biological Station, Costa Rica, HH130629-09 and Hh-1130630-07 (hereafter LS1 and LS2, respectively) were examined. Antifungal activity of organic-soluble extracts of cultures for both strains was evaluated against the common human fungal pathogen *Can-*

Figure 2:
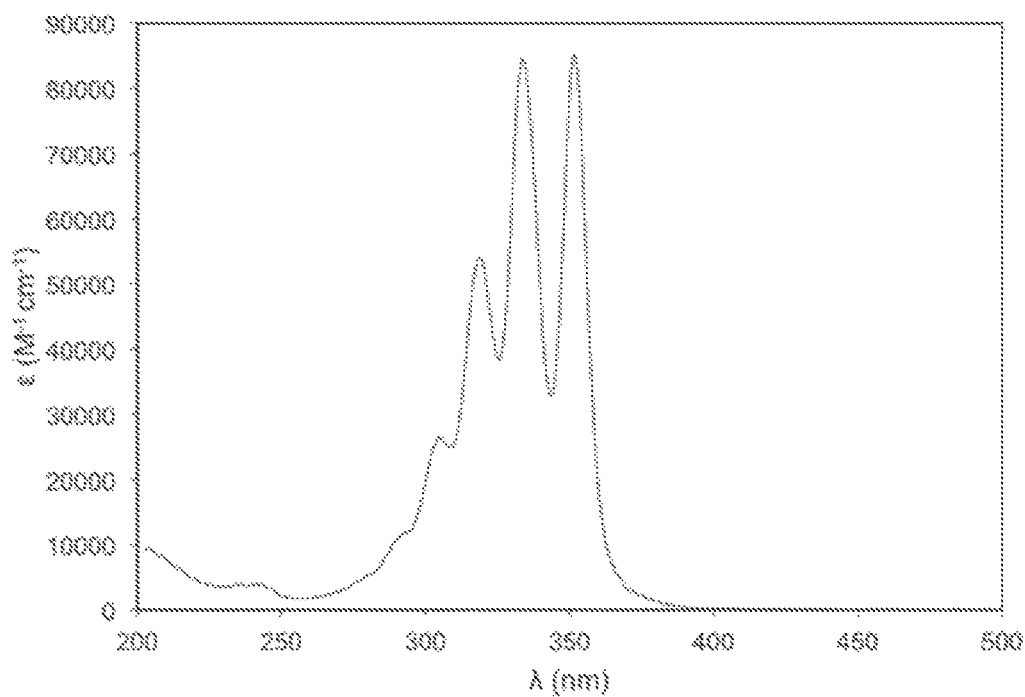
FIG. 2 shows the UV spectrum of selvamicin in methanol.

*dida albicans*. The LS1 extract was active and activity-guided fractionation was used though a $C_{18}$ cartridge followed by reverse-phase HPLC to trace this activity to a molecule with a previously unreported molecular formula of $C_{47}H_{76}O_{18}$ (high resolution ESI-MS IM-HNar calcd 951.4924, expt 951.4928). The LS2 extract was examined by high resolution LC-MS and observed the same compound, although at approximately 5-fold lower abundance, clarifying this extract's lack of antifungal activity in our initial bioassay. The active compound's UV-vis spectrum is characteristic of a polyene, with three prominent peaks (319, 334, 352 nm) consistent with a chromophore of five conjugated double bonds (FIG. 2). Subsequent NMR analysis using a variety of two-dimensional methods (COSY, TOCSY, HMBC, H2BC, and ROESY) revealed this compound to be a novel polyene macrolide, which has been named selvamicin after the site of original collection.

Figure 3:
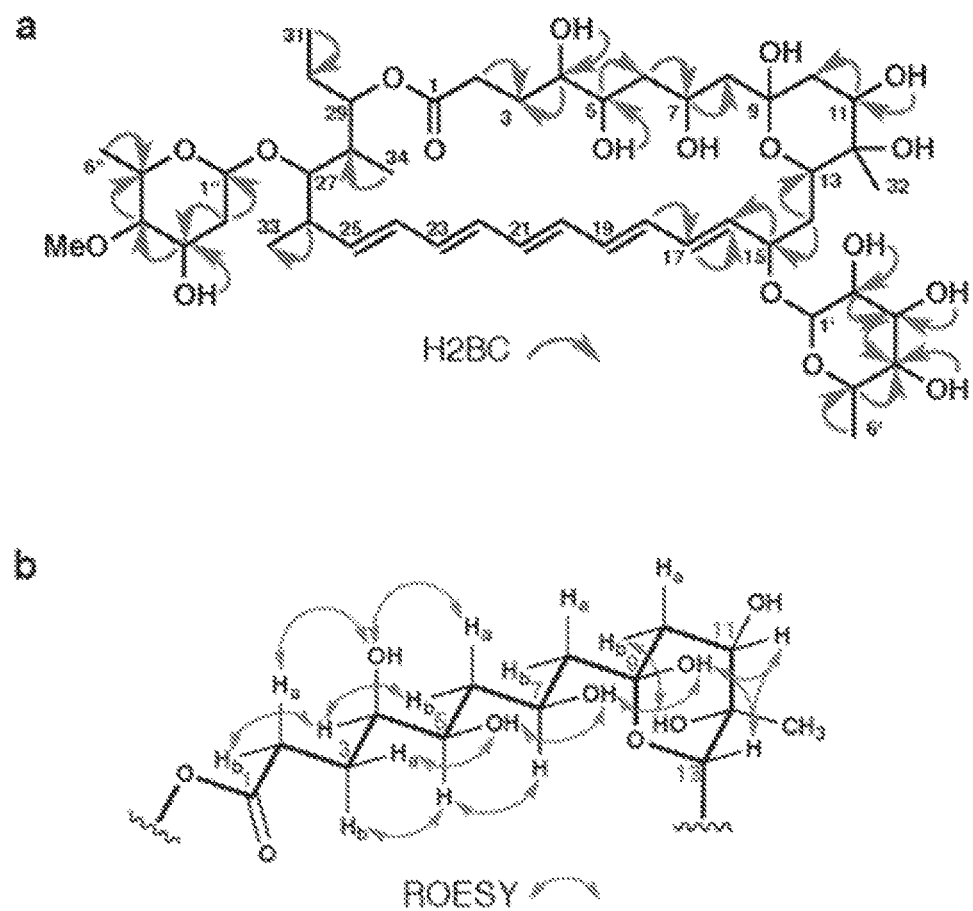
FIG. 3 includes 2 panels (Panels A and B), which show the Selvamicin NMR correlations. Panel A depicts H2BC correlations supporting the planar structure of selvamicin. Panel B depicts ROESY correlations supporting the relative stereochemistry of selvarmicin from C4-C13.

COSY and TOCSY correlations allowed construction of two major fragments of the selvamicin macrolide: one from C2-C8 and another from C13 across the pentaene to the molecule's terminus at C31 (overlap of the polyene resonances prevented definitive assignments of C19-C24). HMBC couplings link the C2-C8 fragment to quaternary carbons at either end: an ester carbonyl at C1 (172.7 ppm) and a hemiketal at C9 (97.3 ppm). The hemiketal forms a 6-membered ring established by a series of HMBC couplings from the hemiketal OH at position 9, a tertiary alcohol and methyl substituent at C12, and the other bridgehead carbon at C13. H2BC correlations support the placement of substituents along the macrolide core of selvamicin (FIG. 3). A series of ROESY correlations establish an extended geometry for the C2-C8 aliphatic chain and a chair conformation for the hemiketal ring (FIG. 3). These correlations, corroborated by available scalar coupling constants, allowed the assignment of relative stereochemistry from C4 to C13.

Figure 4:
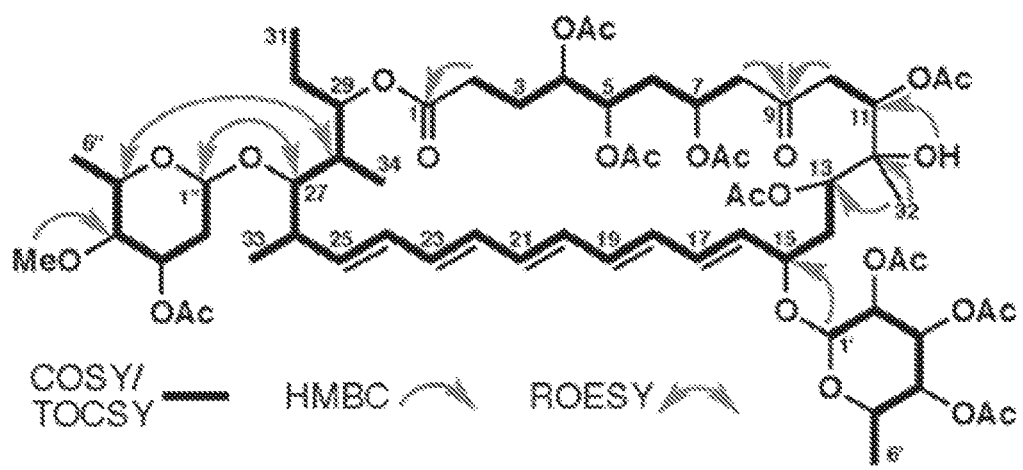
FIG. 4 depicts $Ac_9$-selvamicin NMR correlations supporting its planar structure
Figure 5:
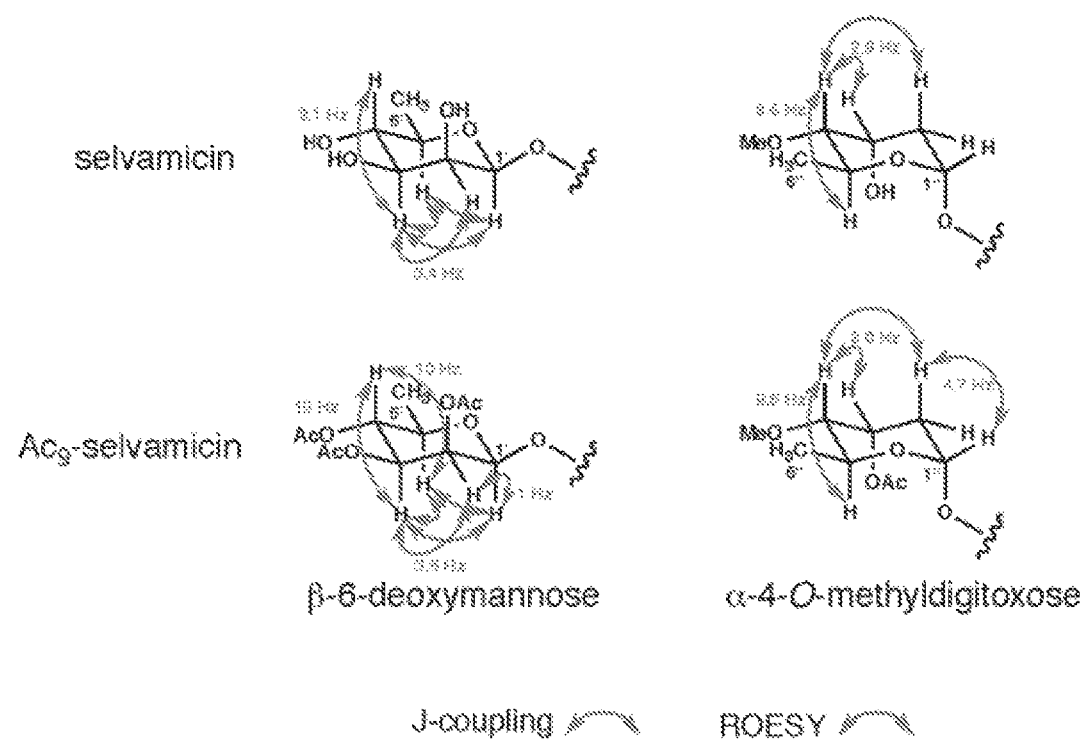
FIG. 5 depicts NMR correlations and coupling constants supporting sugar stereochemistry.
Figure 6:
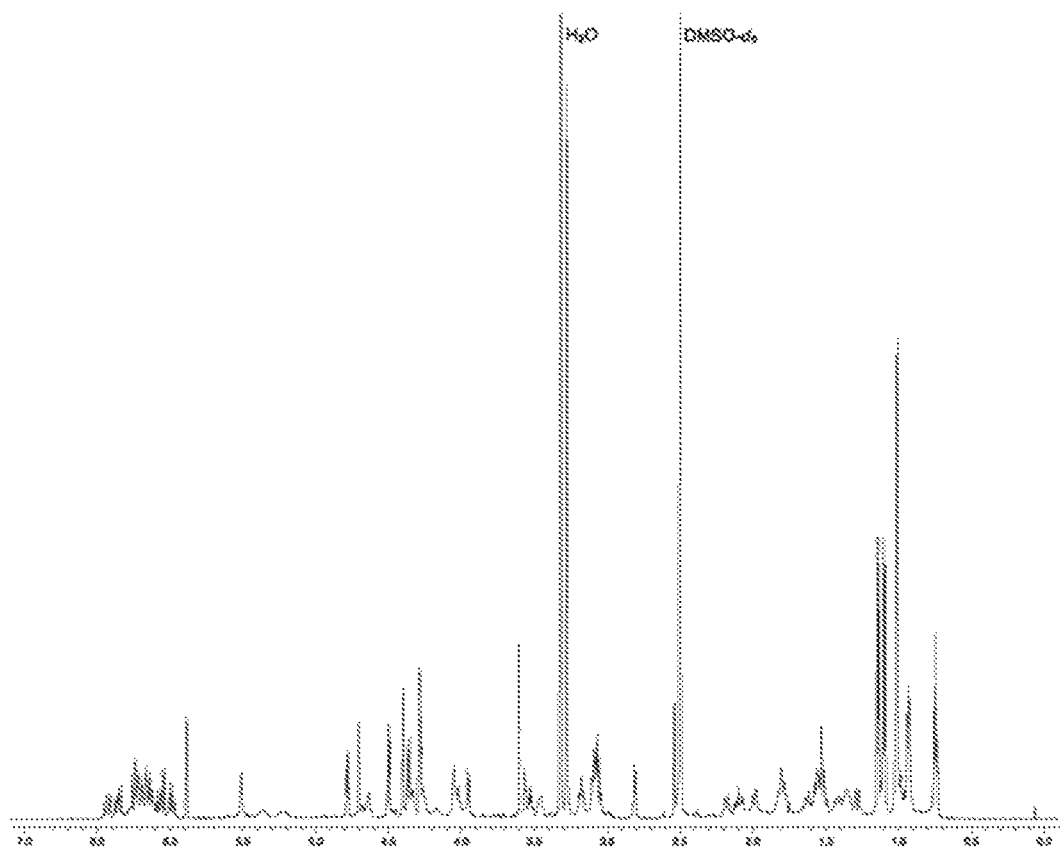
FIG. 6 includes 8 panels (Panels A-H), which show Selvamicin NMR spectra in DMSO-$d_6$. Panel A shows the 600 MHz $^1$H NMR spectrum. Panel B shows the 100 MHz $^{13}$C NMR spectrum. Panel C shows the 600 MHz COSY spectrum. Panel D shows the 600 MHz TOCSY spectrum. Panel E shows the 500 MHz ROESY NMR spectrum. Panel F shows the 600 MHz multiplicity-edited HSQC NMR spectrum of selvarmicin in DMSO-d6. CH and CH3 group correlations are shown in red and CH2 group correlations are shown in blue. Panel G shows the 500 MHz H2BC NMR spectrum. Panel H shows the 500 MHz HMBC spectrum.
Figure 6:
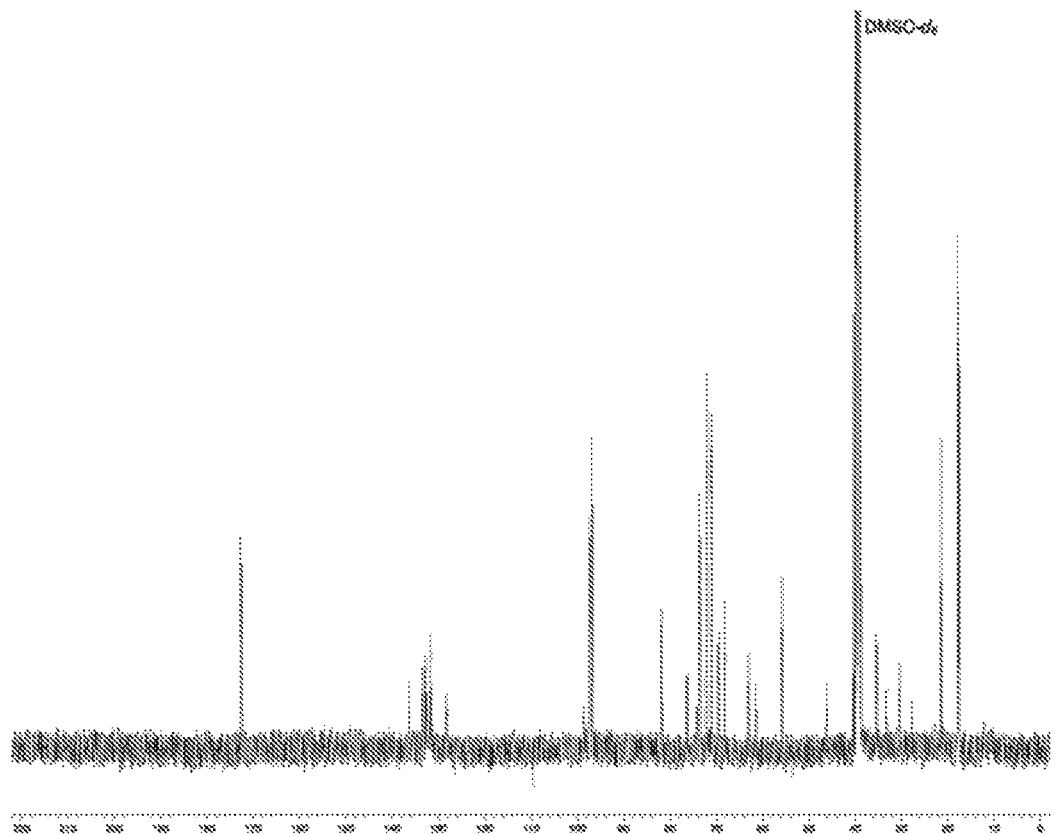
Figure 6:
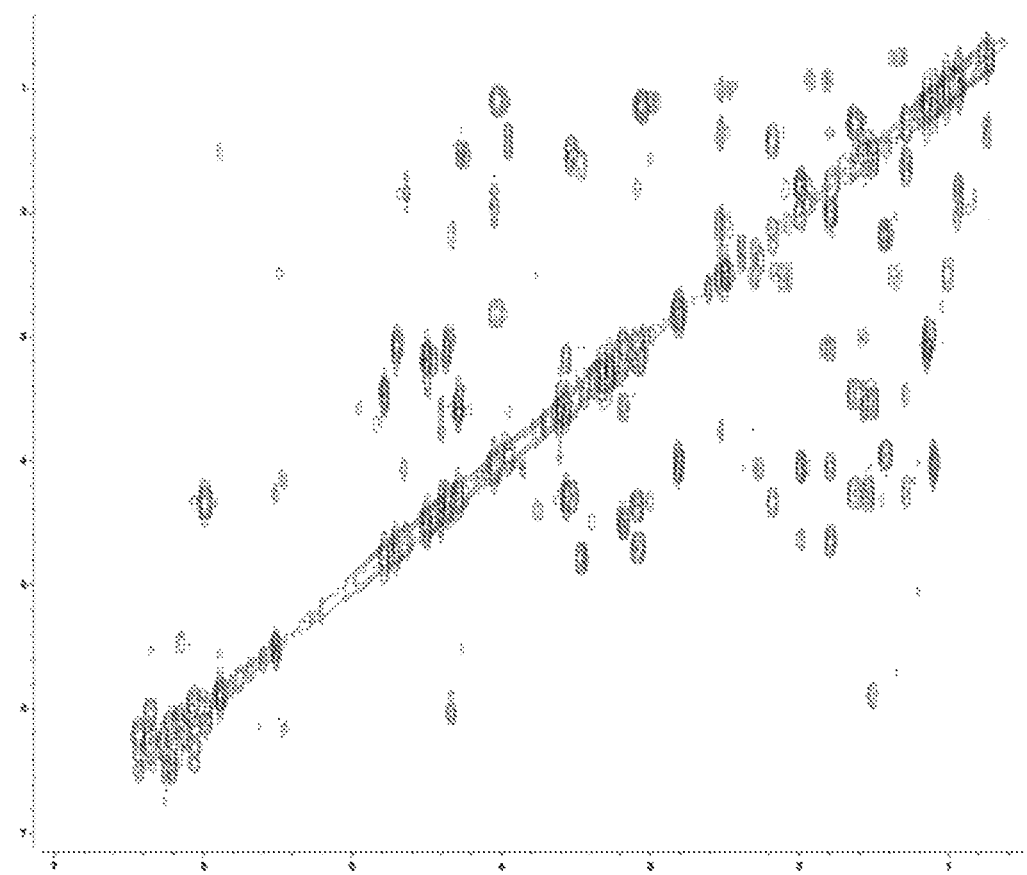
Figure 6:
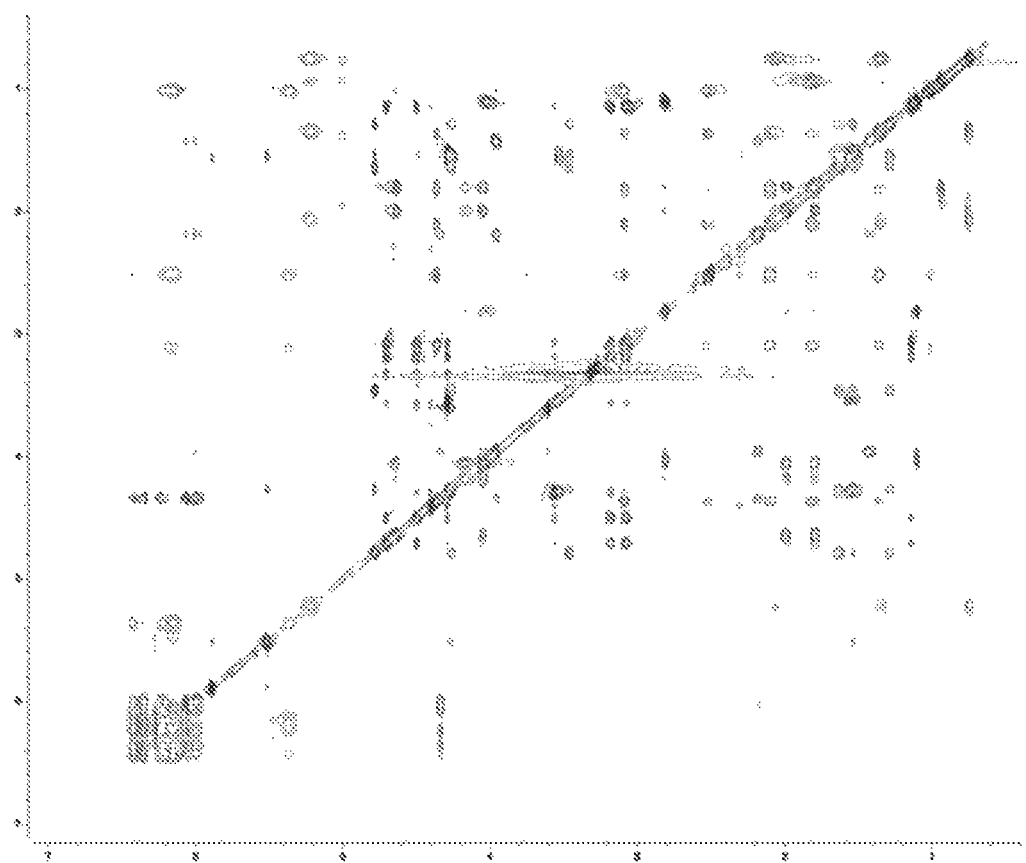
Figure 6:
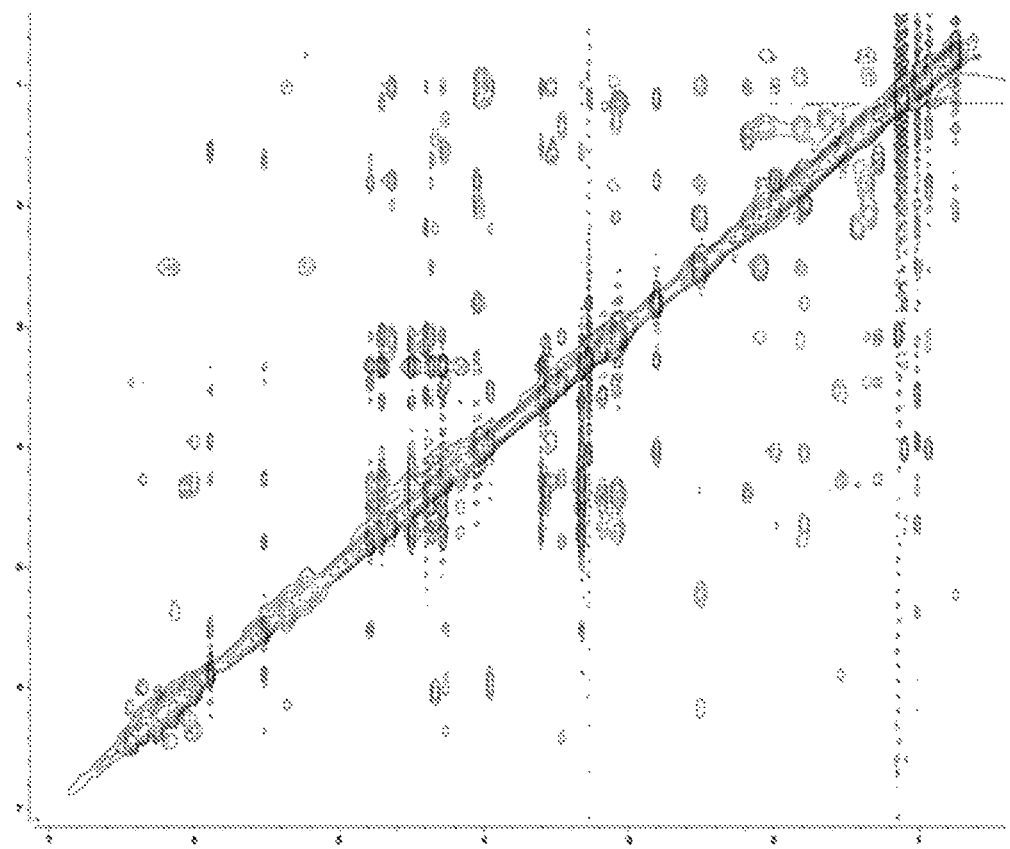
Figure 6:
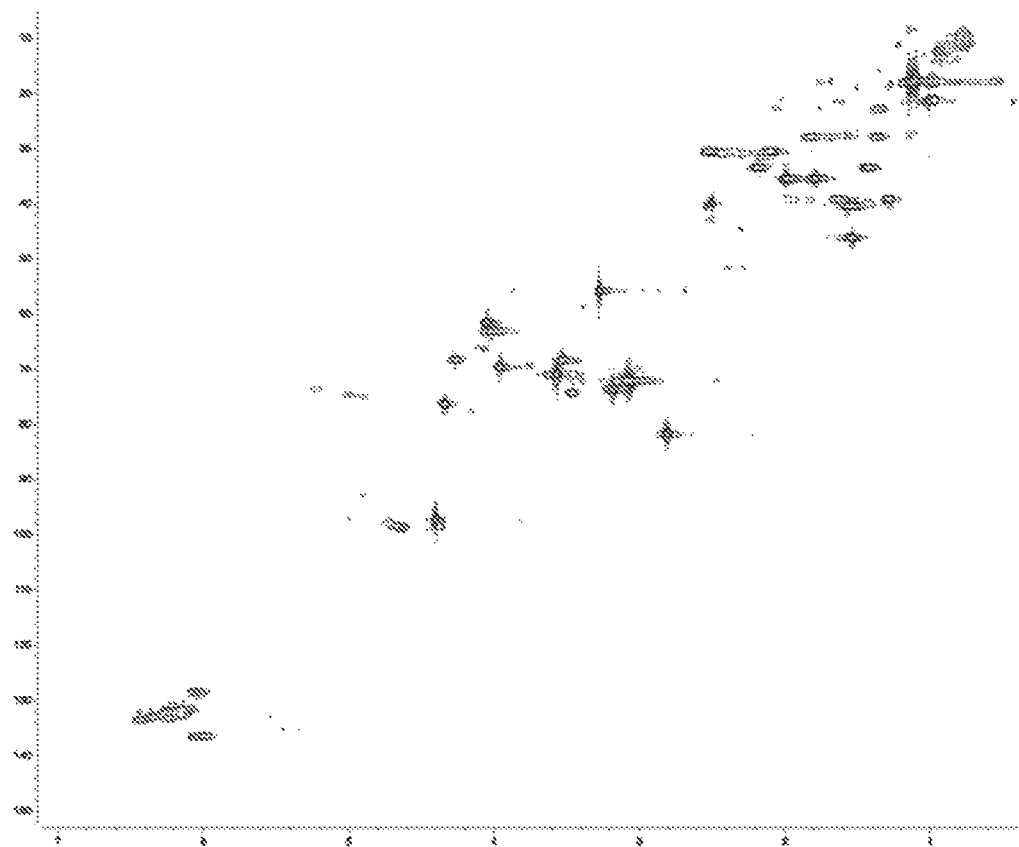
Figure 6:
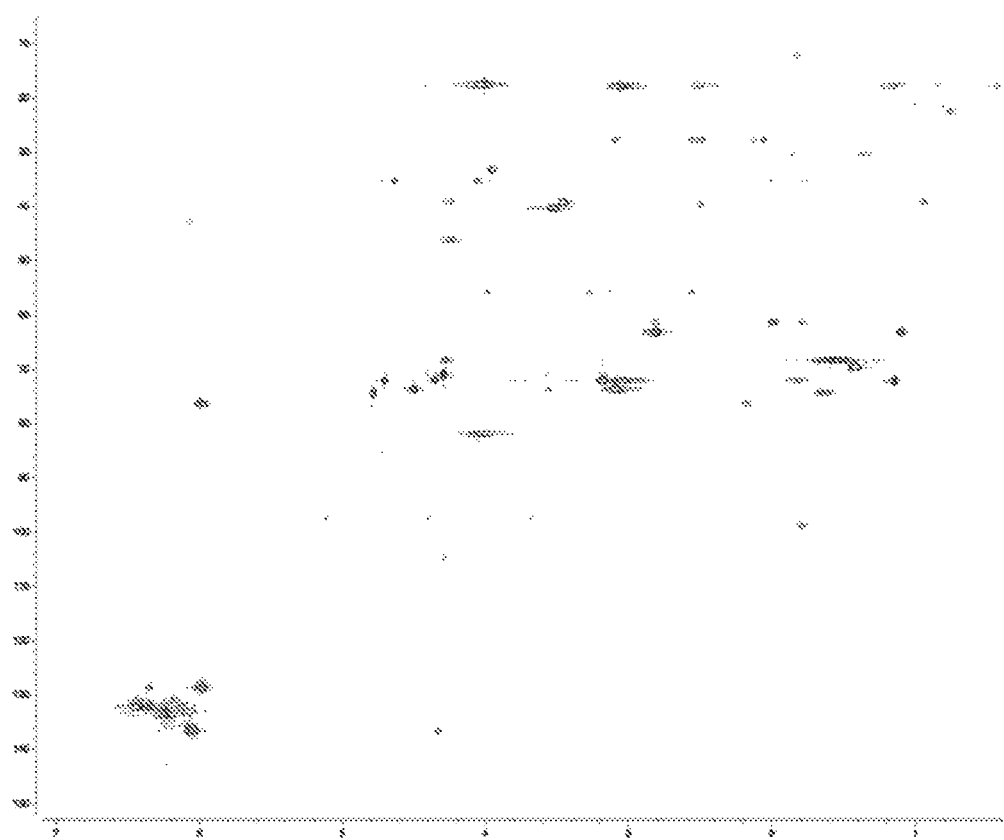
Figure 6:
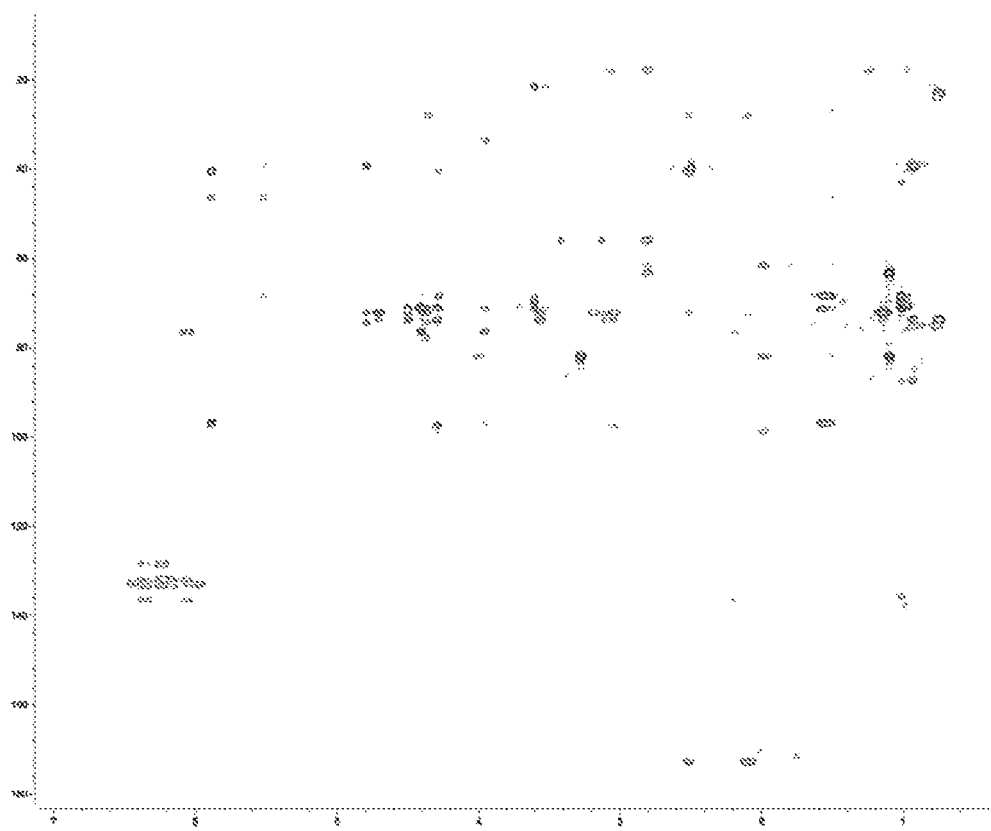
Figure 7:
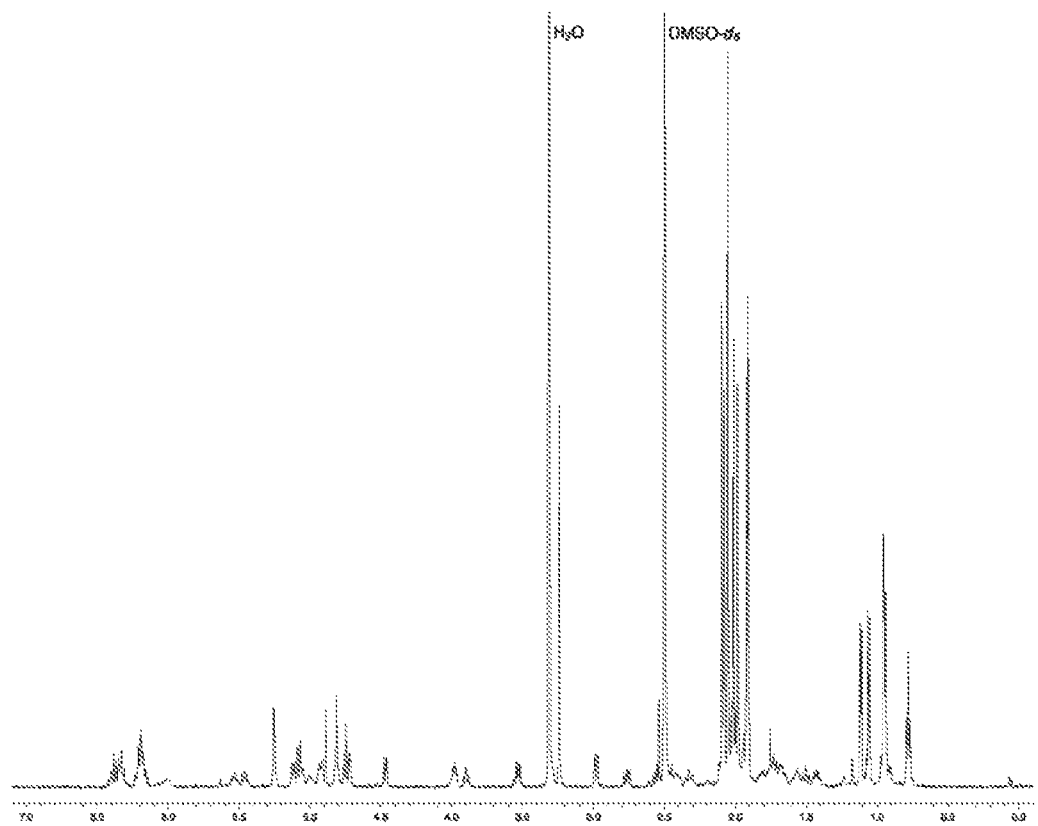
FIG. 7 includes 6 panels (Panels A-F), which show $Ac_9$-selvarmicin NMR spectra in DMSO-$d_6$, Panel A shows the 600 MHz 1H NMR spectrum. Panel B the 600 MHz COSY spectrum. Panel C shows the 600 MHz TOCSY spectrum. Panel D shows the 600 MHz ROESY NMR spectrum. Panel E shows the 600 MHz multiplicity-edited HSQC NMR spectrum of $Ac_9$-selvamicin in DMSO-$d_6$. CH and CH3 group correlations are shown in red and CH2 group correlations are shown in blue. Panel F shows the 500 MHz HMBC spectrum.
Figure 7:
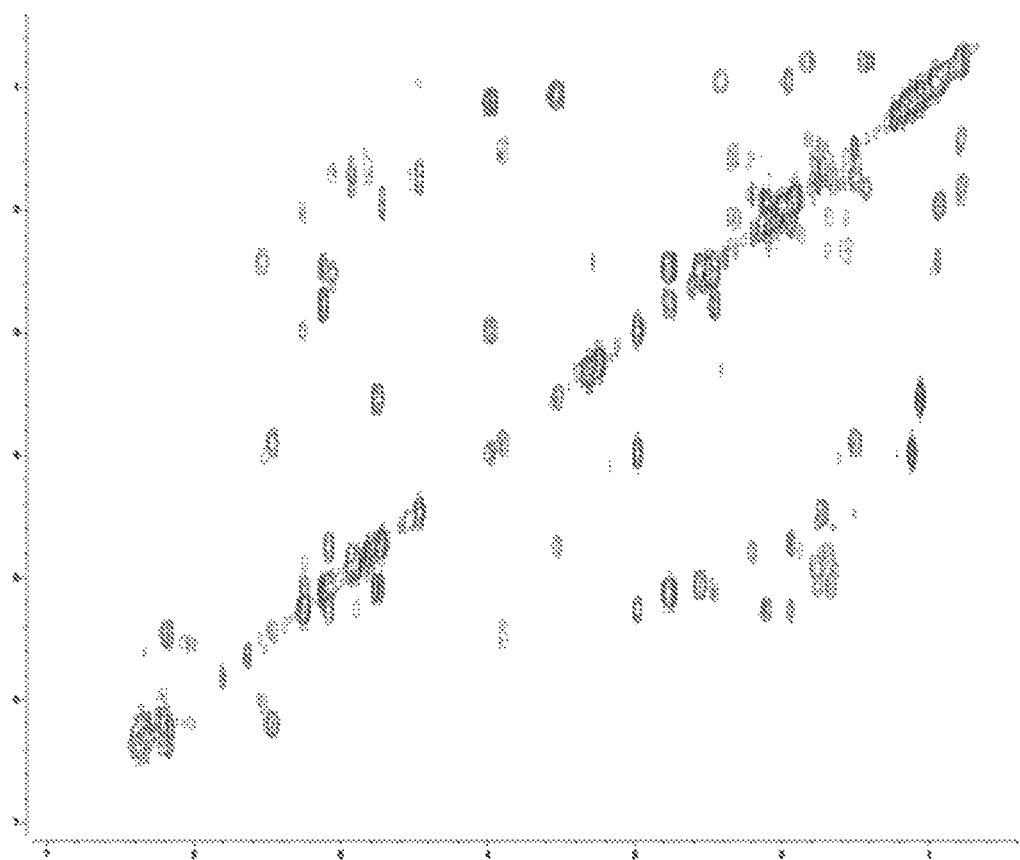
Figure 7:
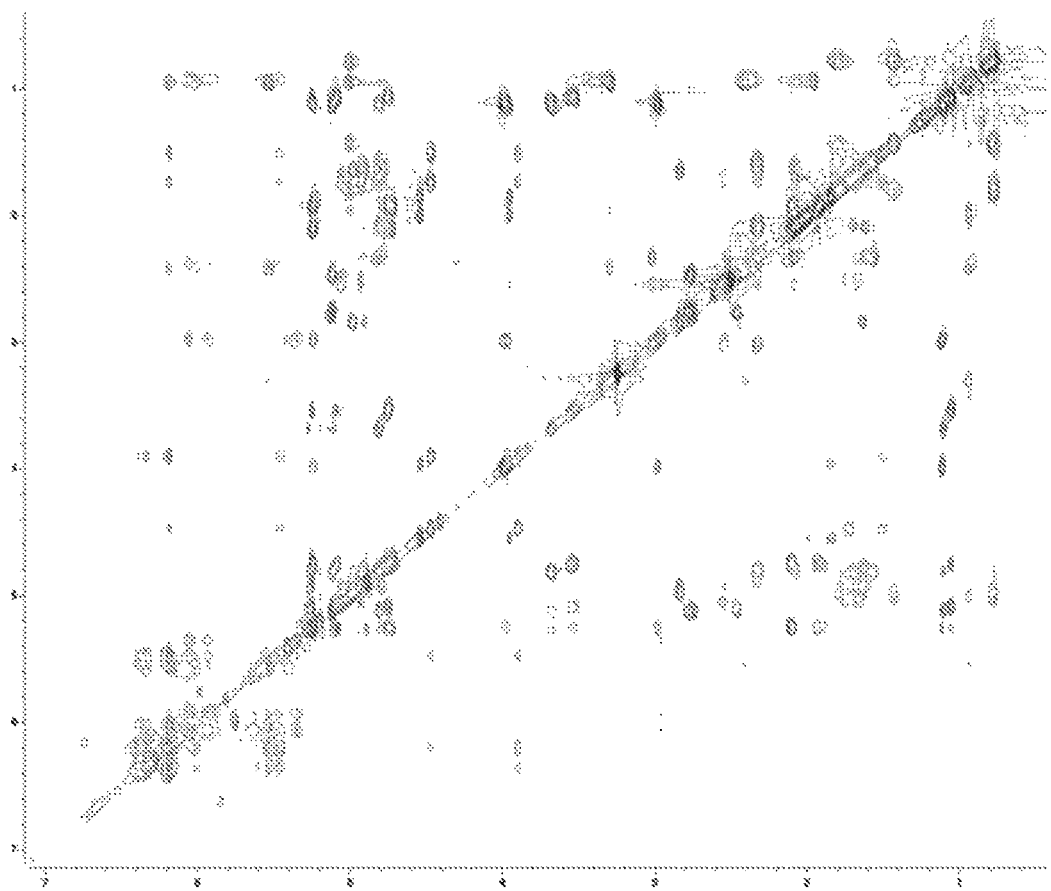
Figure 7:
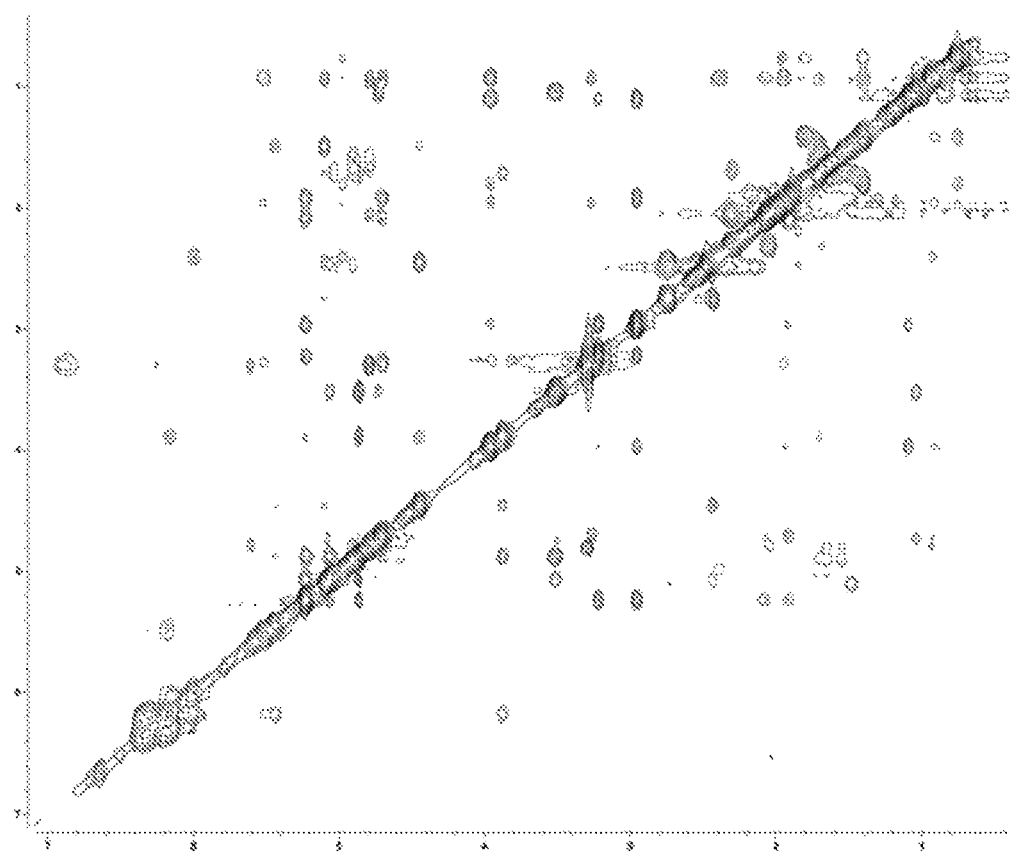
Figure 7:
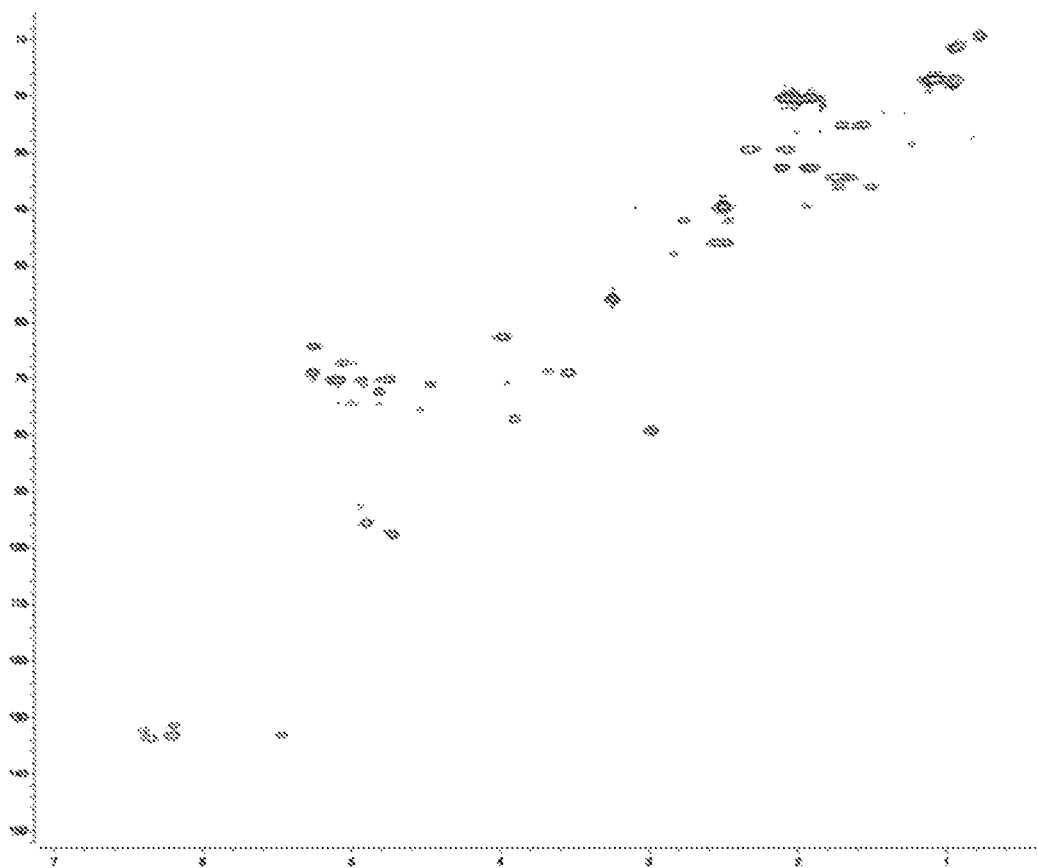
Figure 7:
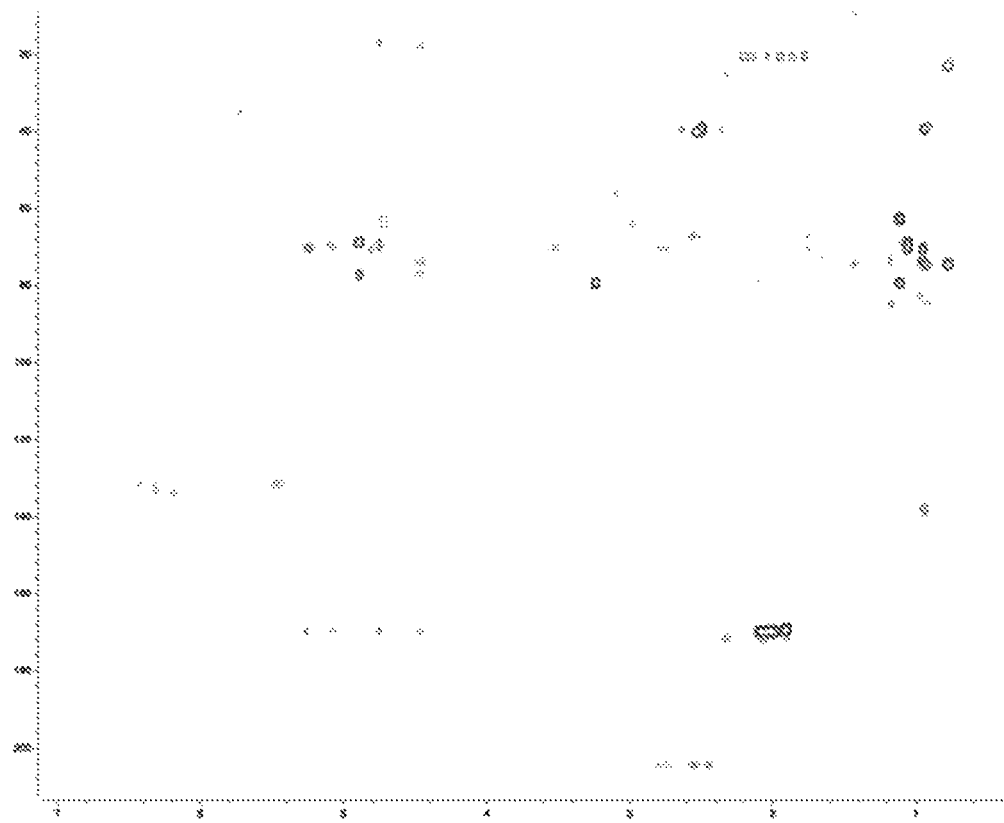

The NMR analysis also revealed two sugars in the structure of selvamicin. COSY and HMBC couplings revealed their planar structures as 6-deoxy and 2,6-dideoxy hexoses, as shown in FIG. 1, Panel B. In order to better resolve the crowded sugar CH signals and reveal additional peak fine structure, selvamicin was reacted with acetic anhydride to modify its free hydroxyl groups. In the acetylation product, the hemiketal at position 9 was instead observed as a ketone, and with the exception of the tertiary alcohol at position 12, all OH groups were acetylated (FIG. 4). Scalar couplings and ROESY correlations allowed the acetylated sugars in this product to be assigned as $(Ac)_3$-β-6-deoxymannose and Ac-α-4-O-methyldigitoxose (FIG. 5). The absolute configuration of the sugars was not determined.

A clear HMBC coupling from the anomeric proton of the β-6-deoxymannose places this sugar at position 15 of the selvatmicin macrolide (FIG. 1, Panel B). While no HMBC couplings were observed for the anomeric proton of 4-O-methyldigitoxose, a series of POESY correlations (1"-H/27-H, 1"-H/33-H, 5"-H/34"-H) locate this sugar on the opposite side of the macrolide at position 27. The $^1H$ and $^{13}C$, chemical shifts of the CH at position 27 support an oxygen substituent at this attachment point. From C25-C31, we observed broadened $^1H$ and $^{13}C$ resonances, which obscured scalar couplings to establish relative stereochemistry in this region. This peak broadening could reflect conformational exchange near the 4-O-methyldigitoxose glycosylation.

Selvamicin's structure diverges from the antifungal polyenes amphotericin B, nystatin $A_1$, and natamycin in several key respects. Its 30-membered macrolide core is intermediate in size between that of the smaller antifungal natamycin and those of amphotericin B and nystatin $A_1$. Selvamicin's unusual glycosylation is notable. The 6-deoxymannose replaces the mycosamine sugar common to most antifungal polyenes, and a second glycosylation, observed here at C27, is also unusual. Selvamicin represents, to our knowledge, the first report of either 6-deoxymannose or 4-O-methyldigitoxose sugars in a polyene natural product.

A second glycosylation located instead on the opposite end of the macrolide, as in selvamicin, has been observed among the minor fermentation products of the nystatin $A_1$ producer *Streptomyces noursei* (nystatin $A_3$. FIG. 1, and NYST1070), and the candidin producer *Streptomyces viridoflavus* (candidoin), with the second sugar located at C35, the position corresponding to selvamicin's 4-O-methyldigitoxose attachment. While structurally distinct from 4-O-methyldigitoxose, these are also 2,6-dideoxy sugars (digitoxose, mycarose, and 2,6-dideoxy-L-erythro-hexopyranose-3-ulose, respectively). Notably, in contrast to fermentations of *Streptomyces noursei* and *Streptomyces virldojlavus*, we observe the diglycosylated polyene selvamicin as the major polyene species, and neither monoglycosylated analog is detectable by LC-MS in extracts of LS1 or LS2.

The presence of 4-deoxymannose in place of mycosamine represents the only example of a non-cationic sugar at that position in a glycosylated polyene natural product. Correspondingly, the usual paired carboxylate substituent (position 16 in nystatin and amphotericin B and position 12 in natamycin) is absent in selvamicin. There is instead a methyl group and a tertiary alcohol at position 12.

Example 2

Chemical Induction Affords Large Quantities of Selvamicin

Figure 8:
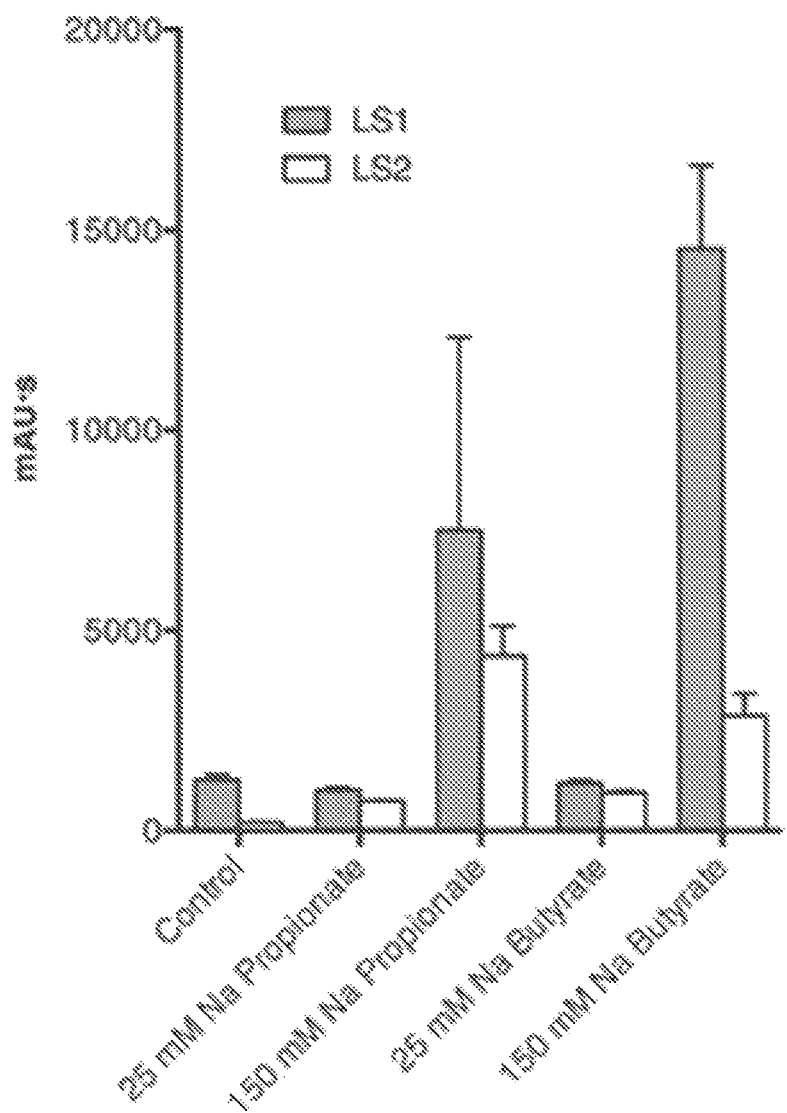
FIG. 8 is a bar graph showing the induction of selvamicin production by sodium propionate and sodium butyrate.
Figure 9:
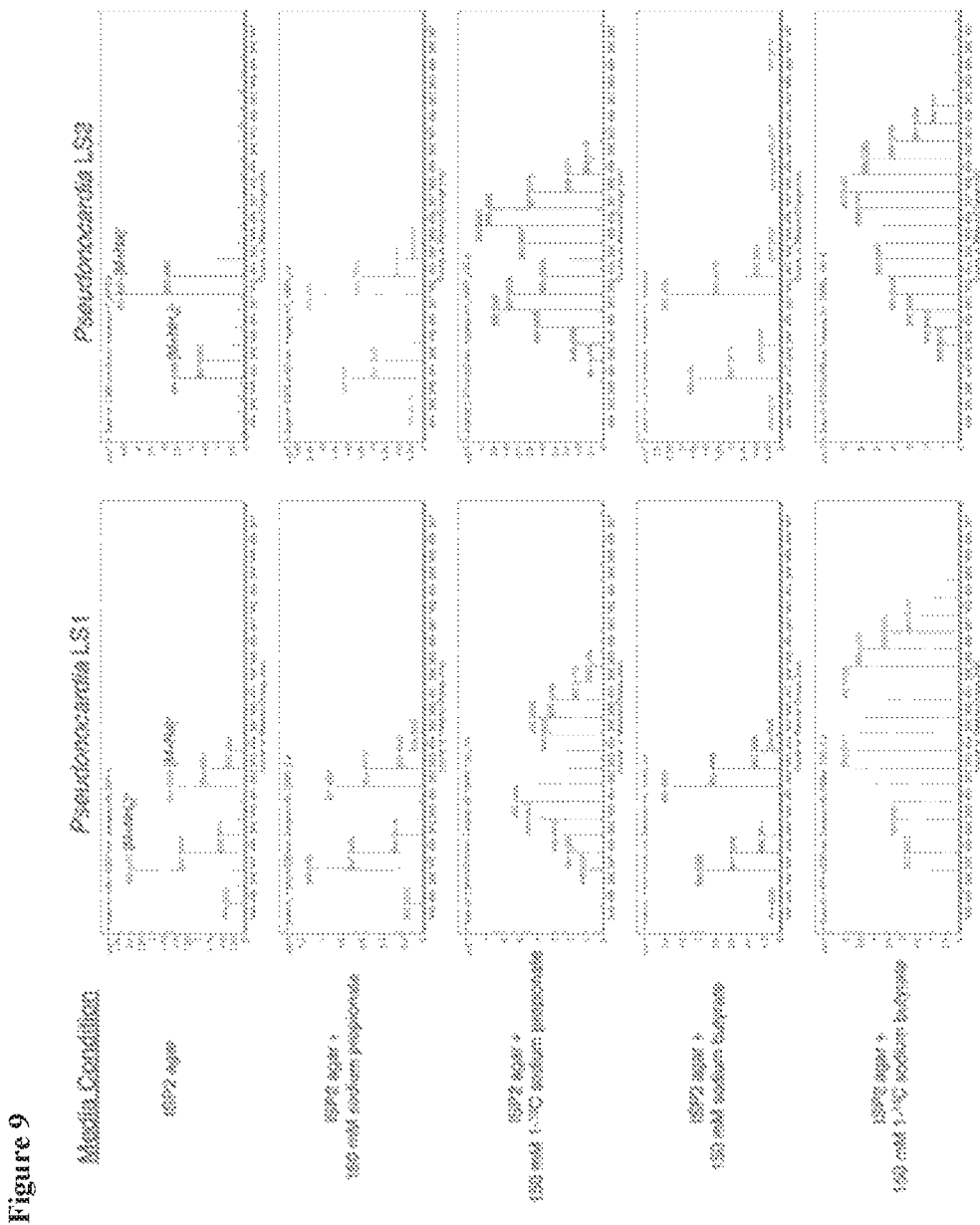
FIG. 9 is the Selvamicin mass spectra from HPLC-ESI-HRMS of Pseudonocardia culture extracts.

The initial characterization and subsequent analysis of selvamicin was aided by the availability of large amounts of the compound (ultimately >100 mg) by chemical induction of *Pseudonocardia* isolate LS1 using sodium butyrate. The addition of high concentrations of sodium butyrate (150 mM) to cultures of LS1 and LS2 increased the production of selvamicin by approximately 20-fold (FIG. 8). Using mass spectrometry, $^{13}C$ labeling of selvamicin was observed when $^{13}C$ sodium butyrate was used, indicating that butyrate can also act as a metabolic precursor (FIG. 9). Sodium propionate also upregulated production in both LS1 and LS2, and $^{13}C$ labeling also demonstrated incorporation into selvamicin.

Example 3

Antifungal Activity and Solubility

Figure 10:
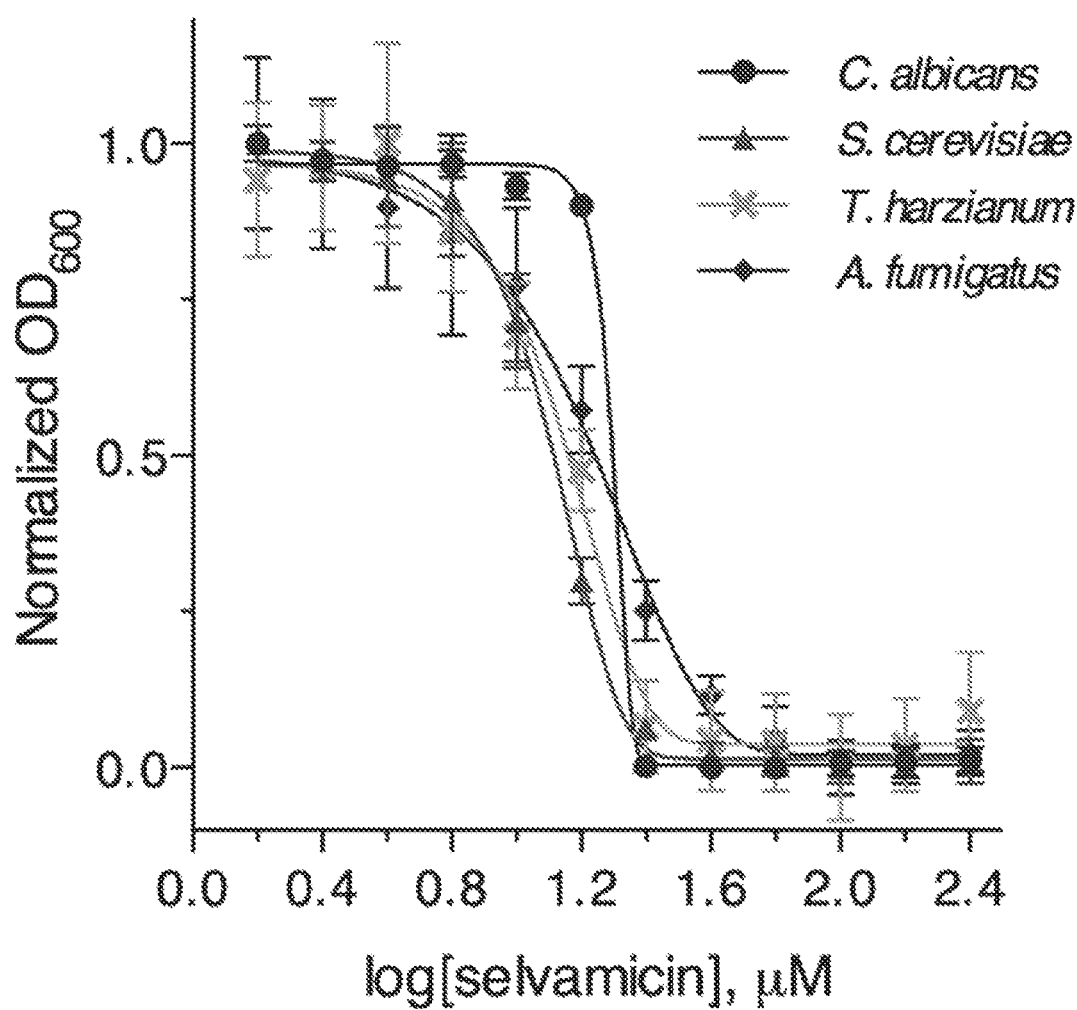
FIG. 10 is a plot showing the growth inhibition of Candida albicans, Saccharomyces cerevisiae, Trichoderma harzianum, and Aspergillus fumigatus by selvamicin.
Figure 23:
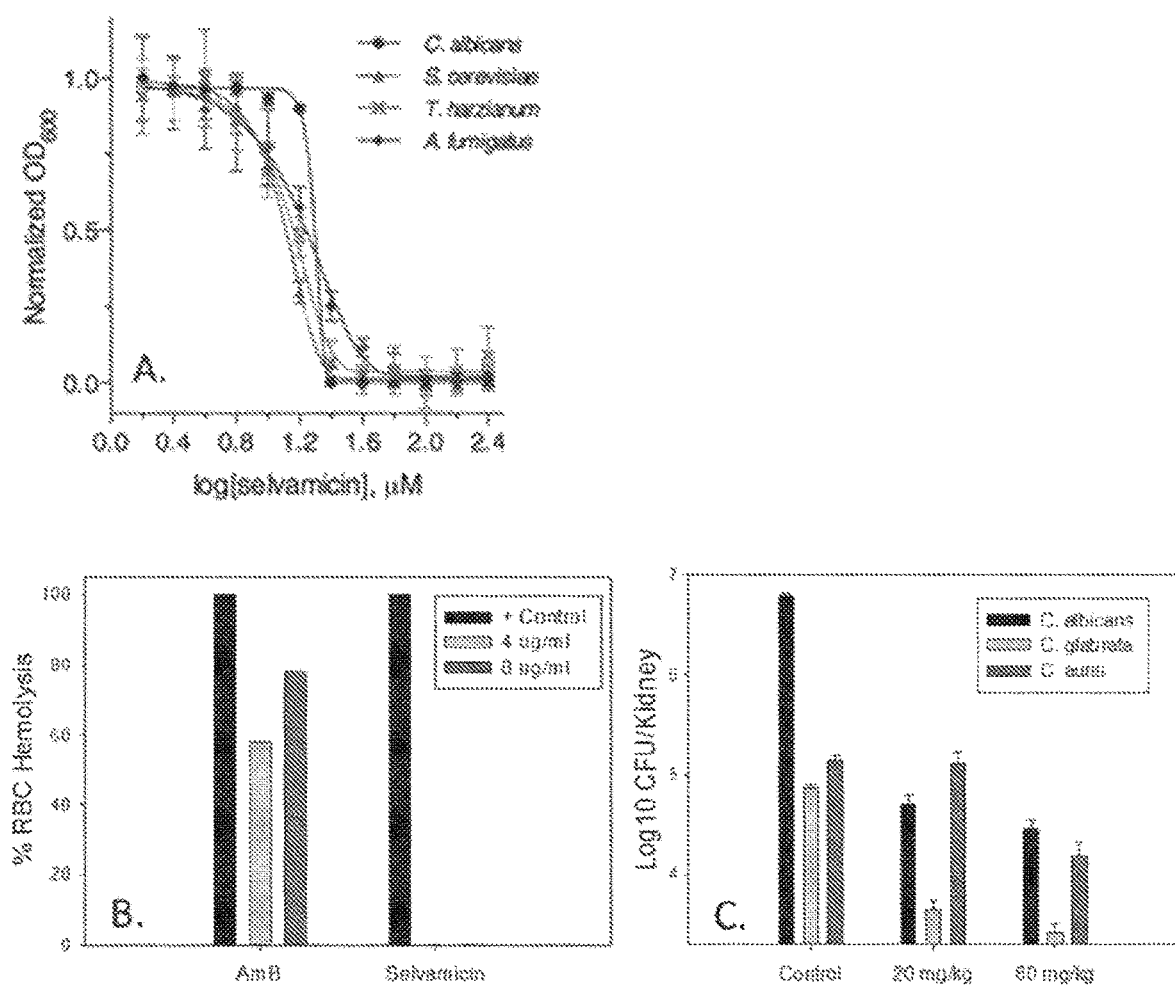
FIG. 23 shows in vitro and in vivo efficacy (Panels A and C, respectfully) and safety (Panel B AmB is amphotericin). Single intraperitoneal doses of selvamicin in the neutropenic murine disseminated candidiasis model against strains of *C. albicans, C. glabrata*, and *C. auris* are shown.

Liquid broth-based activity testing confirmed selvamicin's antifungal activity against *Candida albicans* (MEC=23 μM), with similar activity observed across a panel of fungi (*Saccharomyces cerevisiae*, *Aspergillus fumiganis*, and *Trichoderma harzianum*, FIG. 10, FIG. 21, FIG. 23, Panel A), No activity was detected against either Gram-negative (*E. coli*) or Gram-positive (*B. subtilis*, *M. luteus*) bacteria. Selvamicin has more modest antifungal activity than clinically used polyene antifungals such as nystatin $A_1$ (MIC=1.0 uM against *C. albicans*). However, it has improved aqueous solubility (2.3 mM compared to 0.3 mM for nystatin $A_1$), a major limitation of clinically available polyene antifungals. Selvamicin's improved solubility, despite its lack of charged carboxylate and ammonium groups, is probably contributed by its second sugar moiety.

Figure 13:
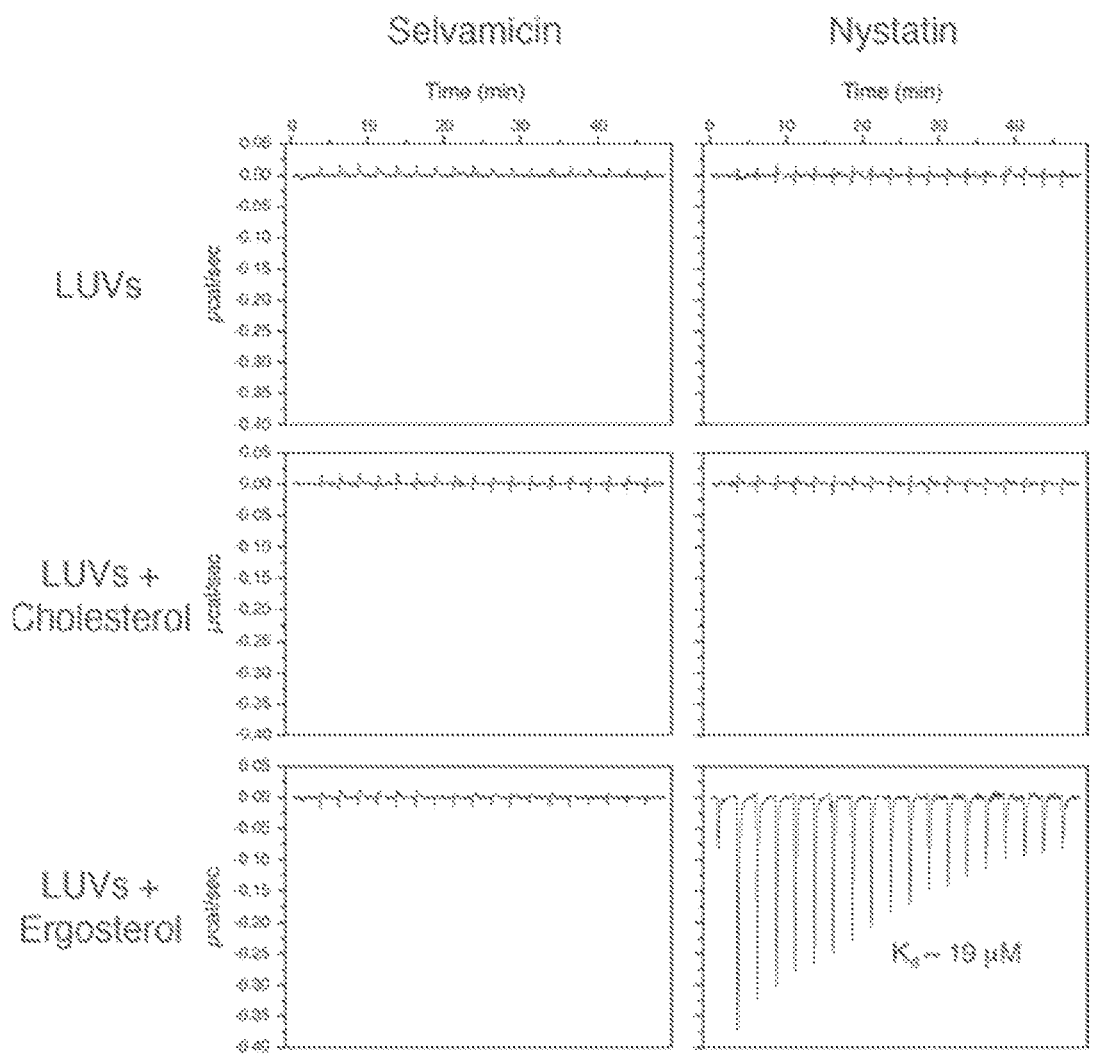
FIG. 13 shows isothermal calorimetry traces assaying polyene-sterol interactions.

The activity of known polyene antifungals derives from interactions with ergosterol, the primary sterol of fungal plasma membranes. Such interactions can compromise membrane integrity and inhibit the function of membrane proteins. Not wishing to be bound by theory, it is believed that ergosterol sequestration into extracellular aggregates may be the dominant mechanism of action, though several polyenes, including nystatin and amphotericin B, have also long been known to permeabilize membranes by the formation of ergosterol-dependent transmembrane channels. The presumed geometry of these channels situates the charged end of the molecule at the lipid-water interface, with the polyene and polyol interacting with ergosterol within the plasma membrane. The dramatically different electrostatic nature of selvatmicin would likely preclude channel formation, with a hydrophilic yet uncharged sugar at each end of the molecule. An interaction with ergosterol using an established isothermal calorimetry assay for binding to liposome-embedded ergosterol was probed. These experiments showed no evidence for binding, in stark contrast to control experiments using nystatin $A_1$, suggesting that this interaction is much attenuated if present at all (FIG. 13).

Example 4

Biosynthetic Gene Cluster

To understand the genetic origins of selvamicin biosynthesis, the genomes of Pseudonocardia isolates LS1 and LS2, sequenced using PacBio technology, were examined. A large type I PKS gene cluster was identified in both genomes that satisfies the biosynthetic requirements for selvamicin (FIG. 11). The 109 kbp selvamicin biosynthetic gene clusters (BGC) from each isolate share perfect synteny and 98.4% nucleotide identity over their length. In contrast, the whole genomes differ more substantially. The average nucleotide identity (ANI) calculated across conserved replicons on both chromosomes is only 83% and a comparison of housekeeping gene sequences places LS1 and LS2 into distinct clades previously established for ant-associated Pseudonocardia. Overall, the two BGCs are much more similar to one another than are their bacterial hosts.

Surprisingly, the selvamicin BGC is situated in completely different genomic contexts in the two selvamicin producers; in LS1 it resides on the 6.1 Mbp circular chromosome, while in LS2 it is on a 376 kbp plasmid, pLS2-1 (FIG. 11, Panel A). The presence of an identical BGC in two divergent Pseudonocardia isolates, and in different genomic contexts, points to recent horizontal transfer. In keeping with recent movement of this cluster, it is flanked by numerous mobile genetic elements in both genomes, including transposases and integrases (FIG. 11, Panel B). Such genes are prevalent across both genomes. On the pLS2-1 plasmid containing the selvamicin BGC, an impressive 24% of all RAST-annotated genes are mobile genetic elements.

Plasmid-encoded secondary metabolite biosynthesis in several other ant-associated Pseudonocardia. These plasmids are an unmatched source of genetic, chemical, and functional diversity. For example, an additional plasmid-borne cluster that encodes for an antibacterial rebeccamycin analog is thought to mediate niche defense between otherwise nearly indistinguishable Pseudonocardia. In contrast, here, a plasmid and a recent chromosomal insertion in two distinct bacterial isolates that represent convergence on an unusual polyene macrolide was identified. These results mirror those observed for the gemmycins, cyclic depsipeptides of unknown function. Both selvamicin and gerumycin BGCs are found on the LS1 chromosome though in other strains they are found on plasmids. Overall, these observations continue to implicate plasmid-based genetic exchange between these bacterial sytnbionts and the environment with the Pseudonocardia acting as a reservoir for mobile BGCs that encode useful biological activities.

Example 5

Biosynthesis

Figure 14:
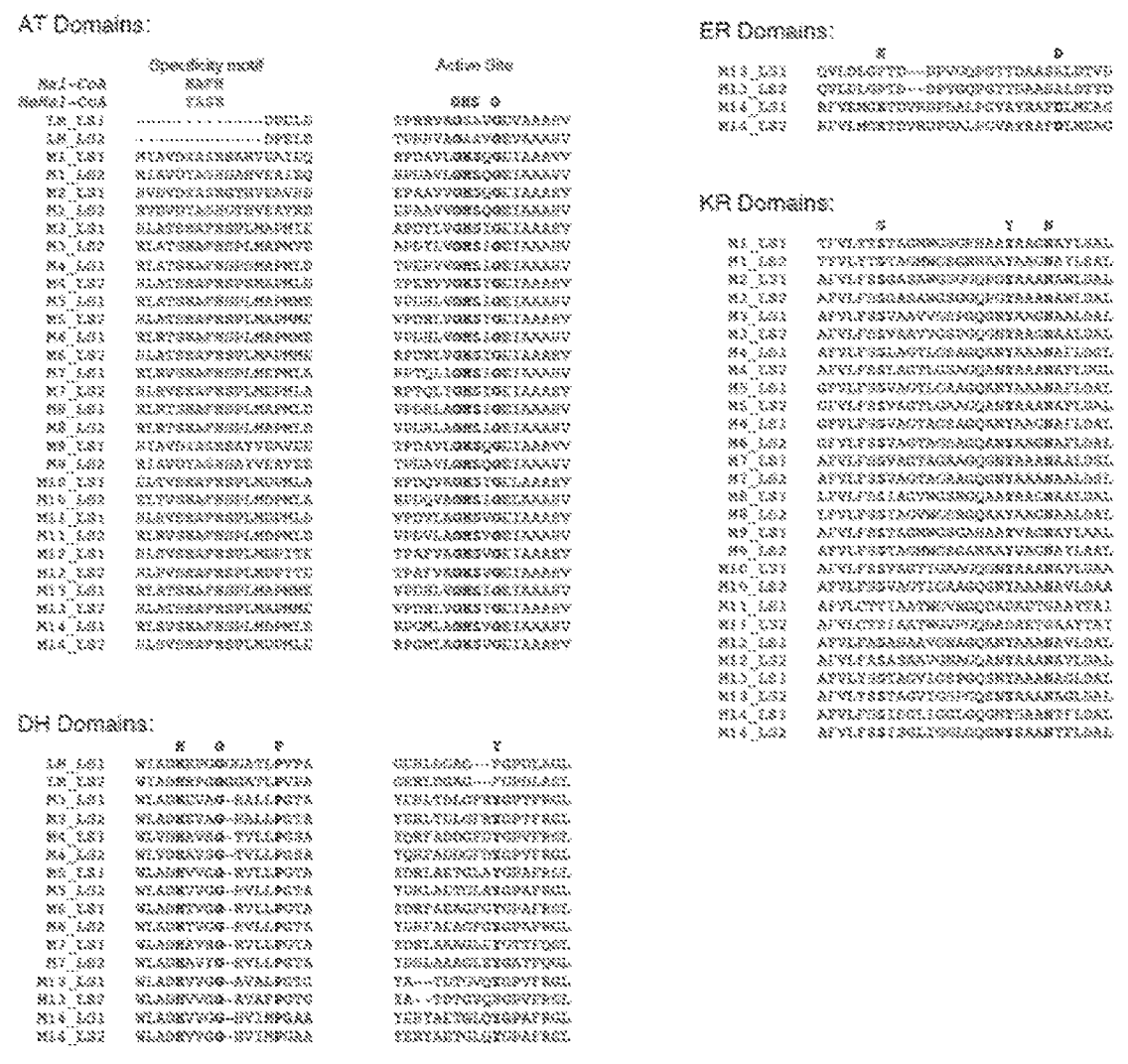
Figure 15:
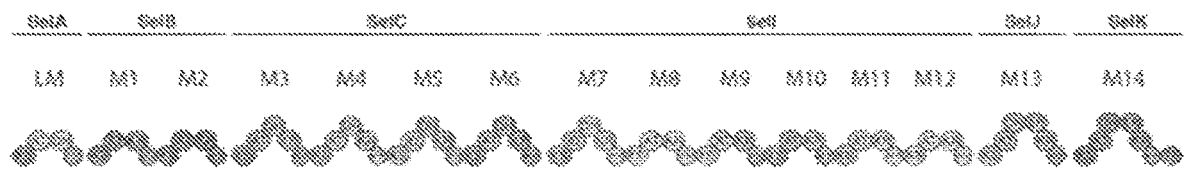
FIG. 15 is a schematic of selvamicin PKS domain architecture. Putative inactive domains are shaded gray.
Figure 22:
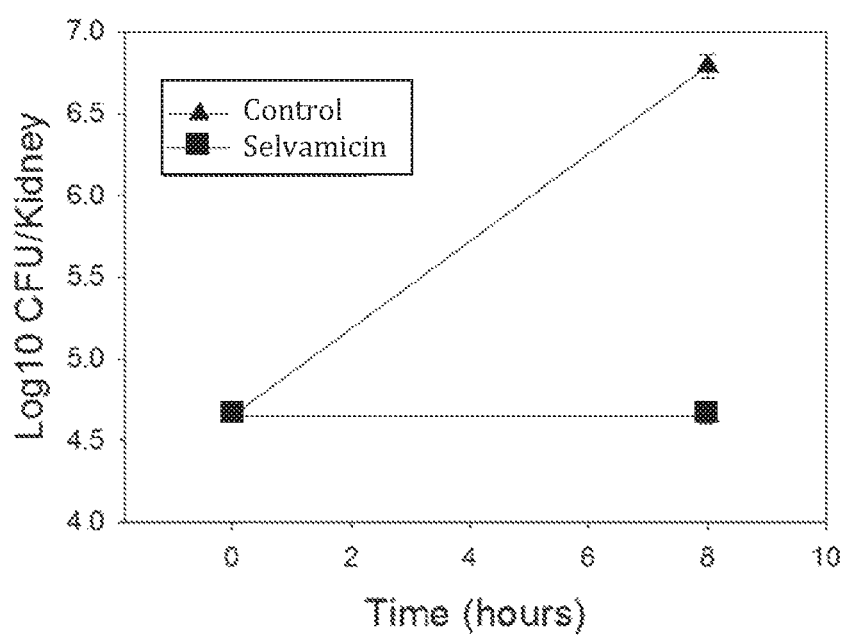
FIG. 22 is a plot showing the in vivo antifungal activity of selvamicin.

The selvamicin cluster resembles known type I PKS-derived polyene BGCs, and a side-by-side comparison with the well-characterized nystatin BGC readily reveals the origins of selvamicin's unusual structural features (FIG. 12). Both natural products derive from type I iterative PKSs with polyketide elongation modules spread across five genes (sellnysB, -C, -I, -J, and -K). Relative to the corresponding genes for nystatin, selC and selJ each lack two PKS modules, corresponding to the observed four-carbon truncations of selvamicin's polyene and polyol moieties opposite one another on the macrolide: The polyketide backbone of selvamicin can be traced through 14 PKS modules with ketoreductase (KR), dehydratase (DH), and enoylreductase (ER) domains dictating the oxidation state of each malonyl or methylmalonyl unit (FIGS. 14 and 15). As often observed in type I PKS modules, there are several presumably inactive vestigial domains with mutations and/or truncations at their active sites: a DH and ER in module 13 and a KR in module 11.

SelA, the putative PKS loading module for selvamicin's propionate starter unit, shares several unusual features with previously characterized polyene loading modules, the function of which are poorly understood. Unlike most type I PKS loading modules, SelA is a separate protein distinct from the first elongation module and a serine is found in place of the canonical KS active site cysteine. Like NysA, the nystatin loading module critical for initiation of its biosynthesis. SelA contains a presumably inactive DH domain with no obvious function. Most unusual, and without precedent in polyketide loading modules, the SelA AT domain lacks the critical active site histidine and has a large truncation of approximately 65 amino acids in the middle of the domain (FIG. 14), suggesting that an alternative means of loading the initial acyl starter unit may be operative.

Tailoring of the polyketide core of selvamicin requires hydroxylations at C4 and C12. SelL, a cytochrome p450 with homology to the p450 NysL that installs nystatin's C10 hydroxyl, is the most probable oxidase for C4. SelP, a 2-oxoglutarate-dependent oxygenase with homology to phytanoyl-CoA dioxygenases was also identified. No homologous enzyme has been observed in other polyene clusters and this oxidase could be responsible for selvamicin's unusual C12 hydroxylation.

The canonical paired carboxylate and ammonium in polyene antifungals are both lacking in selvamicin. Notably, both the p450 NysN and ferredoxin NysM believed to install nystatin's carboxylate at C16 are absent in the selvaimicin cluster, consistent with selvamicin's unoxidized methyl substituent at C12. The aminotransferase responsible for ammonium installation on the mycosamine sugar, NysDII, is also absent from the selvamicin cluster. The remaining sugar-related enzymes in the nystatin BGC, the mannose 4,6- dehydratase NysDIII and the glycosyltransferase NysDI, both have homologs in the selvamicin cluster and are consistent with the 6-deoxymannose found at C15.

Scheme 2: Proposed reactions carried out by the selvamicin 4-O-methyldigitoxose sugar subcluster

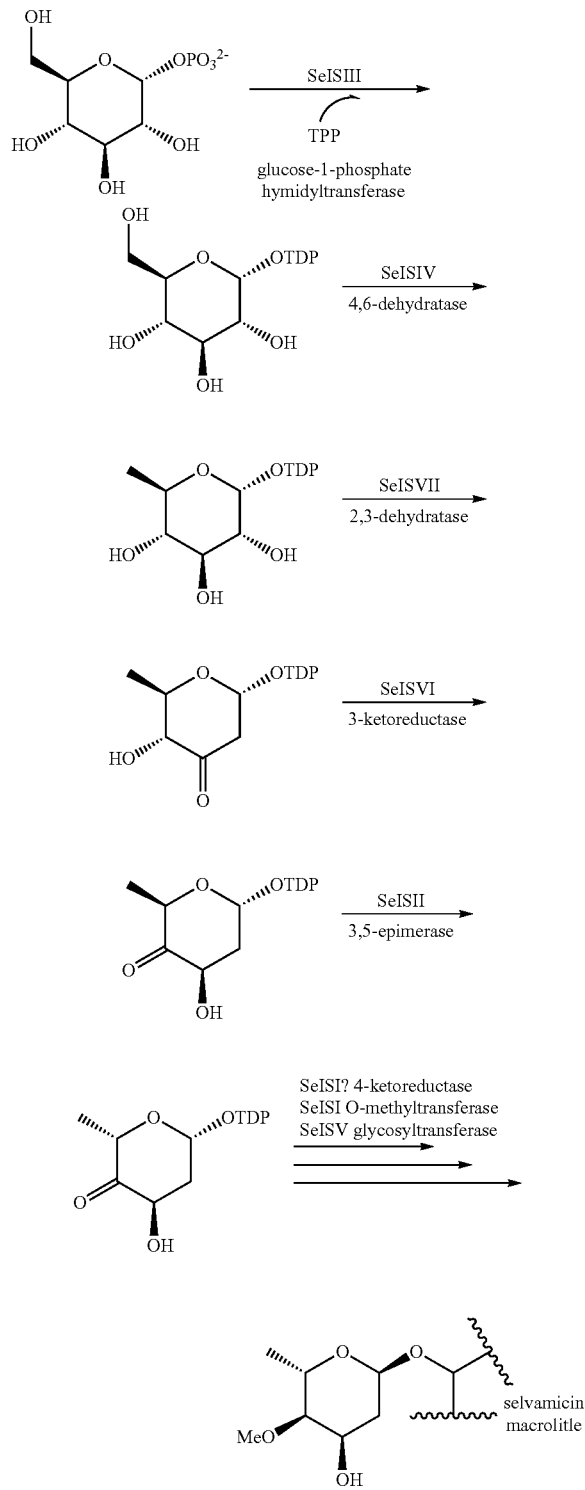

The most significant divergence from nystatin's BGC is a subcluster of seven sugar biosynthesis genes, selSI though selSVII, found in the middle of the selvamicin BGC. These include a glycosyltransferase gene, selSV, and six genes consistent with 4-O-methyldigitoxose biosynthesis as a TDP-sugar from glucose-1-phosphate (Scheme 2). The putative 4-O-methyldigitoxose biosynthesis proteins are homologous to a similar suite of proteins responsible for digitoxose biosynthesis in the BGC for jadomycin B in *Streptomyces venezuelae* ISP5230. However, the selvamicin sugar subcluster additionally contains an O-methyltransferase gene selSI), and it curiously lacks an NDP-sugar 4-ketoreductase which should be required for digitoxose formation. Recently, 4-ketoreductase activity has been reported for a bifunctional SAM-dependent methyltransferase involved in the biosynthesis of methramycin's sugars. Similar bifunctional activity could be operative for the SelSI methyltransferase or alternatively this activity could require a separate 4-ketoreductase outside the selvamicin BGC in both the LS1 and LS2 genomes.

This sugar subcluster's insertion within a cluster of familiar polyene biosynthetic genes fits well with the paradigm of modular subclusters recombining over the course of natural product evolution to generate new products. Presumably, a similar suite of genes synthesizes and attaches the digitoxose sugar to nystatin $A_3$, though no such subcluster occurs in the nystatin BGC from *Streptomyces noursei*. Whole genome sequencing of this strain may eventually reveal the location of these genes. Nystatin A3'S occurrence as a minor product of the nystatin BGC contrasts with selvamicin's occurrence as the principal product of the selvamicin cluster. The 4-O-mcthyldigitoxose subcluster's incorporation into the selvamicin BGC likely reflects selection for diglycosylation in the principal product. If this subcluster is truly modular it should present a biosynthetic engineering opportunity for appending 4-O-methyldigitoxose to other polyene scaffolds. Encouragingly, diglycoslated nystatin analogs, currently available only as minor products from *Streptomyces noursei* fermentation, have comparable anti-*Candida* potency to nystatin $A_1$. A boost in solubility from an additional sugar would address a major pharmacological limitation of antifungals such as nystatin $A_1$ and amphotericin B.

Example 6

Creation of Solubility-Improved Polyene Antifungals Using Selvamicin's Subcluster of Sugar Biosynthetic Genes (Prophetic)

The subcluster of sugar biosynthesis genes found in selvamicin's biosynthetic gene cluster (SelSI-SelSVII, FIG. 12) should contain all genes required to synthesize the sugar 4-O-methyldigitoxose and attach it to a polyene macrolide. It is predicted that this suite of genes could be transferred to the producing organism of a structurally related polyene antifungal and would act in the same fashion, allowing for the creation of new glycosylated analogs of existing antifungal agents. Glycosylation should increase aqueous solubility, which is currently a major limitation of the clinically important antifungals amphotericin B and nystatin $A_1$, shown below:

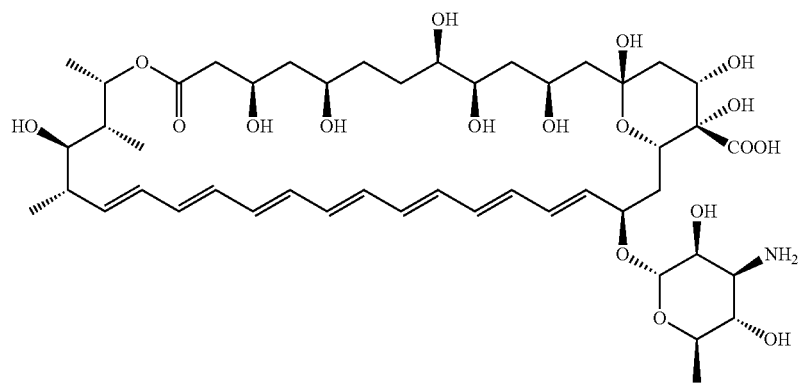
Amphotericin B
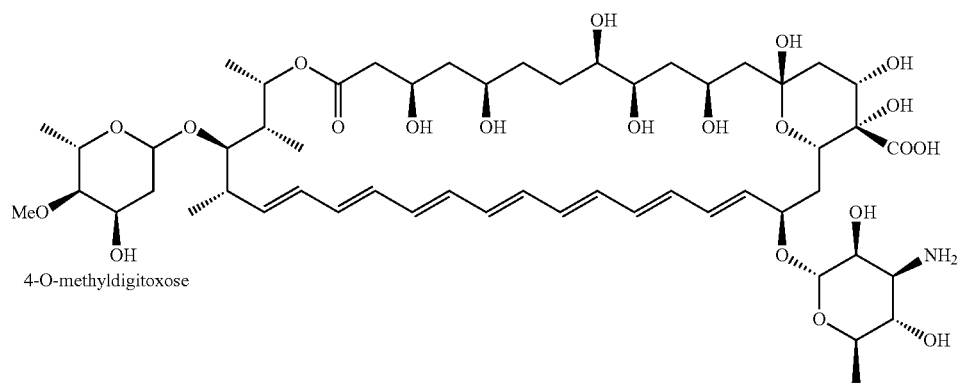
4-O-methyldigitoxose
Amphotericin analog
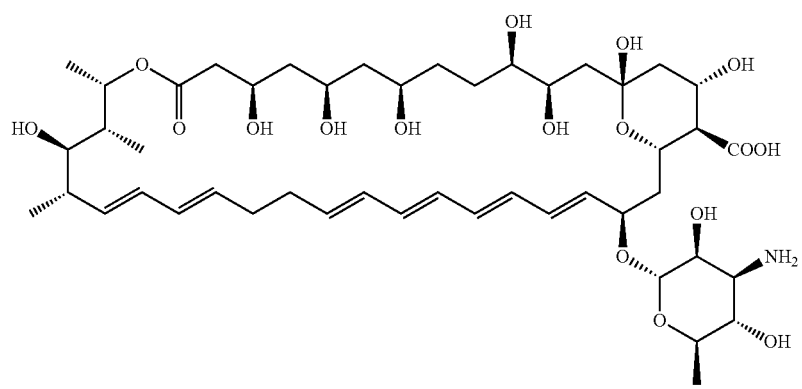
Nystatin A$_1$
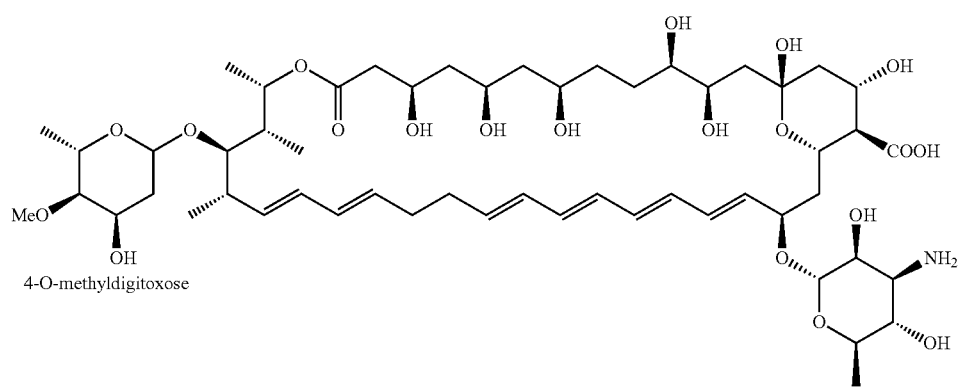
4-O-methyldigitoxose
Nystatin analog

Example 7

Generation of Non-Natural Selvamicin Analogs (Prophetic)

Non-natural analogs of selvamicin may be generated with retained or possibly improved antifungal activity by manipulating its biosynthetic gene cluster using gene knockouts. There are many possibilities here, including knockouts of the oxidases SelP or SelL to yield analogs lacking hydroxyl substituents at C4 or C12, respectively.

Selvamicin is a type I polyketide natural product whose macrolide core is generated by the iterative action polyketide modules. The types of domains comprising each module dictate the final polyketide structure, as depicted in FIG. 16, Panel A.

Selvamicin analogs could be generated by deleting or disrupting individual modules (rather than entire genes), an approach that has been widely used to generate analogs of other polyene natural products. In one example, the ketoreductase domain of module 13 could be disrupted to generate analog 1 shown in FIG. 16, Panel B.

In another example, the dehydratase domain of module 14 could be disrupted to generate analog 2 shown in FIG. 16, Panel C.

Example 8

Selvamicin In Vivo Antifungal Activity

Selvamicin was tested in the neutropenic mouse disseminated candidiasis model. Briefly, mice were infected with an inoculum of 5.70 log 10 cfu/ml of *Candida albicans* K1. Two hours after infection, the mice were administered either saline or selvamicin at 80 mg/kg via the intraperitoneal route. Eight hours after therapy, the burden of *Candida albicans* in mouse kidneys was measured by viable plate counts of organ homogenates. Selvamicin demonstrated efficacy in preventing *Candida albicans* growth following a single administration. No animal toxicity was apparent throughout the study.

Example 9

Selvamicin In Vivo Antifungal Activity

Selvamicin was tested in the neutropenic mouse disseminated candidiasis model. Mice were infected with an inoculum of *C. albicans*, *C. glabrata*, and *C. auris*. After infection, the mice were administered either saline or selvaimicin at 20 mg/kg or 80 mg/kg via an intraperitoneal route. After therapy, the burden of *Candida albicans* in mouse kidneys was measured by viable plate counts of organ homogenates. Selvamicin demonstrated efficacy in preventing *C. albicans*, *C. glabrata*, and *C. auris* growth in a dose dependent fashion following administration (FIG. 23, Panel B and C).

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

All publications, patents, patent applications and sequence accession numbers mentioned herein are hereby incorporated by reference in their entirety as if each individual publication, patent or patent application was specifically and individually indicated to be incorporated by reference. In case of conflict, the present application, including any definitions herein, will control.

What is claimed is:

1. A compound having a structure of Formula I or Formula II or a pharmaceutically acceptable salt thereof:

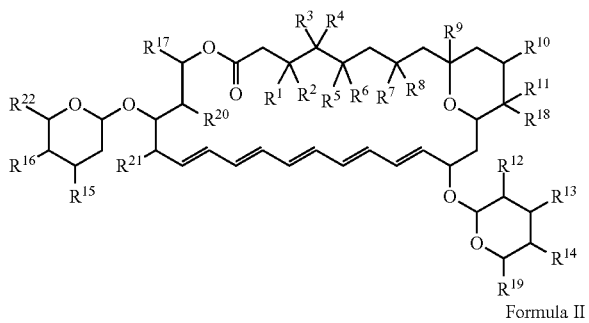

Formula I

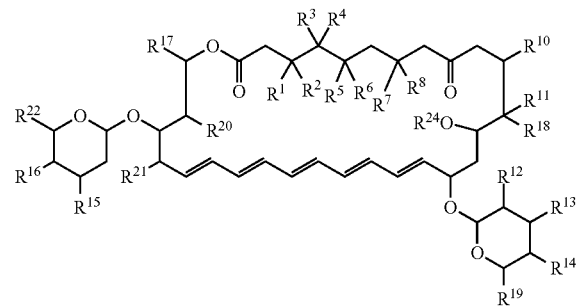

Formula II wherein $R^1$ and $R^2$ are, independently for each occurrence, H or $OR^{23}$, or $R^1$ and $R^2$ together with the carbon to which they are bound form a carbonyl moiety;

$R^3$ and $R^4$ are, independently for each occurrence, H or $OR^{23}$, or $R^3$ and $R^4$ together with the carbon to which they are bound form a carbonyl moiety;

$R^5$ and $R^6$ are, independently for each occurrence, H or $OR^{23}$, or $R^5$ and $R^6$ together with the carbon to which they are bound form a carbonyl moiety;

$R^7$ and $R^8$ are, independently for each occurrence, H or $OR^{23}$, or $R^7$ and $R^8$ together with the carbon to which they are bound form a carbonyl moiety;

$R^9$, $R^{10}$, $R^{11}$, $R^{12}$, $R^{13}$, $R^{14}$, $R^{15}$, and $R^{16}$ are, independently for each occurrence, H or $OR^{23}$;

$R^{17}$, $R^{18}$, $R^{19}$, $R^{20}$, $R^{21}$, and $R^{22}$ are, independently for each occurrence, H or optionally substituted alkyl;

$R^{23}$ is, independently for each occurrence, H, optionally substituted alkyl, or optionally substituted acyl; and $R^{24}$ is, independently for each occurrence, H, optionally substituted alkyl, or optionally substituted acyl.

2. The compound of claim 1, wherein the compound has a structure of Formula III or Formula IV or a pharmaceutically acceptable salt thereof:

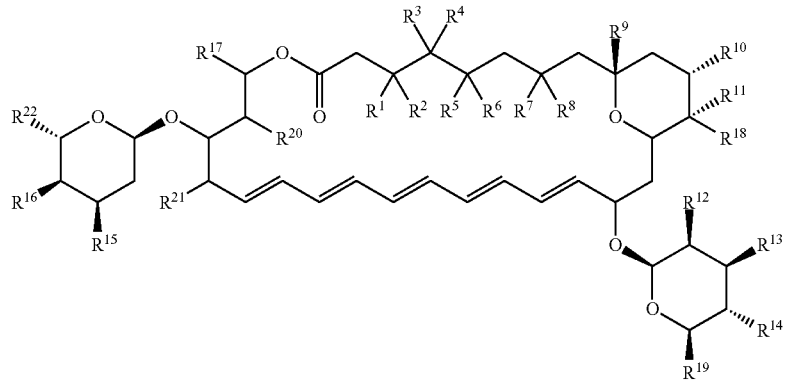
Formula III
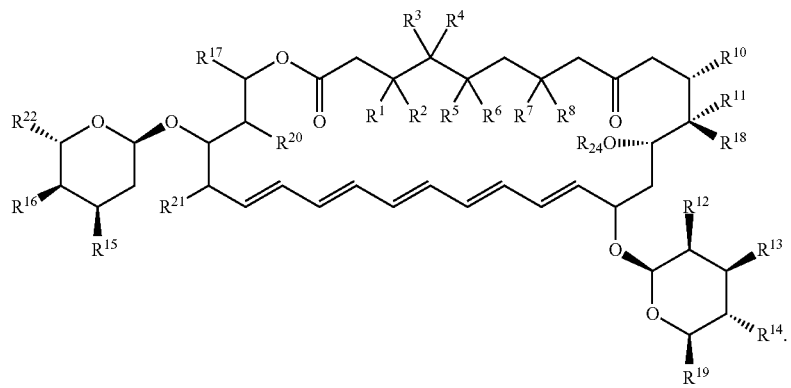
Formula IV
3. The compound of claim 1, wherein the compound has the structure
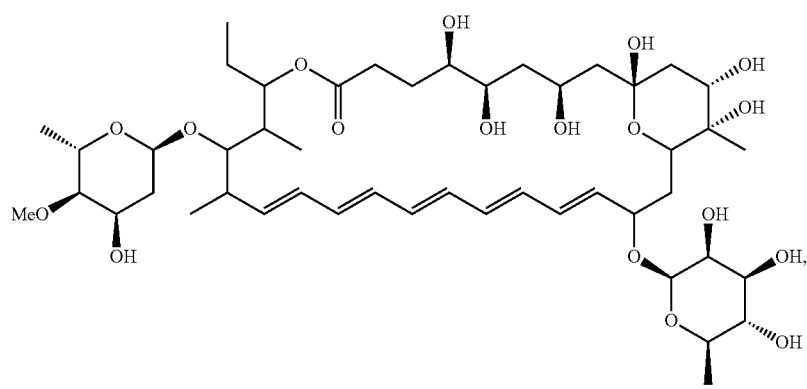
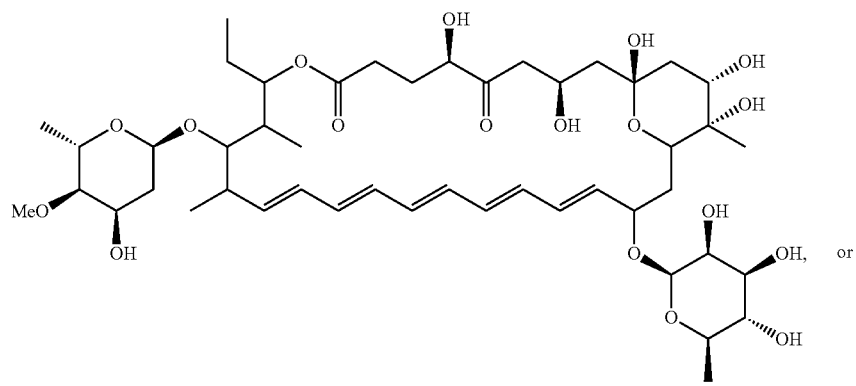
or -continued

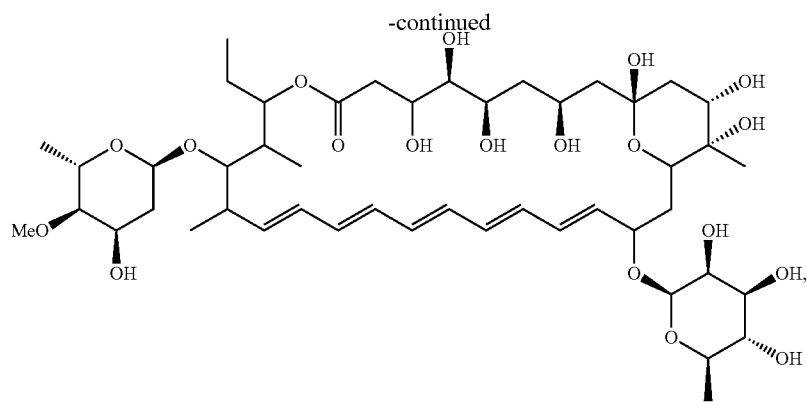

or a pharmaceutically acceptable salt thereof.

4. A pharmaceutical composition comprising a compound of claim 1 and a pharmaceutically acceptable carrier.

5. A method of inhibiting the growth of a fungus, the method comprising contacting a fungus with a compound of claim 1.

6. The method of claim 5, wherein the fungus is selected from *Candida albicans, Candida glabrata, Candida auris, Saccharomyces cerevisiae, Trichoderma harzianum*, and *Aspergillus fumigatus*.

7. A method of treating or lessening the severity of a fungal infection in a subject, the method comprising administering to the subject a compound of claim 1.

8. The method of claim 7, wherein fungal infection is infection with a fungus selected from *Candida albicans, Candida glabrata, Candida auris, Saccharomyces cerevisiae, Trichoderma harzianum*, and *Aspergillus fumigatus*.

9. A method of treating candidiasis in a subject, the method comprising administering to the subject a compound of claim 1.

* * * * *